US011505537B2

(12) United States Patent
Mickle et al.

(10) Patent No.: US 11,505,537 B2
(45) Date of Patent: *Nov. 22, 2022

(54) COMPOSITIONS COMPRISING METHYLPHENIDATE-PRODRUGS, PROCESSES OF MAKING AND USING THE SAME

(71) Applicant: KemPharm, Inc., Celebration, FL (US)

(72) Inventors: Travis Mickle, Kissimmee, FL (US); Sven Guenther, Coralville, IA (US); Guochen Chi, Coralville, IA (US)

(73) Assignee: KEMPHARM, INC., Celebration, FL (US)

(*) Notice: Subject to any disclaimer, the term of this patent is extended or adjusted under 35 U.S.C. 154(b) by 56 days.

This patent is subject to a terminal disclaimer.

(21) Appl. No.: 17/115,425

(22) Filed: Dec. 8, 2020

(65) Prior Publication Data
US 2021/0130322 A1 May 6, 2021

Related U.S. Application Data

(63) Continuation-in-part of application No. 16/794,170, filed on Feb. 18, 2020, now Pat. No. 10,954,213, which is a continuation of application No. 16/431,422, filed on Jun. 4, 2019, now Pat. No. 10,584,113, which is a continuation of application No. 16/431,275, filed on Jun. 4, 2019, now Pat. No. 10,584,112, which is a continuation of application No. PCT/US2017/065482, filed on Dec. 9, 2017.

(60) Provisional application No. 62/541,695, filed on Aug. 5, 2017, provisional application No. 62/519,627, filed on Jun. 14, 2017, provisional application No. 62/432,675, filed on Dec. 11, 2016.

(51) Int. Cl.
A61K 9/00 (2006.01)
A61K 31/4545 (2006.01)
A61K 47/54 (2017.01)
A61K 31/4458 (2006.01)
C07D 401/12 (2006.01)
C07D 211/34 (2006.01)

(52) U.S. Cl.
CPC .......... C07D 401/12 (2013.01); A61K 9/0053 (2013.01); A61K 31/4458 (2013.01); A61K 31/4545 (2013.01); A61K 47/545 (2017.08); C07D 211/34 (2013.01)

(58) Field of Classification Search
CPC .................... A61K 31/4458; A61K 31/4545
See application file for complete search history.

(56) References Cited

U.S. PATENT DOCUMENTS

| 5,908,850 | A | 6/1999 | Zeitlin et al. |
| 6,210,705 | B1 | 4/2001 | Mantelle et al. |
| 8,101,782 | B2 | 1/2012 | Rupniak et al. |
| 8,632,750 | B2 | 1/2014 | Suffin et al. |
| 8,969,337 | B2 | 3/2015 | Blumberg et al. |
| 9,079,928 | B2 | 7/2015 | Guenther et al. |
| 9,453,037 | B2 | 9/2016 | Buenther et al. |
| 10,584,112 | B2* | 3/2020 | Mickle .................. A61P 25/26 |
| 10,584,113 | B2* | 3/2020 | Mickle ................ A61K 9/0053 |
| 10,759,778 | B2* | 9/2020 | Mickle ................ C07D 401/12 |
| 10,954,212 | B2* | 3/2021 | Mickle .............. A61K 31/4545 |
| 2002/0103162 | A1 | 8/2002 | Epstein et al. |
| 2002/0132793 | A1 | 9/2002 | Epstein et al. |
| 2004/0063628 | A1 | 4/2004 | Piccariello et al. |
| 2006/0100243 | A1 | 5/2006 | Froimowitz et al. |
| 2007/0042955 | A1 | 2/2007 | Mickle et al. |
| 2007/0123468 | A1 | 5/2007 | Jenkins |
| 2008/0139653 | A1 | 6/2008 | Mickle |
| 2009/0137486 | A1 | 5/2009 | Mickle et al. |
| 2010/0145057 | A1 | 6/2010 | Thennati et al. |
| 2010/0249242 | A1 | 9/2010 | Poulsen et al. |
| 2011/0021564 | A1 | 1/2011 | Sanfilippo |
| 2011/0213034 | A1 | 9/2011 | Mickle |

(Continued)

FOREIGN PATENT DOCUMENTS

| JP | 2002510318 | 12/2005 |
| WO | 1999/036403 | 7/1999 |
| WO | 2004080959 | 9/2004 |

(Continued)

OTHER PUBLICATIONS

Israel Patent Office, Office Action for Patent Application No. 267172, 14 pages, dated May 23, 2021.
China National Intellectual Property Administration, Office Action for Application No. 2017800787184, 11 pages, dated Dec. 8, 2021.
Brazilian Patent Office (translation), Office Action for Patent Application No. BR 11 2019 011640, 3 pages, dated Apr. 7, 2021.
Mew Zealand Intellectual Property Office, Patent examination report 1, issued in connection with patent application No. 754751, Aug. 20, 2021, 4 pages.
Extended International Search Report regarding PCT Application No. PCT/US2004/017204, dated Jun. 23, 2020, 9 pgs.
Ermer, James C., et al., Lisdexamfetamine Dimesylate: Prodrug Delivery, Amphetamine Exposure and Duration of Efficacy, published online: Mar. 28, 2016, 16 pgs.

(Continued)

Primary Examiner — James D. Anderson
(74) Attorney, Agent, or Firm — McAndrews, Held & Malloy, Ltd.

(57) ABSTRACT

The present technology is directed to compositions comprising d-threo-methylphenidate conjugates and/or unconjugated methylphenidate. The present technology also relates to compositions and oral formulations comprising d-threo-methylphenidate conjugated to nicotinoyl-L-serine, and/or a pharmaceutically acceptable salt thereof, and unconjugated methylphenidate and/or a pharmaceutically acceptable salt thereof. The present technology additionally relates to a pharmaceutical kit containing the composition comprising d-threo-methylphenidate conjugated to nicotinoyl-L-serine, and/or a pharmaceutically acceptable salt thereof, and unconjugated methylphenidate and/or a pharmaceutically acceptable salt thereof.

12 Claims, 19 Drawing Sheets

(56) References Cited

U.S. PATENT DOCUMENTS

| | | | |
|---|---|---|---|
| 2014/0024329 A1 | 8/2014 | Guenther et al. | |
| 2014/0243291 A1* | 8/2014 | Guenther | A61P 25/24 514/315 |

FOREIGN PATENT DOCUMENTS

| | | |
|---|---|---|
| WO | PCT/US2004/017204 | 1/2005 |
| WO | 2008097546 | 8/2008 |
| WO | 2008147518 | 12/2008 |
| WO | 2009035473 | 3/2009 |
| WO | 2013016668 | 1/2013 |
| WO | 2018/107131 | 6/2018 |
| WO | 2018/107132 | 6/2018 |

OTHER PUBLICATIONS

Israeli Patent Office, Office Action regarding Application No. 267172, dated Oct. 25, 2020, 19 pages.

Japan Patent Office, Office Action for Patent Application No. 2019-530444, dated Jan. 19, 2021, 6 pages.

Korean Patent Office, Office Action for Patent Application No. 2019-7017411, dated Jan. 29, 2021, 9 pages.

Destevens, G.: "Investigations in Heterocycles. XV. Methylphenidate : A Versatile Intermediate in the Synthesis of Bicyclic Heterocycles with Bridged Nitrogen Atom," J. Med. Chem., pp. 146-149, 1964.

Dias, Luiz C., et al.: "Short Synthesis of Methylphenidate and its p-Methoxy Derivative," Synthetic Communications, vol. 30, No. 7, p. 1313, 2000.

Misra M., et al., "Quantitative structure-activity relationship studies of threo-methylphenidate analogs," Bioorganic & Medicinal Chemistry, Pergamon, GB, vol. 18, No. 20, pp. 7221-7238, 2010.

Pilli et al., "The Stereochemistry of the Addition of Chlorotitanium Enolates of N-Acyl Oxazolidin-2-ones to 5- and 6-Membered N-Acyliminium Ions." J. Braz. Chem. Soc., vol. 12, No. 5, pp. 634-651, 2001.

EESR for International Patent Application No. PCT/US2012/048641 dated Jan. 23, 2015.

Notice of Allowance for U.S. Appl. No. 14/234,440 dated Dec. 4, 2014.

Notice of Allowance for U.S. Appl. No. 14/234,440 dated Mar. 16, 2015.

Japanese Office Action for JP Appl No. 014-523083, dated Mar. 30, 2016.

Alexander et al., "(Acyloxy)alkyl Carbamates as Novel Bioreversible Prodrugs for Amines: Increased Permeation through biological Membranes," J. Med. Chem, 1988, pp. 318-322.

Ribeiro et al., "Aminocarbonyloxymethyl Ester Prodrugs of Flufenamic Acid and Diclofenac: Suppressing the Rearrangement Pathway in Aqueous Media," Arch. Pharm. Chem Life Sci., 2007, pp. 32-40.

Canadian Examiner's Report for Application No. 2,837,732, dated Dec. 12, 2016.

Restriction Requirement for U.S. Appl. No. 15/249,088, dated Jan. 30, 2017.

Extended European Search Report for Appl No. 17157635.8, dated May 4, 2017.

Office Action for U.S. Appl. No. 14/727,498, dated Feb. 11, 2016.

Notice of Allowance for U.S. Appl. No. 14/727,498, dated Jun. 23, 2016.

Notice of Allowance for Japan Patent Application No. 2016-139995, dated Dec. 5, 2017, 4 pages.

Final Rejection for Korea Patent Application No. 10-2016-7010571, dated Jan. 10, 2018, 6 pages.

Examination Report for India Patent Application No. 11264/DELNP/2013, dated Jan. 23, 2018, 7 pages.

Notice of Allowance of Korea Patent Application No. 10-2016-7010571, dated Mar. 14, 2018, 6 pages.

International Search Report for PCT Application No. PCT/US17/65482, dated Feb. 1, 2018, 4 pages.

IPRP for International Application No. PCT/US2017/065482 dated Jun. 20, 2019, 9 pages.

International Search Report regarding PCT Application No. PCT/US2019/035803, dated Aug. 19, 2019, 11 pgs.

Mickle, Travice C., et al.: "Pharmacokinetics and Abuse Potential of Benzhydrocodone, A Novel Prodrug of Hydrocodone, After Intranasal Administration in Recreational Drug Users," Pain Med., 19(12):12438-2449, Dec. 2018.

Rochdi, M., et al.: "Dose-proportional pharmacokinetics of a methylphenidate extended-release capsule," Int. J. Pharmacol. Ther., 42(5)285-92, May 2004.

Tuerck, D., et al.: "Dose-proportional pharmacokinetics of d-threo-methylphenidate after a repeated-action release dosage form," J. Clin. Pharmacol., 47(1):64-69, Jan. 2007.

\* cited by examiner

COMPOSITIONS COMPRISING METHYLPHENIDATE-PRODRUGS, PROCESSES OF MAKING AND USING THE SAME

RELATED APPLICATIONS

The present patent application is a continuation-in-part of U.S. patent application Ser. No. 16/794,170, filed on Feb. 18, 2020, which is a continuation of U.S. patent application Ser. No. 16/431,422, filed on Jun. 4, 2019, which is a continuation of U.S. patent application Ser. No. 16/431,275, filed on Jun. 4, 2019, which is a continuation of PCT/US2017/065482, filed on Dec. 9, 2017, The present application claims priority to U.S. Provisional Patent Application No. 62/432,675 filed on Dec. 11, 2016, U.S. Provisional Patent Application No. 62/519,627 filed on Jun. 14, 2017, and U.S. Provisional Application No. 62/541,695, filed Aug. 5, 2017, each of which is incorporated by reference in its entirety.

FEDERALLY SPONSORED RESEARCH OR DEVELOPMENT

[Not Applicable]

BACKGROUND OF THE INVENTION

Methylphenidate is a psychostimulant which is a chain substituted amphetamine derivative. Similar to amphetamine and cocaine, methylphenidate targets the central nervous system, specifically the dopamine transporter (DAT) and norepinephrine transporter (NET). Methylphenidate is thought to act by increasing the concentrations of dopamine and norepinephrine in the synaptic cleft, as methylphenidate has both dopamine transporter (DAT) and norepinephrine transporter (NET) binding capabilities. Although an amphetamine derivative, the pharmacology of methylphenidate and amphetamine differ, as amphetamine is a dopamine transport substrate whereas methylphenidate works as a dopamine transport blocker. As a norepinephrine and dopamine re-uptake inhibitor, methylphenidate thus blocks re-uptake of dopamine and norepinephrine (noradrenaline) into presynaptic neurons (and possibly stimulates the release of dopamine from dopamine nerve terminals at high doses), thereby increasing the levels of dopamine and norepinephrine in the synapse. In some in vitro studies, methylphenidate has been shown to be more potent as an inhibitor of norepinephrine uptake/re-uptake when compared to dopamine. However, some in vivo studies have indicated that methylphenidate is more potent in potentiating extracellular dopamine concentrations than norepinephrine concentrations. Unlike amphetamine, it has been suggested in the scientific and/or clinical research community that methylphenidate does not seem to significantly facilitate the release of these two monoamine neurotransmitters at therapeutic doses.

Four isomers of methylphenidate are known to exist: d-erythro-methylphenidate, l-erythro-methylphenidate, d-threo-methylphenidate, and l-threo-methylphenidate. Originally, methylphenidate was marketed as a mixture of two racemates, d/l-erythro-methylphenidate and d/l-threo-methylphenidate. Subsequent research showed that most of the desired pharmacological activity of the mixture is associated with the threo-isomer resulting in the marketing of the isolated threo-methylphenidate racemate. Later, the scientific community determined that the d-threo-isomer is mostly responsible for the stimulant activity. Consequently, new products were developed containing only d-threo-methylphenidate (also known as "d-threo-MPH").

Stimulants, including methylphenidate ("MPH"), are believed to enhance the activity of the sympathetic nervous system and/or central nervous system (CNS). Stimulants such as MPH and the various forms and derivatives thereof are used for the treatment of a range of conditions and disorders predominantly encompassing, for example, sleep disorders, including, but not limited to narcolepsy, excessive daytime sleepiness, central hypersomnolence disorders and/or wakefulness.

Methylphenidate is currently approved by the United States Food and Drug Administration ("FDA") for the treatment of narcolepsy. Methylphenidate has also shown efficacy for some off-label indications that include depression, obesity and lethargy. In some embodiments, the prodrugs of the present technology may be administered for the treatment of narcolepsy, or any condition that requires the blocking of the norepinephrine and/or dopamine transporters.

Stimulants, such as methylphenidate and amphetamine, have been shown in the conventional art to exhibit noradrenergic and dopaminergic effects that can lead to cardiovascular events comprising, for example, increased heart rate, hypertension, palpitations, tachycardia and in isolated cases cardiomyopathy, stroke, myocardial infarction and/or sudden death. Consequently, currently available stimulants expose patients with pre-existing structural cardiac abnormalities or other severe cardiac indications to even greater health risks and are frequently not used or used with caution in this patient population.

Methylphenidate, like other stimulants and amphetamine derivatives, can become addictive and is prone to substance abuse. Oral abuse has been reported, and euphoria can be achieved through intranasal and intravenous administration.

Dependence on stimulants like cocaine can occur even after usage for a very short period of time due to their potent euphoric effects. For example, early signs of cocaine dependence include difficulty to abstain from cocaine use when it is present or available. Many stimulants including cocaine have a short elimination half-life and thus require frequent dosing to maintain the "high". Chronic use of supratherapeutic doses of such stimulants may result in numerous mental and/or physical problems. Effects on mood may include anxiety, restlessness, feelings of superiority, euphoria, panic, irritation, and fearfulness. Behavioral symptoms include, but are not limited to being extremely talkative, having increased energy, stealing or borrowing money, erratic or odd behavior, violence, lack of participation in activities that were once enjoyable, and reckless and risky behaviors. Examples of physical symptoms of stimulant dependence may include one or more of the following: decreased need to sleep, headaches, nosebleeds, hoarseness, increased heart rate, muscle twitches, malnutrition, increase in body temperature, nasal perforation, abnormal heart rhythms, chronic runny nose, constricting blood vessels, increased heart rate, increased blood pressure, sexual dysfunction, decreased appetite, dilated pupils, risks for contracting Human Immunodeficiency Virus (HIV), hepatitis C and other bloodborne diseases, gangrene of the bowel, cravings, and tremors. Examples of psychological symptoms of stimulant dependence may include one or more of the following: severe paranoia, violent mood swings, break from reality, lack of motivation, psychosis, hallucinations, inability to use sound judgment, and the rationalization of drug use. There is a variety of factors that can trigger or play a role in stimulant use disorder or stimulant dependence. Generally, these factors can be placed into three categories: genetic, biological, and environmental. Research has shown that individuals who have relatives with addiction problems are more likely to develop an addiction including cocaine dependence. The likelihood of becoming stimulant dependent is higher if the relative is a parent. Changes in brain function may be a biological factor that correlates with addiction problems. For example, low dopamine levels in the brain may result in an individual to abuse substances with the goal to attain pleasurable feelings. Environmental factors include but are not limited to unpredictable situations in the home lives of an individual; stressors, such as child abuse, the loss of a loved one, or other traumatic events. There is a need in the art for forms of methylphenidate that have a slow gradual increase in methylphenidate blood/brain concentrations until peak concentrations are achieved, or a slow gradual decrease of methylphenidate blood/brain concentrations after peak concentrations, or both. Not wishing to be bound by any particular theory, it is possible that slow onset of stimulant concentrations can decrease cardiovascular side effects, and slow elimination can decrease rebound effects. It has also been suggested that a larger increase in synaptic dopamine per time unit (i.e., higher rate of dopamine increase) results in more robust and intense euphoric effect. A slow increase in methylphenidate brain concentration produces a low rate of increase in synaptic dopamine and thus, may result in less rewarding and reinforcing effects. Without wishing to be bound by any particular theory, it has also been suggested that high occupancy of dopamine transporter receptors may decrease the rewarding and reinforcing effects of additional doses of stimulants like cocaine. This could be accomplished, for example, by repeated administration of large doses of a form of methylphenidate with a slow onset that does not result in euphoria.

There is also a need in the art for forms of methylphenidate that can provide a more rapid onset of methylphenidate blood/brain concentrations. Not wishing to be bound by any theory, certain indications may require a large and fast initial spike in blood and/or brain concentration of methylphenidate to provide to the subject sufficient efficacy, while other indications may require lower blood/brain concentrations of methylphenidate, but a small therapeutic amount of a form of methylphenidate with rapid onset may still be beneficial to provide fast efficacy when needed.

There is a further need in the art for forms of methylphenidate that can provide flexibility in dosing regimens. For example, a single daily dose form of methylphenidate in a composition that can provide both immediate and extended release PK profiles would be highly desirable.

There is an additional need in the art for forms of methylphenidate that can maintain the pharmacological benefit when administered, in particular via the oral route, but which preferably have no or a substantially decreased pharmacological activity when administered through injection or intranasal routes of administration.

BRIEF SUMMARY OF THE INVENTION

The present technology provides a particular d-threo-methylphenidate ("d-MPH", "d-methylphenidate", "dexmethylphenidate") conjugate, or pharmaceutically acceptable salts thereof, to provide, for example, at least one single daily dose form of a d-methylphenidate conjugate in a composition with unconjugated methylphenidate that can provide both immediate and extended release PK profiles when compared to unconjugated d-methylphenidate. The release profile, in some instances, provides the ability of the prodrug or composition to be administered using dosing regimens that are not easily utilized with the unconjugated d-methylphenidate. In some embodiments, the unconjugated methylphenidate in the composition can be d-methylphenidate, l-methylphenidate, or a mixture thereof, and/or a therapeutic or pharmaceutically acceptable salt thereof.

In another aspect, the present technology provides a prodrug composition comprising at least one conjugate of d-methylphenidate having a structure of Formula I:

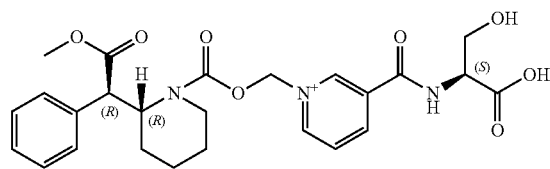

and unconjugated methylphenidate, wherein the unconjugated methylphenidate comprises d-methylphenidate.

In another aspect, the present technology provides at least one prodrug composition comprising at least one conjugate, wherein the at least one conjugate is d-methylphenidate-$CO_2CH_2$-nicotinoyl-L-Ser (Formula I), or pharmaceutically acceptable salts thereof, and unconjugated methylphenidate.

In a further aspect, the present technology provides a composition comprising unconjugated methylphenidate and at least one conjugate, wherein the at least one conjugate has at least two or more chiral centers and the composition is optically active.

In yet another aspect, the present technology provides a method for chemically synthesizing a d-methylphenidate-$CO_2CH_2$-nicotinoyl-L-Ser conjugate of the present technology by performing the appropriate steps to conjugate d-methylphenidate to the —$CO_2CH_2$-nicotinoyl-L-Ser ligand.

In further aspects, some embodiments of the compositions of the present technology, comprising (a) the conjugate of Formula I and/or its pharmaceutically acceptable salt(s) and (b) unconjugated methylphenidate (comprising d-methylphenidate) and/or its pharmaceutically acceptable salts, unexpectedly exhibit increased plasma concentrations of d-methylphenidate after $T_{max}$ (or later) resulting in a controlled or extended-release profile as compared to an equimolar dose of unmodified d-methylphenidate.

In another aspect, some embodiments of the compositions of the present technology, comprising (a) the conjugate of Formula I and/or its pharmaceutically acceptable salt(s) and (b) unconjugated methylphenidate (comprising d-methylphenidate) and/or its pharmaceutically acceptable salts, exhibit increased plasma concentrations of d-methylphenidate from about 0 to about 4 hours following oral administration as compared to an orally administered equimolar dose of unconjugated d-methylphenidate released from Concerta®.

In a further aspect, some embodiments of the compositions of the present technology, comprising (a) the conjugate of Formula I and/or its pharmaceutically acceptable salt(s) and (b) unconjugated methylphenidate (comprising d-methylphenidate) and/or its pharmaceutically acceptable salts, exhibit increased plasma concentrations of d-methylphenidate for up to about 4 hours following oral administration as compared to an orally administered equimolar dose of unconjugated d-methylphenidate released from Concerta®.

In yet a further aspect, some embodiments of the compositions of the present technology, comprising (a) the conjugate of Formula I and/or its pharmaceutically acceptable salt(s) and (b) unconjugated methylphenidate and/or its pharmaceutically acceptable salts, surprisingly exhibit less interpatient variability in the oral pharmacokinetic (PK) profile when compared to unconjugated d-methylphenidate.

In yet another aspect, some embodiments of the compositions of the present technology are provided in an amount sufficient to provide an increased AUC when compared to unconjugated d-methylphenidate when administered orally at equimolar doses.

In still further aspects, some embodiments of the compositions of the present technology are provided in an amount sufficient to provide a surprisingly lower $C_{max}$ and a lower AUC but significantly increased partial AUCs for time periods after $T_{max}$ (or later) of the released d-methylphenidate as compared to unconjugated d-methylphenidate when administered orally at equimolar doses.

In yet further aspects, some embodiments of the compositions of the present technology are provided in an amount sufficient to provide a lower $C_{max}$ and a similar AUC, but significantly increased partial AUCs for time periods after $T_{max}$ (or later) of the released d-methylphenidate as compared to unconjugated d-methylphenidate when administered orally at equimolar doses.

In yet an alternative aspect, some embodiments of the compositions of the present technology are believed to provide reduced side effects as compared to unconjugated d-methylphenidate when administered at equimolar doses, and are also contemplated in some alternative aspects to provide reduced abuse potential as compared to unconjugated d-methylphenidate.

In addition, some embodiments of the compositions of the present technology are also believed to unexpectedly provide an amount sufficient to provide an extended $T_{max}$ when compared to unconjugated d-methylphenidate when administered at equimolar doses, and/or provide an equivalent $T_{max}$ when compared to unconjugated d-methylphenidate when administered orally at equimolar doses.

Further, some embodiments of the compositions of the present technology are also believed to unexpectedly provide an amount sufficient to provide a shorter $T_{max}$ when compared to an orally administered equimolar dose of unconjugated d-methylphenidate released from Concerta®.

In addition, some embodiments of the compositions of the present technology are also believed to unexpectedly provide an amount sufficient to provide a longer half-life ($T_{1/2}$) when compared to an orally administered equimolar dose of unconjugated d-methylphenidate released from Concerta®.

In addition, some embodiments of the compositions of the present technology are also believed to unexpectedly provide an amount sufficient to provide a longer $T_{1/2}$ compared to unconjugated d-methylphenidate when administered orally at equimolar doses.

Moreover, the present technology provides at least one method of treating one or more subjects (human or animal) or patients (human or animal) having at least one disease, disorder or condition mediated by controlling, preventing, limiting, or inhibiting neurotransmitter uptake/re-uptake or hormone uptake/re-uptake comprising orally administering to one or more subjects or patients a pharmaceutically and/or therapeutically effective amount of a composition of the present technology, comprising unconjugated methylphenidate and/or its pharmaceutically acceptable salts, and a conjugate of Formula I and/or its pharmaceutically acceptable salts.

In still yet a further aspect, the present technology provides at least one method of treating a subject (human or animal) having at least one disorder or condition requiring stimulation of the central nervous system of the subject, comprising orally administering a pharmaceutically effective amount of a composition of the present technology, comprising unconjugated methylphenidate and/or its pharmaceutically acceptable salts and a conjugate of Formula I and/or its pharmaceutically acceptable salts, wherein the administration treats at least one disorder or condition requiring stimulation of the central nervous system of the subject.

In still yet a further aspect, the present technology provides at least one method of treating a subject (human or animal) having at least one disorder or condition requiring stimulation of the central nervous system of the subject, comprising orally administering a therapeutically effective amount of a composition of the present technology, comprising unconjugated methylphenidate and/or its pharmaceutically acceptable salts and a conjugate of Formula I and/or its pharmaceutically acceptable salts, wherein the administration treats at least one disorder or condition requiring stimulation of the central nervous system of the subject.

In yet another aspect, the present technology provides one or more methods of administering to a subject a composition comprising at least one conjugate of d-methylphenidate and unconjugated methylphenidate, wherein the administration decreases the number of and/or the amount of metabolites produced when compared with unconjugated d-methylphenidate. In other aspects, the one or more methods of administering the composition of the present technology is believed to decrease the exposure of the subject to ritalinic acid when compared with unconjugated d-methylphenidate. It is desirable to minimize exposure to metabolites, such as ritalinic acid, that do not contribute significantly to the intended therapeutic effect because of potential side effects or toxicity that may still occur as a result of potential secondary pharmacological effects of the metabolite. In some embodiments, compositions of the present technology may reduce overall exposure to ritalinic acid by about 25% to about 75%.

In yet a further embodiment, the compositions of the present technology are believed to provide an increased water solubility of the d-methylphenidate-based conjugate or prodrug compared to unconjugated d-methylphenidate. In another embodiment, the increased water solubility is believed to allow for the compositions to be formed into certain dosage forms at higher concentrations, dosage strengths, or higher dose loading capacities than unconjugated d-methylphenidate. In some embodiments, such dosage forms include, for example, oral thin films or strips.

In still yet a further embodiment, the administration to a patient (human or animal) of the d-methylphenidate-based compositions comprising d-methylphenidate conjugates and unconjugated methylphenidate are believed to provide a reduced interpatient variability of d-methylphenidate plasma concentrations, and are believed to have an improved safety profile when compared to unconjugated d-methylphenidate.

In yet another alternative embodiment, the present technology provides at least one method of treating attention-deficit hyperactivity disorder comprising administering to a subject or patient a pharmaceutically and/or therapeutically effective amount of a composition comprising at least one d-methylphenidate conjugate and unconjugated methylphenidate, wherein the administration treats attention-deficit hyperactivity disorder in the subject.

In yet another alternative embodiment, the present technology provides at least one method of treating an eating disorder, binge eating disorder, obesity, cocaine dependence, or stimulant dependence in a subject or patient comprising administering to a subject or patient a pharmaceutically and/or therapeutically effective amount of a composition comprising at least one d-methylphenidate conjugate and unconjugated methylphenidate, wherein the administration treats an eating disorder, binge eating disorder, obesity, cocaine dependence, or stimulant dependence in a subject or patient.

In yet another alternative embodiment, the present technology provides at least one method of treating a sleep disorder, including, but not limited to, central hypersomnolence disorders narcolepsy, chronic fatigue, sleep disorder, and excessive daytime sleepiness (EDS) in a subject or patient comprising administering to a subject or patient a pharmaceutically and/or therapeutically effective amount of a composition comprising at least one d-methylphenidate conjugate and unconjugated methylphenidate, wherein the administration treats a sleep disorder.

In another further embodiment, the present technology provides a composition for treating at least one subject or patient having a disorder or condition requiring stimulation of the central nervous system of the subject, wherein the composition comprises unconjugated methylphenidate and a d-methylphenidate conjugate, and wherein the composition has a reduced abuse potential when administered compared to unconjugated d-methylphenidate.

In a further embodiment, the compositions of the present technology are contemplated to exhibit reduced or prevented pharmacological activity when administered by parenteral routes, or reduced plasma or blood concentration of released d-methylphenidate when administered intranasally, intravenously, intramuscularly, subcutaneously or rectally as compared to free unconjugated d-methylphenidate when administered at equimolar amounts.

In some embodiments, the compositions of the present technology have an extended or controlled release profile as measured by plasma concentrations of released d-methylphenidate when compared to unconjugated d-methylphenidate when administered orally at equimolar doses. In some embodiments, the plasma concentration of d-methylphenidate released from the conjugate of the composition would increase more slowly and over a longer period of time after oral administration, resulting in a delay in peak plasma concentration of released d-methylphenidate and in a longer duration of action when compared to unconjugated d-methylphenidate. In further embodiments, the controlled release profile of d-methylphenidate of the composition would have a $T_{max}$ that is about equal to unconjugated d-methylphenidate, but provides plasma concentrations of d-methylphenidate that are sustained for a longer period of time as compared to unconjugated d-methylphenidate.

In other embodiments, the composition has a lower AUC and lower $C_{max}$, but an equivalent $T_{max}$ and higher d-methylphenidate plasma concentrations in the second half of the day when administered orally once per day compared to unconjugated d-methylphenidate administered orally once per day.

In another aspect, the present technology provides a pharmaceutical kit comprising a specified amount of individual doses in a package, each dose comprising a pharmaceutically and/or therapeutically effective amount of a composition comprising at least one conjugate of d-methylphenidate and unconjugated methylphenidate. The pharmaceutical kit also comprises instructions for use.

In another further aspect, the present technology provides an oral formulation. The oral formulation may comprise a therapeutic dose of (a) d-threo-methylphenidate (S)-serine conjugate and/or its pharmaceutically acceptable salts, and (b) unconjugated methylphenidate and/or its pharmaceutically acceptable salts.

In certain embodiments, compositions of the present technology comprising unconjugated methylphenidate and at least one conjugate of d-methylphenidate can be used in neonatal, pediatric, adolescent, adult and/or geriatric subjects with sleep disorders. For example, in some embodiments, the present compositions can be used for a once-daily dosing with a potentially improved onset and a long duration of action, attributes that may benefit neonatal, pediatric and/or adolescent subjects with sleep disorders.

DETAILED DESCRIPTION OF THE INVENTION

Figure 1:
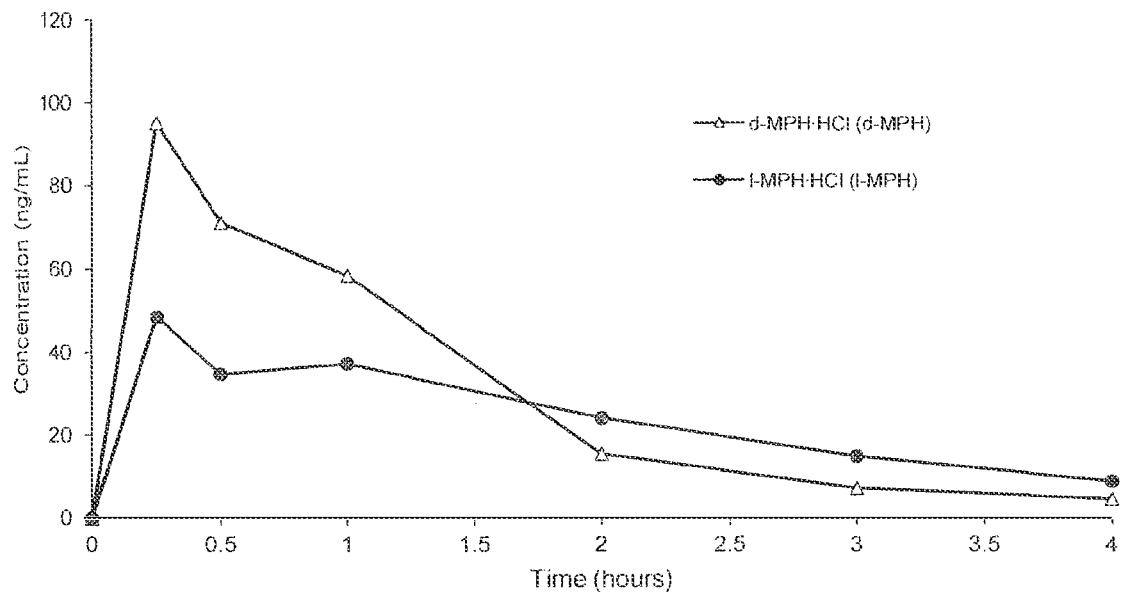
FIG. 1. Oral PK curves comparing the bioavailability of d-MPH and l-MPH with unconjugated methylphenidate in rats.

The present technology provides one or more compositions comprising (a) unconjugated methylphenidate and (b) d-methylphenidate conjugated to a nicotinoyl-L-serine moiety to form a prodrug. The composition has surprising beneficial properties as further described herein.

The use of the term "methylphenidate" herein is meant to include any of the stereoisomer forms of methylphenidate, including the four stereoisomers: d-erythro-methylphenidate, l-erythro-methylphenidate, d-threo-methylphenidate and l-threo-methylphenidate and the salts and derivatives thereof. Methylphenidate is interchangeable with methyl phenyl(piperidin-2-yl)acetate. The term "methylphenidate" includes all salt forms. Methylphenidate is also known by its trade name Concerta® (commercially available from Janssen Pharmaceuticals, Inc., Beerse, Belgium), Ritalin®, Ritalin® SR, Methylin®, Methylin® ER (all commercially available from Novartis International AG, of Basil, Switzerland). The methylphenidate used in the present technology can be any stereoisomer of methylphenidate, including, but not limited to, d-erythro-methylphenidate, l-erythro-methylphenidate, d-threo-methylphenidate and l-threo-methylphenidate. In a preferred embodiment, the conjugates contain a single d-threo-methylphenidate isomer. In another embodiment, the prodrug conjugates are optically active single isomers thereof.

The use of the term "unconjugated methylphenidate" means methyl 2-phenyl-2-(piperidin-2-yl)acetate and salts thereof.

Stereoisomers, used hereinafter, means that two molecules are described as stereoisomers of each other if they are made of the same atoms, connected in the same sequence, but the atoms are positioned differently in space. The difference between two stereoisomers can only be seen when the three-dimensional arrangement of the molecules is considered.

Bioavailability, used hereinafter, means the proportion of a drug or other substance that enters the circulation over time when introduced into the body and so is able to have an active effect.

$C_{max}$, used hereinafter, is a term used in pharmacokinetics and refers to the maximum (or peak) plasma concentration that a drug achieves in a specified compartment or test area of the body after the drug has been administered and before the administration of a second dose.

$T_{max}$, used hereinafter, is the term used in pharmacokinetics to describe the time at which infix is observed. After an intravenous administration, $C_{max}$ and $T_{max}$ are closely dependent on the experimental protocol, since the concentrations are always decreasing after the dose.

As known to those skilled in the art, the term "Steady State" means the state in which the overall intake of a drug is in approximate dynamic equilibrium with its elimination. At steady state, total drug exposure does not change significantly between successive dosing periods. Steady state is typically achieved following a time period about 4-5 times the half-life of a drug after regular dosing was started.

The use of the term "dose" means the total amount of a drug or active component taken each time by an individual subject.

As used herein, the term "subject" means a human or animal, including but not limited to a human or animal patient.

The term "patient" means a human or animal subject in need of treatment.

The use of the term "interpatient variability" means an estimate of the levels of pharmacokinetic variability between different individuals receiving the same dose of the same drug. The estimate can be made, for example, by calculating the coefficient of variation (CV) of certain pharmacokinetics parameters including, for example, $C_{max}$, $AUC_{last}$, $AUC_{inf}$, and $T_{max}$. When comparing interpatient variability between different drugs or between the same drug(s) in different formulations, lower CV indicates reduced interpatient variability and higher CV indicates increased interpatient variability.

"Coefficient of variant" (CV) is a term used in statistics and is calculated based on the following formula: CV=standard deviation/mean*100.

$AUC_{last}$ is a term used in pharmacokinetics to describe the area under the curve in a plot of drug concentration in blood, serum, or plasma vs time from time=0 (or predose) to the time of the last measurable drug concentration.

$AUC_{inf}$ is a term used in pharmacokinetics to describe the area under the curve in a plot of drug concentration in blood, serum, or plasma vs time from time=0 (or predose) to infinity.

Molar equivalent as used hereinafter, means an equal number of moles of the substance as the number of moles in a certain mass (weight) or volume, e.g. a dose of d-methylphenidate that is molar equivalent to a dose of about 0.1 mg d-methylphenidate hydrochloride per day would provide the same number of moles of d-methylphenidate as from 0.1 mg of d-methylphenidate hydrochloride.

As used herein, the phrases such as "decreased," "reduced," "diminished" or "lowered" are meant to include at least about a 10% change in pharmacological activity, area under the curve (AUC) and/or peak plasma concentration ($C_{max}$) with greater percentage changes being preferred for reduction in abuse potential and overdose potential of the conjugates of the present technology as compared to unconjugated methylphenidate. For instance, the change may also be greater than about 10%, about 15%, about 20%, about 25%, about 35%, about 45%, about 55%, about 65%, about 75%, about 85%, about 95%, about 96%, about 97%, about 98%, about 99%, or increments therein.

"Pharmaceutically effective amount" as used herein means an amount that has a pharmacological effect. A "pharmaceutically acceptable salt" as used herein is a salt of the d-methylphenidate conjugate or unconjugated methylphenidate or both which, when used in a pharmaceutically effective amount, has at least one pharmacological effect.

"Therapeutically effective amount" as used herein means an amount effective for treating a disease or condition. A "therapeutically acceptable salt" as used herein is a pharmaceutically acceptable salt of the d-methylphenidate conjugate or unconjugated methylphenidate or both in the composition of the present technology, which, when used in a therapeutically effective amount, is effective for treating a disease, condition, or syndrome.

As used herein, the term "attention deficit hyperactivity disorder" (ADHD) encompasses various sub-types of ADHD including, for example, subjects who do not show or only show weak symptoms of hyperactivity or impulsiveness, or for example, subjects who are predominately inattentive (formerly attention deficit disorder (ADD)).

As used herein, the term "prodrug" refers to a substance that is inactive or has reduced pharmacological activity but is converted to an active drug by a chemical or biological reaction in the body. In the present technology, the prodrug is a conjugate of at least one drug, d-methylphenidate, a linker, and a nicotinoyl-L-serine moiety. Thus, the conjugates of the present technology are prodrugs and the prodrugs of the present technology are conjugates.

Prodrugs are often useful because, in some embodiments, they may be easier to administer or process than the parent drug. They may, for instance, be more bioavailable by oral administration whereas the parent drug is not. The prodrug may also have improved solubility in water and/or other solvents over the parent drug. An embodiment of a prodrug would be a d-methylphenidate conjugate that is metabolized to the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug is designed to alter the metabolism or the transport characteristics of a drug—the changes typically varying with route of administration—in certain embodiments, to mask side-effects or toxicity, to improve bioavailability and/or water solubility, to improve the flavor of a drug or to alter other characteristics or properties of a drug in other discrete embodiments.

The d-methylphenidate prodrug can be prepared so as to have a variety of different chemical forms including chemical derivatives or salts. Such d-methylphenidate prodrugs can also be prepared to have different physical forms. For example, the d-methylphenidate prodrug may be amorphous, may have different crystalline polymorphs, or may exist in different solvation or hydration states, such as semi-hydrates, monohydrates, hydrates ($nH_2O$, when n is 0.5, 1, 2 . . . ). Such polymorphs can be produced by, e.g., using crystallization conditions to isolate a free-base and salt forms and/or by ball-milling such forms.

By varying the form of the d-methylphenidate prodrug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility. Accordingly, variation of the crystalline state of the d-methylphenidate prodrug is one of many ways in which to modulate the physical properties thereof.

A co-crystal is a multiple component crystal containing two or more non-identical molecules in which all components are solid under ambient conditions (i.e., 22° Celsius, 1 atmosphere of pressure) when in their pure form. The components comprise a target molecule (i.e., a d-methylphenidate prodrug) and a molecular co-crystal former that coexist in the co-crystal at the molecular level within a single crystal.

Co-crystals that comprise two or more molecules (co-crystal formers) Jmarsson et al., 2004) that are solids under ambient conditions represent a long-known class of compounds (see Wohler, 1844). However, co-crystals remain relatively unexplored. A Cambridge Structural Database (CSD) (Allen et al., 1993) survey reveals that co-crystals represent less than 0.5% of published crystal structures. Nevertheless, their potential impact upon pharmaceutical (e.g., nutraceutical) formulation (Vishweshwar et al., 2006; Li et al., 2006; Remenar et al., 2003; and Childs et al., 2004) and green chemistry (Anastas et al., 1998) is of topical and growing interest. In particular, the fact that all co-crystal components are solids under ambient conditions has important practical considerations because synthesis of co-crystals can be achieved via solid-state techniques (mechanochemistry)(Shan et al., 2002), and chemists can execute a degree of control over the composition of a co-crystal since they can invoke molecular recognition, especially hydrogen bonding, during the selection of co-crystal formation. Those features distinguish co-crystals from solvates which are another broad and well-known group of multiple component compounds. Solvates are much more widely characterized than co-crystals (e.g., 1652 co-crystals are reported in the CSD versus 10,575 solvates; version 5.27 (May 2006) 3D coordinates, R0.075, no ions, organics only).

It would be advantageous to have new forms of d-methylphenidate prodrugs that have improved properties. Specifically, it is desirable to identify improved forms of d-methylphenidate prodrugs that exhibit significantly improved properties including increased aqueous and/or solvent solubility and stability. Further, it is desirable to improve the processability, or preparation of pharmaceutical formulations. For example, needle-like crystal forms or habits of d-methylphenidate prodrug can cause aggregation, even in compositions where the d-methylphenidate prodrug is mixed with other substances, such that a non-uniform mixture is obtained. It is also desirable to increase or decrease the solution rate of d-methylphenidate prodrug-containing pharmaceutical compositions in water or other solvents, increase or decrease the bioavailability of orally-administered compositions, and provide a more rapid or more delayed onset to therapeutic effect. It is also desirable to have a form of the d-methylphenidate prodrug which, when administered to a subject, reaches a peak plasma level faster or slower, has a longer lasting therapeutic plasma concentration, and higher or lower overall exposure when compared to equivalent amounts of the d-methylphenidate prodrug in its presently-known form. The improved properties discussed above can be altered in a way which is most beneficial to a specific d-methylphenidate prodrug for a specific therapeutic effect.

The d-methylphenidate prodrug or conjugate of the present technology and the unconjugated methylphenidate can be either a positively charged (cationic) molecule, or a pharmaceutically acceptable anionic or cationic salt form or salt mixtures with any ratio between positive and negative components. These anionic salt forms can include, but are not limited to, for example, acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, l-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, or undecylenate. In the preferred embodiments, the anionic salt form is selected from the group consisting of chloride, hydrogen carbonate (bicarbonate), iodide, bromide, citrate, acetate, formate, salicylate, hydrogen sulfate (bisulfate), hydroxide, nitrate, hydrogen sulfite (bisulfite), propionate, benzene sulfonate, hypophosphite, phosphate, bromate, iodate, chlorate, fluoride, nitrite.

In some embodiments, the salt form of the conjugate is selected from the group consisting of chloride, hydrogen carbonate (bicarbonate), iodide, bromide, citrate, acetate, formate, salicylate, hydrogen sulfate (bisulfate), hydroxide, nitrate, hydrogen sulfite (bisulfite), propionate, benzene sulfonate, hypophosphite, phosphate, bromate, iodate, chlorate, fluoride, and nitrite. In some embodiments, the salt form of the unconjugated methylphenidate is selected from the group consisting hydrochloride, hydrobromide, hydroiodide, formate, mesylate, tartrate, salicylate, sulfate, citrate, nitrate, hydrogen sulfite, propionate, benzene sulfonate, and acetate.

The cationic salt forms can include, but are not limited to, for example, sodium, potassium, calcium, magnesium, lithium, cholinate, lysinium, or ammonium.

Without wishing to be limited to the following theory, it is believed that the prodrugs/conjugates of the present technology undergo rate determining enzyme hydrolysis in vivo, which subsequently leads to a cascade reaction resulting in rapid formation of d-methylphenidate and the respective ligands, metabolites thereof and/or derivatives thereof. The prodrug conjugates of the present technology are nontoxic or have very low toxicity at the given dose levels and are preferably known drugs, natural products, metabolites, or GRAS (Generally Recognized As Safe) compounds (e.g., preservatives, dyes, flavors, etc.) or non-toxic mimetics or derivatives thereof.

General Structures and Definitions

Abbreviations for the components of the compositions of the present technology include: MPH stands for methylphenidate; MPH.HCl stands for methylphenidate hydrochloride; Ser stands for serine; Thr stands for threonine; ′Bu stands for tert-butyl; Et stands for ethyl.

In some embodiments, the general structure of the prodrugs of d-methylphenidate of the present technology can be represented by Formula I:

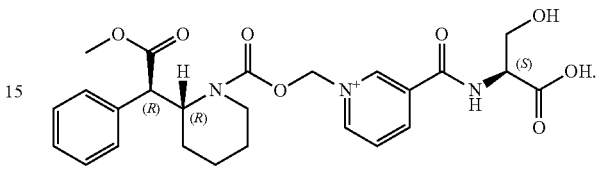

In some embodiments, the conjugate has at least two or more chiral centers. In some embodiments the conjugate has three chiral centers, such as the three chiral centers shown in Formula I.

In one embodiment, the conjugate can be an ionic salt, such as chloride, preferably d-MPH-CO$_2$CH$_2$-nicotinoyl-L-Ser chloride, having the following Formula II:

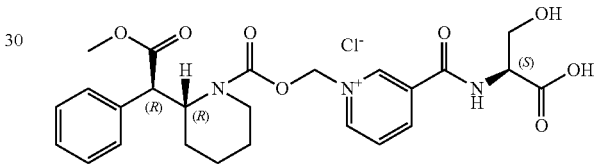

In preferred embodiments of the compositions of the present technology, the d-methylphenidate active is derived from two sources, the d-methylphenidate prodrug or conjugate and/or its pharmaceutically acceptable salts, and unconjugated methylphenidate and/or its pharmaceutically acceptable salts. In some alternative embodiments, additional sources can contribute to the d-methylphenidate active, including but not limited to, other conjugates, non-conjugated methylphenidate, methylphenidate-like stimulants, amphetamines, and amphetamine-like stimulants. The amount of d-methylphenidate active that each source contributes can vary from about 5% to about 95% by weight, based on the total weight of the d-methylphenidate active, including, but not limited to, amounts of about 10%, about 20%, about 30%, about 40%, about 50%, about 60%, about 70%, about 80%, about 90%, or any amounts in between, in increments of about 0.5%, about 1%, about 2.5%, or about 5%. In some embodiments, the d-methylphenidate conjugate contributes an amount of d-methylphenidate active that is about 60% by weight, alternatively about 70%, alternatively about 75%, alternatively about 80%, alternatively about 85%, alternatively about 90%, alternatively about 95% by weight, of the total d-methylphenidate active, or any amounts in between, in increments of about 0.5%, about 1%, about 2%, about 2.5%, or 5%; and the unconjugated methylphenidate contributes about 40% by weight, alternatively about 30%, alternatively about 25%, alternatively about 20%, alternatively about 15%, alternatively about 10%, alternatively about 5% by weight of the total d-methylphenidate active, or any amounts in between, in increments of about 0.5%, about 1%, about 2%, about 2.5%, or 5%.

It should be appreciated that the weight percentages recited above for the d-methylphenidate conjugate are expressed in terms of the total weight of the d-methylphenidate active in the composition and not the total weight of the d-methylphenidate conjugate. In some embodiments, the combination of the unconjugated methylphenidate and d-methylphenidate conjugate in the composition can be expressed in the following format: "weight of the unconjugated d-methylphenidate active/weight of the d-methylphenidate conjugate". In some specific embodiments described herein, the combination of the unconjugated d-methylphenidate active and d-methylphenidate conjugate is expressed as 8/64 mg, 12/56 mg, and 16/48 mg, where the first number (8, 12, 16) refers to the weight of the unconjugated d-methylphenidate hydrochloride active in mg, and the second number (64, 56, 48) refers to the weight of the chloride salt of the d-methylphenidate conjugate, d-MPH-$CO_2$—$CH_2$-nicotinoyl-L-Ser chloride, in mg. (See Table 11). The amount of conjugate in these embodiments is the molar equivalent to 32 mg, 28 mg and 24 mg of d-methylphenidate hydrochloride, respectively, making the molar weight ratios of unconjugated d-methylphenidate and d-methylphenidate conjugate 20%/80%, 30%/70%, and 40%/60%, respectively, based on a total molar equivalent amount of d-methylphenidate hydrochloride of 40 mg.

Administration, Formulation and Advantages

The compositions of the present technology, comprising d-methylphenidate prodrugs or conjugates and unconjugated methylphenidate, can be administered, for example, orally or rectally, and, upon administration, release the active d-methylphenidate, derivatives thereof or combinations thereof, after being hydrolyzed in the body. Not wishing to be bound by any particular theory, the nicotinoyl-L-serine ligand that is conjugated to the d-methylphenidate of the present technology comprises niacin and serine, both naturally occurring metabolites, pharmaceutically active compounds or mimetics thereof or derivatives thereof. It is believed that the prodrugs or conjugates of the present technology can be easily recognized by physiological systems resulting in hydrolysis and release of d-methylphenidate.

The prodrugs of the present technology are believed to have no or limited pharmacological activity themselves and consequently may follow a metabolic pathway that differs from the parent drug (i.e., methylphenidate).

It has been surprisingly found that in some embodiments of the present technology, the compositions comprising prodrugs or conjugates of d-methylphenidate and unconjugated methylphenidate provide a controlled-release or extended-release profile as compared with unconjugated d-methylphenidate. In some embodiments, the prodrugs or conjugates of the present technology surprisingly provide increased water solubility as compared with unconjugated d-methylphenidate. In some embodiments, the prodrugs or conjugates of the present technology have at least about 1.2 times or at least about 1.5 times the water solubility of unconjugated d-methylphenidate. In some embodiments, the prodrugs or compositions of the present technology have at least about 1.7, at least about 2.0, at least about 2.2, at least about 2.5, at least about 3.0, at least about 4.0 or at least about 5 times the water solubility of unconjugated d-methylphenidate, and include any multiples in between or above that have water solubility greater than unconjugated d-methylphenidate. Not to be bound by any particular theory, the increase in water solubility may allow for the conjugate to be formed into certain dosage forms at higher concentrations, dosage strengths or higher dose loading capacities than unconjugated d-methylphenidate. In some embodiments, these dosage forms include, but are not limited to, forms that require water solubility, including, but not limited to, liquids and/or oral thin films or strips.

In some embodiments, the composition of the present technology, comprising (a) the prodrug or conjugate and/or its pharmaceutically acceptable salts, and (b) unconjugated methylphenidate and/or its pharmaceutically acceptable salts, is also believed to unexpectedly exhibit both immediate-release (during the time period before $T_{max}$) and extended-release (during the time period after $T_{max}$) PK profiles as a single daily dosage form when compared to unmodified d-methylphenidate. Further, it is believed that the conjugate is capable of being enzymatically or hydrolytically activated or converted into the active form. Further, the composition described herein is believed to release d-methylphenidate, its active metabolites and/or derivatives and their combination, resulting in improved PK profile outcome and/or exposure to d-methylphenidate, its active metabolites and/or derivatives when compared to free or unconjugated d-methylphenidate at equimolar doses. In some embodiments, the composition of the present technology, comprising the prodrug and/or its pharmaceutically acceptable salts and unconjugated methylphenidate and/or its pharmaceutically acceptable salts, provides plasma concentrations of d-methylphenidate released from the composition that are increased from about 0 to about 1 hour following oral administration in a human subject when compared to unconjugated d-methylphenidate released from Concerta®. In other embodiments, plasma concentrations of d-methylphenidate released from the composition are increased from 0 to about 2 hours, 0 to about 3 hours, 0 to about 4 hours, or 0 to about 0.5 hours, following oral administration of a human subject. Time 0 hours as used herein refers to the time of administration.

Not to be bound by any particular theory, it is believed that this may allow for administration of a lower dose with equal or improved therapeutic effect, but with fewer and/or less severe side effects when compared to unmodified d-methylphenidate, thereby improving the safety profile of the drug, yet while achieving patient therapeutic efficacy. Common side effects of d-methylphenidate are nervousness, agitation, anxiety, and insomnia or drowsiness. Other common side effects are abdominal pain, weight loss, hypersensitivity, nausea, dizziness, palpitation, headache, dyskinesia, blood pressure, pulse changes, tachycardia, angina, and cardiac arrhythmia.

In one embodiment, the compositions comprising the at least one prodrug or conjugate of the present technology would alter the metabolic profile of d-methylphenidate, derivatives thereof or combinations thereof, by, for example, changing the amounts and/or ratio of d-methylphenidate and its metabolites, such as the inactive ritalinic acid within the body. The prodrug or conjugate of the present technology, for example, would decrease the number and/or the amount of metabolites, including active, inactive, toxic or non-toxic metabolites, produced by unconjugated d-methylphenidate. Not wishing to be bound by any particular theory, it is believed that this change in metabolism may potentially alleviate certain side effects of any metabolite(s), as well as potentially improve upon the safety profile of d-methylphenidate. In some embodiments, compositions of the present technology may reduce the overall exposure to ritalinic acid by about 25% up to about 75% as compared to the amount of ritalinic acid produced by an equimolar amount of unconjugated d-methylphenidate. In some embodiments, the overall exposure to ritalinic acid may be reduced by about 30%, alternatively about 35%, alternatively about 40%, alternatively about 45%, alternatively about 50%, alternatively about 55%, alternatively about 60%, alternatively about 65%, alternatively about 70% as compared to an equimolar amount of unconjugated d-methylphenidate.

In another embodiment, the compositions comprising the prodrugs or conjugates of the present technology and unconjugated methylphenidate would unexpectedly produce reduced interpatient variability of d-methylphenidate plasma concentrations. Not to be bound by any particular theory, it can be assumed that the reduction of interpatient variability of d-methylphenidate plasma concentrations may be due to either increased bioavailability or a modified metabolic pathway or a combination of both. In another embodiment, the compositions comprising the prodrug of the present technology and unconjugated methylphenidate would alter the metabolic pathway of the released d-methylphenidate when compared to unmodified d-methylphenidate. It is believed that in such an embodiment, the metabolism of the prodrug may decrease interpatient variability and/or reduce side effects associated with unconjugated d-methylphenidate or any of its metabolites.

In a further embodiment, the at least one prodrug or conjugate of the present technology can comprise racemic d- and l-methylphenidate which is preferably hydrolyzed to d-methylphenidate in the body and thus delivers more of the therapeutically active d-isomer. Wishing not to be bound by any particular theory, this may reduce potential side effects caused by l-methylphenidate and/or its metabolites.

In some embodiments, the compositions of the present technology are believed to exhibit an improved immediate-release and/or extended-release PK profile, compared to unconjugated d-methylphenidate when administered orally at equimolar doses. In some embodiments, the compositions of the present technology are believed to surprisingly generate both a $C_{max}$ and an AUC value of released d-methylphenidate that exhibits an improved immediate-release or extended-release PK profile, as a single daily dosage form, when compared to unconjugated d-methylphenidate of Concerta® when administered orally at equimolar doses.

In some embodiments, the compositions of the present technology are believed to unexpectedly generate a $T_{max}$ value of released d-methylphenidate that is longer than the $T_{max}$ value produced by unconjugated d-methylphenidate when administered orally at equimolar doses.

In some embodiments, the AUC is about 50% (or smaller) of the AUC of unconjugated d-methylphenidate, when administered intranasally or intravenously at equimolar doses, for example about 50% to about 0.1%, alternatively from about 25% to about 0.1%, alternatively from about 50% to about 1%, including, but not limited to, about 50%, about 40%, about 30%, about 20%, about 10%, about 1% or any amounts in between, in increments of about 0.5%, about 1%, about 2%, about 2.5%, about 5% or about 10%.

D-methylphenidate has rewarding properties and is prone to substance abuse because of its pharmacological similarity to cocaine and amphetamine. Oral abuse has been reported to lead to hallucinations, paranoia, euphoria, and delusional disorder. Oral abuse may subsequently escalate to intravenous and intranasal abuse. Euphoria has been reported after intravenous administration of d-methylphenidate. When administered intranasally the effect is found to be similar to intranasal use of amphetamines.

The compounds, prodrugs, compositions and/or methods of the present technology are believed to provide reduced potential for overdose, reduced potential for abuse and/or improve the characteristics of d-methylphenidate, derivatives thereof or combinations thereof with regard to toxicities or suboptimal release profiles. The prodrugs of the present technology may preferably have no or a substantially decreased pharmacological activity when administered through injection or intranasal routes of administration. However, they remain orally bioavailable. Without wishing to be limited to the below theory, it is believed that overdose protection may occur due to the conjugates being exposed to different enzymes and/or metabolic pathways after oral administration whereby the conjugate of the present technology is exposed to the gut and first-pass metabolism as opposed to exposure to enzymes in the circulation or mucosal membranes in the nose, which limits the ability of the d-methylphenidate, derivatives thereof or combinations thereof, from being released from the conjugate. Therefore, abuse resistance is provided by limiting the effectiveness of alternative routes of administration. Again, not wishing to be bound by any particular theory, the route-specific bioavailability can be a result of differential hydrolysis of the chemical linkage (i.e., a covalent linkage) following oral, intranasal, or intravenous administration. The prodrugs of the present technology are envisioned to not hydrolyze or to hydrolyze at a reduced rate or to a limited extent via non-oral routes. As a result, they are believed to not generate high plasma or blood concentrations of released d-methylphenidate when injected or snorted compared to free d-methylphenidate administered through these routes.

It is contemplated that the prodrugs of the present technology are resistant to abuse by parenteral routes of administration, such as intravenous "shooting," or intranasal "snorting," that are often employed during illicit use. For example, release of d-methylphenidate, derivatives thereof or combinations thereof, is reduced when the composition of the present technology is delivered by parenteral routes. Further, the conjugates of the present technology, since they are believed to include covalently bound d-methylphenidate, derivatives thereof or combinations thereof, are not able to be physically manipulated to release the d-methylphenidate, derivatives thereof or combinations thereof, from the conjugated d-methylphenidate, derivatives thereof or combinations thereof, by methods, for example, of grinding up or crushing of solid forms. The conjugates of the present technology are also contemplated to exhibit resistance to chemical hydrolysis under conditions a potential drug abuser may apply to "extract" the active portion of the molecule, for example, by boiling, or acidic or basic solution treatment of the conjugate. Some compositions containing prodrugs or conjugates of the present technology preferably have no or a substantially decreased pharmacological activity when administered through injection or intranasal routes of administration. However, they remain orally bioavailable.

For example, the prodrug or conjugate of the present technology is contemplated to surprisingly maintain its effectiveness and abuse resistance following the crushing of the tablet, capsule or other oral dosage form utilized to deliver the therapeutic component (i.e., active ingredient/drug) which is believed to be due to the inherent release profile being a property of the composition not formulation. In contrast, conventional extended release formulations used to control the release of d-methylphenidate are subject to release of up to the entire d-methylphenidate content immediately following crushing. When the content of the crushed tablet is injected or snorted, the large dose of d-methylphenidate produces the "rush" effect sought by addicts. In some embodiments, the compositions of the present technology potentially reduce drug liking. Without being bound by theory, since some of the d-methylphenidate is covalently bound in the conjugate, there is a slower of release of d-methylphenidate compared to an equimolar dose of unconjugated d-methylphenidate, which could lead to a reduced drug liking outcome.

The present technology provides a stimulant based treatment modality and dosage form for certain disorders requiring the stimulation of the CNS such as, attention-deficit hyperactivity disorder (ADHD), attention deficit disorder (ADD)(technically ADHD, Predominantly Inattentive Type), autistic spectrum disorder, autism, Asperger's disorder, pervasive developmental disorder, sleep disorder, obesity, depression, bipolar disorder, eating disorder, binge eating disorder, chronic fatigue syndrome, schizophrenia, major depressive disorder, central hypersomnolence disorders narcolepsy, excessive daytime sleepiness (EDS), cocaine dependence, stimulant dependence, or autistic spectrum disorder. In a preferred embodiment, the at least one prodrug or composition of the present technology is used to treat a sleep disorder, chronic fatigue syndrome, central hypersomnolence disorders narcolepsy, or excessive daytime sleepiness (EDS).

In some embodiments, the compositions of the present technology comprising at least one prodrug or conjugate of d-methylphenidate and unconjugated methylphenidate can be used in one or more methods of treating a subject or patient (human or animal, preferably mammal) having at least one disease, disorder or condition requiring stimulation of the central nervous system of one or more subjects, comprising orally administering a pharmaceutically and/or therapeutically effective amount of the at least one composition.

In some embodiments, the composition of the present technology can be used in one or more methods of treating one or more subjects or patients (human or animal, preferably mammal) having at least one disease, disorder or condition mediated by controlling, preventing, limiting, or inhibiting neurotransmitter uptake/re-uptake or hormone uptake/re-uptake comprising administering to at least one subject a pharmaceutically and/or therapeutically effective amount of the composition. In some embodiments, the neurotransmitter is serotonin, dopamine or norepinephrine. In some embodiments, the hormone is catecholamine.

At least some compositions of the present technology comprising (a) the prodrugs of methylphenidate, and/or their pharmaceutically acceptable salts and (b) unconjugated methylphenidate and/or its pharmaceutically acceptable salts, can also be used for treating stimulant (cocaine, methamphetamine, among others) abuse and addiction, for improving battle field alertness, and/or for combating fatigue.

The compositions of the present technology can be formulated into dosage forms that include but are not limited to sublingual, gummy, chewable tablet, rapidly dissolving tablet, tablet, capsule, caplet, troche, lozenge, powder, suspension, syrup, solution, oral thin film (OTF), oral strip, rectal film, or suppository. In some embodiments, the dosage forms are to be administered orally. Preferred oral administration forms are capsule, tablet, solutions and OTF. Suitable dosing vehicles of the present technology include, but are not limited to, water, phosphate buffered saline (PBS), 10% Tween in water, and 50% PEG-400 in water.

Solid dosage forms can optionally include one or more of the following types of excipients: antiadherents, binders, coatings, disintegrants, gel forming agents, fillers, flavors and colors, glidants, lubricants, preservatives, sorbents and sweeteners.

Oral formulations of the present technology can also be included in a solution, a suspension or a slurry in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a subject who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The individual units so formed are then dried to constant weight.

Chewable tablets, for example, may be prepared by mixing the formulations with excipients designed to form a relatively soft, flavored, tablet dosage form that is intended to be chewed rather than swallowed. Conventional tablet machinery and procedures, for example, direct compression and granulation, i.e., or slugging, before compression, can be utilized. Those individuals involved in pharmaceutical solid dosage form production are versed in the processes and the machinery used, as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with one or more excipients intended to add binding qualities to disintegration qualities. The mixture is either directly compressed or granulated and then compressed using methods and machinery known to those in the industry. The resultant compressed tablet dosage units are then packaged according to market need, for example, in unit dose, rolls, bulk bottles, blister packs, etc.

The present technology contemplates that the compositions of the present technology can be formulated into formulations or co-formulations that may further comprise one or more additional components. For example, such formulations can include biologically-acceptable carriers which may be prepared from a wide range of materials. Without being limited to, such materials include diluents, binders and adhesives, lubricants, gel forming agents, plasticizers, disintegrants, colorants, bulking substances, surfactants, flavorings, sweeteners and miscellaneous materials such as buffers and adsorbents in order to prepare a particular medicated formulation or co-formulation. In one embodiment, the composition of the present technology comprises from about 10% to about 60% by weight d-methylphenidate conjugate, or a salt thereof, from about 2% to about 15% by weight unconjugated d-methylphenidate, or a salt thereof, and one or more additional components to total 100% by weight, based on the total weight of the formulation. The one or more additional components may include, but are not limited to, diluents, lubricants, disintegrants, fillers, and glidants.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons working in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

It should be understood that in addition to the ingredients particularly mentioned above, the formulations of the present technology can include other suitable agents, such as flavoring agents, preservatives, and antioxidants, among others. Such antioxidants would be food acceptable and could include, for example, vitamin E, carotene, BHT or other antioxidants. Suitable flavoring agents and preservatives are known to one of skill in the art.

Other compounds which may be included by admixture are, for example, medically inert ingredients, e.g., solid and liquid diluents, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate, hydrogenated oils, sodium stearyl fumarate, and/or polyethylene glycols; gelling agents such as colloidal clays, polyethylene oxide, hydroxypropyl methyl cellulose, or carbomers; thickening agents such as gum tragacanth or sodium alginate, binding agents such as starches, arabic gums, gelatin, methylcellulose, carboxymethylcellulose or polyvinylpyrrolidone (povidone); disintegrating agents such as starch, alginic acid, alginates, crospovidone, or sodium starch glycolate; effervescing mixtures; dyestuff; sweeteners; wetting agents such as lecithin, polysorbates, poloxamer, sorbitan monoesters, glyceryl monooleates, or laurylsulfates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular a syrup for diabetic subjects can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

The ingredients mentioned herein are not intended to be exhaustive, and one of skill in the art will be able to formulate suitable compositions using known or to be known ingredients.

Methylphenidate is being marketed in numerous dosage forms and at various dosage strengths either as a racemic mixture of d- and l-threo-methylphenidate or as a single d-threo-isomer (Table 1). Recommended daily doses depend on the dosage form, active ingredient (single isomer or racemic mixture) and individual subject or patient titration.

TABLE 1

Examples of marketed methylphenidate dosage forms and dosage strengths.

| Active Ingredient | Dosage Form | Dosage Strength(s) | Proprietary Name(s) |
|---|---|---|---|
| methylphenidate hydrochloride | instant release tablet | 5, 10, 20 mg | Ritalin ® |
| dexmethylphenidate hydrochloride | instant release tablet | 2.5, 5, 10 mg | Focalin ® |
| methylphenidate hydrochloride | extended release tablet | 10, 20 mg | Methylin ER ®, Metadate ER ® |
| methylphenidate hydrochloride | extended release tablet | 10, 18, 20, 27, 36, 54 mg | Concerta ® |
| methylphenidate hydrochloride | chewable tablet | 2.5, 5, 10 mg | Methylin |
| methylphenidate hydrochloride | extended release capsules | 10, 20, 30, 40 mg | Ritalin LA ® |
| methylphenidate hydrochloride | extended release capsules | 10, 20, 30, 40, 50, 60 mg | Metadate CD ® |
| dexmethylphenidate hydrochloride | extended release capsules | 5, 10, 15, 20, 30, 40 mg | Focalin XR ® |
| methylphenidate | transdermal patch | 10, 15, 20, 30 mg/9 h | Daytrana ® |
| methylphenidate hydrochloride | oral solution | 5, 10 mg/5 mL | Methylin ® |

In some embodiments, doses of the compositions of the present technology, comprising the prodrug and/or its pharmaceutically acceptable salts, and unconjugated methylphenidate and/or its pharmaceutically acceptable salts, can be higher or lower than doses of unconjugated methylphenidate depending on their molecular weight, the respective weight-percentage of methylphenidate as part of the whole conjugate or conjugate salt, and their bioavailability (with respect to released methylphenidate). Therefore dosages may be higher or lower than the dosages of free methylphenidate. Dosages can be calculated based on the strengths of dosages of methylphenidate hydrochloride which range between, for example, but not limited to, about 0.5 mg and about 200 mg per dose. Dose conversion from methylphenidate hydrochloride to methylphenidate prodrug can be performed using the following formula:

$$\text{dose(MPH prodrug)} = f_{BA} \times \text{dose(MPH hydrochloride)} \times \frac{\text{MW(MPH prodrug)}}{269.77 \frac{g}{mol}}$$

MPH=methylphenidate
MW=molecular weight
$f_{BA}$=correction factor accounting for differences in bioavailability between unmodified methylphenidate and prodrugs of the present technology. This correction factor is specific for each prodrug.

In further embodiments, weight amounts or doses of unconjugated or conjugated d-methylphenidate, and any of their salt forms can be expressed as the molar equivalent weight amount or dose of any other compound or a salt thereof. For example, a dose of d-MPH-CO$_2$CH$_2$-nicotinoyl-L-Ser chloride can alternatively be expressed as an equimolar dose of d-MPH-CO$_2$CH$_2$-nicotinoyl-L-Ser, d-methylphenidate, or d-methylphenidate hydrochloride. Other examples include, but are not limited to, a dose of d-methylphenidate hydrochloride can alternatively be expressed as an equimolar dose of d-methylphenidate, d-MPH-CO$_2$CH$_2$-nicotinoyl-L-Ser, or d-MPH-CO$_2$CH$_2$-nicotinoyl-L-Ser chloride. The general formula to calculate the molar equivalent dose of Compound 2 from the dose of Compound 1 is as follows:

$$\text{Dose(Compound 2)} = \text{Dose(Compound 1)} \times \frac{\text{MW(Compound 2)}}{\text{MW(Compound 1)}}$$

Dose(Compound 1)=dose of Compound 1 (in mass units)
Dose(Compound 1)=dose of Compound 1 (in mass units)
MW(Compound 1)=molecular weight of Compound 1
MW(Compound 2)=molecular weight of Compound 2

The following table lists the molecular weights of unconjugated d-methylphenidate and a salt form thereof, and an example of a conjugated d-methylphenidate and a salt form thereof.

| Compound | Molecular Weight (g/mol) |
|---|---|
| d-MPH-CO$_2$CH$_2$-nicotinoyl-L-Ser | 500.53 |
| d-MPH-CO$_2$CH$_2$-nicotinoyl-L-Ser chloride | 535.98 |
| d-methylphenidate | 233.31 |
| d-methylphenidate hydrochloride | 269.77 |

In some embodiments, suitable dosages of the compositions of the present technology include, but are not limited to, formulations including an amount of conjugated d-methylphenidate and unconjugated methylphenidate equimolar to an amount of unconjugated d-methylphenidate from about 0.1 mg or higher, alternatively about 0.5 mg or higher, alternatively from about 1.0 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher, alternatively 120 mg or higher, alternatively 200 mg or higher, alternatively 300 mg or higher, and include any additional increments thereof, for example, about 0.1, about 0.2, about 0.25, about 0.3, about 0.4, about 0.5, about 0.6, about 0.7, about 0.75, about 0.8, about 0.9 or about 1.0 mg and multiplied factors thereof, (e.g., about ×1, about ×2, about ×2.5, about ×5, about ×10, about ×100, etc.). The amount of conjugated d-methylphenidate and unconjugated methylphenidate in the compositions of the present technology can vary from about 5% to about 95% by weight, based on the total weight of the d-methylphenidate active, including, but not limited to, amounts of about 10%, about 20%, about 30%, about 40%, about 50%, about 60%, about 70%, about 80%, about 90%, or any amounts in between, in increments of about 0.5%, about 1%, about 2.5%, or about 5%. In preferred embodiments, the amount of d-methylphenidate contributed by the conjugated d-methylphenidate ranges from about 60% to about 95% by weight, based on the total weight of the d-methylphenidate active, and the amount of unconjugated methylphenidate ranges from about 5% to about 40% by weight based on the total weight of the d-methylphenidate active.

It is contemplated that daily dosing regimens for some embodiments of the compositions of the present technology include, but are not limited to, an amount of d-methylphenidate that is molar equivalent to a dose of d-methylphenidate hydrochloride from about 0.1 mg to about 300 mg per day, about 0.5 mg to about 300 mg per day, alternatively about 1 mg to about 100 mg per day, alternatively about 5 mg to about 80 mg per day, alternatively about 10 mg to about 40 mg per day, alternatively about 10 mg to 200 mg per day, alternatively about 20 mg to about 120 mg per day, alternatively about 30 mg to about 100 mg per day, alternatively about 40 mg to about 80 mg per day, alternatively about 50 mg to about 70 mg per day, alternatively about 20 mg to about 40 mg per day, alternatively about 20 mg to about 60 mg per day, alternatively about 10 mg to about 50 mg per day, alternatively about 20 mg per day, alternatively about 40 mg, alternatively about 60 mg per day, alternatively 80 mg per day, alternatively 100 mg per day, alternatively 120 mg per day.

It is also contemplated that some embodiments of the compositions of the present technology would have a dosing regimen of one time a day, alternatively two times a day or less, alternatively four times a day or less. It is contemplated that some of the formulations of the present technology would be provided in a unit dose form. "Unit dose form" here means a single entity of a solid therapeutic dosage form (e.g., 1 capsule, 1 tablet) or a single volume dispensed from a non-solid dosage form (e.g., 5 mL of a liquid or syrup). Such a unit dose form can be from about 0.5 mg to about 400 mg per day, alternatively from about 0.1 mg to about 300 mg per day, about 0.5 mg to about 300 mg per day, alternatively about 1 mg to about 100 mg per day, alternatively about 5 mg to about 80 mg per day, alternatively about 10 mg to about 40 mg per day, alternatively about 10 mg to 200 mg per day, alternatively about 20 mg to about 120 mg per day, alternatively about 30 mg to about 100 mg per day, alternatively about 40 mg to about 80 mg per day, alternatively about 50 mg to about 70 mg per day, alternatively about 20 mg to about 40 mg per day, alternatively about 20 mg to about 60 mg per day, alternatively about 10 mg to about 50 mg per day, alternatively about 20 mg per day, alternatively about 40 mg per day, alternatively about 60 mg per day, alternatively 80 mg per day, alternatively 100 mg per day, alternatively 120 mg per day. The present technology also includes dosage formulations including currently approved formulations of d-methylphenidate (See Table 1), where the dosage can be calculated using the above-noted formula determined by the amount of d-methylphenidate hydrochloride. The present technology provides for dosage forms formulated as a single therapy or as a combination therapy.

In some embodiments, the compositions of the present technology can further comprise or be combined with one or more active ingredient(s), including but not limited to aripiprazole, atomoxetine, baclofen, clonidine, desipramine, dihydrotetrabenazine, guanfacine, haloperidol, levetiracetam, mecamylamine, etoclopramide, olanzapine, ondansetron, pergolide, pimozide, pramipexole, risperidone, selegiline, sulpiride, tetrabenazine, topiramate, ziprasidone, and ziprasidone.

In some embodiments, suitable dosages of the compositions of the present technology, comprising conjugated d-methylphenidate-CO$_2$CH$_2$_nicotinoyl-L-Ser chloride prodrugs and unconjugated methylphenidate and/or pharmaceutically acceptable salts thereof, include, but are not limited to, formulations including an amount of conjugated d-methylphenidate and unconjugated d-methylphenidate equimolar to an amount of unconjugated d-methylphenidate from about 0.5 mg or higher, alternatively from about 1.0 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher, alternatively 120 mg or higher, alternatively 200 mg or higher, alternatively 300 mg or higher, and include any additional increments thereof, for example, about 0.1, about 0.2, about 0.25, about 0.3, about 0.4, about 0.5, about 0.6, about 0.7, about 0.75, about 0.8, about 0.9 or about 1.0 mg and multiplied factors thereof, (e.g., about ×1, about ×2, about ×2.5, about ×5, about ×10, about ×100, etc). It is contemplated that daily dosing regimens for some embodiments of the compositions comprising the conjugated d-methylphenidate of the present technology and unconjugated d-methylphenidate include, but are not limited to, an amount of d-methylphenidate that is molar equivalent to a dose of d-methylphenidate hydrochloride from about 0.5 mg to about 300 mg per day, alternatively about 1 mg to about 100 mg per day, alternatively about 5 mg to about 80 mg per day, alternatively about 10 mg to about 40 mg per day, alternatively about 10 mg to 200 mg per day, alternatively about 20 mg to about 120 mg per day, alternatively about 30 mg to about 100 mg per day, alternatively about 40 mg to about 80 mg per day, alternatively about 50 mg to about 70 mg per day, alternatively about 20 mg to about 40 mg per day, alternatively about 20 mg to about 60 mg per day, alternatively about 10 mg to about 50 mg per day, alternatively about 20 mg per day, alternatively about 40 mg per day, alternatively about 60 mg per day, alternatively about 80 mg per day, alternatively about 100 mg per day, alternatively about 120 mg per day.

It is also contemplated that some embodiments of the compositions of the present technology, comprising (a) conjugated d-methylphenidate-CO$_2$CH$_2$-nicotinoyl-L-Ser and/or pharmaceutically acceptable salts thereof, and (b) unconjugated methylphenidate and/or pharmaceutically acceptable salts thereof, would have a dosing regimen of one time a day, alternatively two times a day or less, alternatively four times a day or less. It is contemplated that some of the formulations of the present technology would be provided in a unit dose form. Such a unit dose form can be from about 0.5 mg to about 400 mg per day, alternatively from about 0.1 mg to about 300 mg per day, about 0.5 mg to about 300 mg per day, alternatively about 1 mg to about 100 mg per day, alternatively about 5 mg to about 80 mg per day, alternatively about 10 mg to about 40 mg per day, alternatively about 10 mg to 200 mg per day, alternatively about 20 mg to about 120 mg per day, alternatively about 30 mg to about 100 mg per day, alternatively about 40 mg to about 80 mg per day, alternatively about 50 mg to about 70 mg per day, alternatively about 20 mg to about 40 mg per day, alternatively about 20 mg to about 60 mg per day, alternatively about 10 mg to about 50 mg per day, alternatively about 20 mg per day, alternatively about 40 mg per day, alternatively about 60 mg per day, alternatively about 80 mg per day, alternatively about 100 mg per day, alternatively about 120 mg per day. The present technology also includes dosage formulations including currently approved formulations of d-methylphenidate (See Table 1), where the dosage can be calculated using the above-noted formula determined by the amount of d-methylphenidate hydrochloride. The present technology provides for dosage forms formulated as a single therapy or as a combination therapy.

In some embodiments, the compositions comprising conjugates of d-methylphenidate and nicotinoyl-L-Serine to form prodrugs have one or more advantages, including, but not limited to, reduced or improved side effect profile, formation of less potentially toxic metabolites, formation of less inactive metabolites, improved water solubility, reduced drug abuse potential and/or reduced interpatient variability in plasma concentrations as compared to unconjugated d-methylphenidate.

Synthetic Schemes

General synthetic schemes for preparing prodrugs of d-methylphenidate are disclosed in U.S. Pat. No. 9,079,928, which is herein incorporated by reference. One or more protecting groups may be attached to any additional reactive functional groups that may interfere with the coupling to d-methylphenidate. Any suitable protecting group may be used depending on the type of functional group and reaction conditions. Some protecting group suitable for use in the present technology include, but are not limited to, acetyl (Ac), tert-butyl (tBu), tert-butyoxycarbonyl (Boc), benzyloxycarbonyl (Cbz), p-methoxybenzylcarbonyl (Moz), 9-fluorenylmethyloxycarbonyl (Fmoc), benzyl (Bn), p-methoxybenzyl (PMB), 3,4 dimethoxybenzyl (DMPM), p-methozyphenyl (PMP), tosyl (Ts), or amides (like acetamides, phthalimides, and the like).

In other embodiments, a base may be required at any step in the synthetic scheme of preparing the prodrug of d-methylphenidate. Suitable bases include, but are not limited to, 4-methylmorpholine (NMM), 4-(dimethylamino)pyridine (DMAP), N,N-diisopropylethylamine (DIPEA), lithium bis (trimethylsilyl)amide, lithium diisopropylamide (LDA), any alkali metal tert.-butoxide (e.g., potassium tert.-butoxide), any alkali metal hydride (e.g., sodium hydride), any alkali metal alkoxide (e.g., sodium methoxide), triethylamine (Et$_3$N or TEA) or any other tertiary amine.

Suitable solvents that can be used for any reaction at any step in the synthetic scheme of preparing the prodrug of d-methylphenidate include, but are not limited to, acetone, acetonitrile, butanol, chloroform, dichloromethane (DCM), dimethylformamide (DMF), dimethylsulfoxide (DMSO), dioxane, ethanol, ethyl acetate, diethyl ether, heptane, hexane, methanol, methyl tert.-butyl ether (MTBE), isopropanol (IPA), isopropyl acetate (IPAc), diisopropyl ether, tetrahydrofuran, toluene, xylene or water.

In some embodiments, an acid may be used to remove certain protecting groups. Suitable acids include, but are not limited to, hydrochloric acid, hydrobromic acid, hydrofluoric acid, hydroiodic acid, sulfuric acid, phosphoric acid, trifluoroacetic acid, acetic acid, citric acid, methanesulfonic acid, p-toluenesulfonic acid and nitric acid. For certain other protecting groups, a catalytic hydrogenation may be used, e.g., palladium on charcoal in the presence of hydrogen gas.

In some embodiments, an anion exchange medium, anion exchange resin, strong or weak anion exchanger including but not limited to Dowex® 1×8 chloride (available from Dow Chemical Co, Midland, Mich.) may be used to replace anionic counter ions of the cationic conjugate with a specific new counter anion such as a chloride ion.

In some embodiments, the prodrug is hydrophilic and thus more water soluble than the unconjugated d-methylphenidate.

A synthetic scheme for preparing d-MPH-CO₂CH₂-nicotinoyl-L-Ser is as follows:

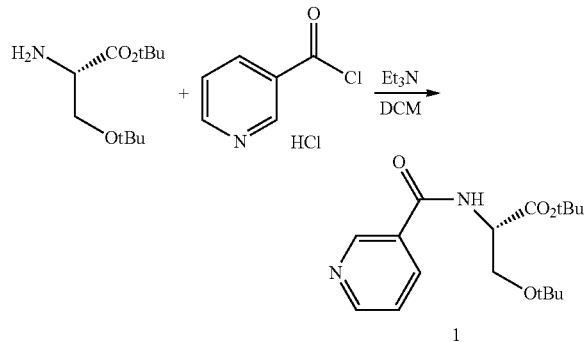

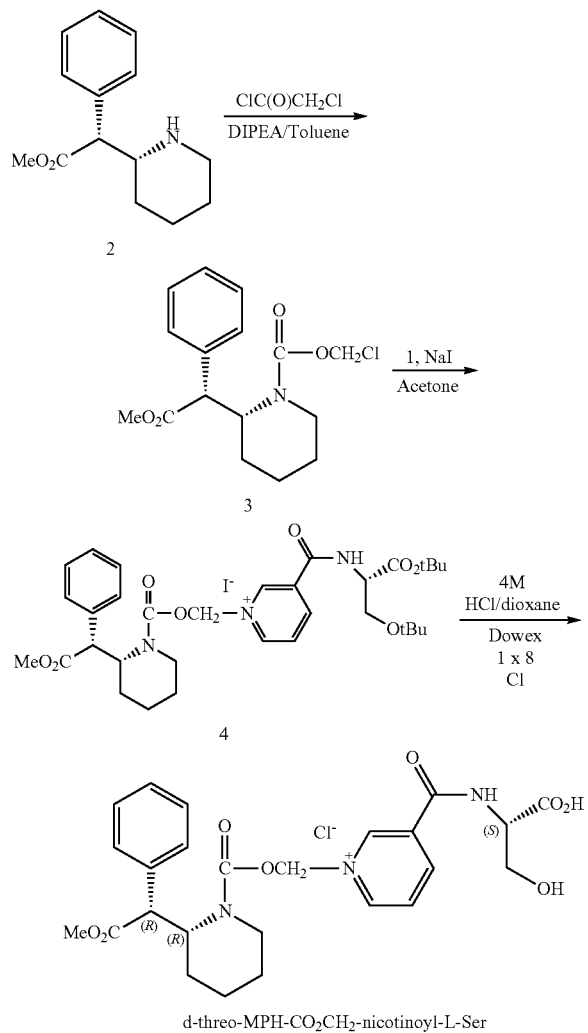

1). Nicotinoyl-Ser(tBu)OtBu 1:

To O-tert-Butyl-L-Serine tert-butyl ester (H-Ser(tBu)OtBu, 5.305 g, 23.17 mmol) in DCM (250 mL) was added Et₃N (5.329 g, 53.29 mmol, 2.3 eq.). The flask was cooled in an ice-water bath (~5° C.). Nicotinoyl chloride hydrochloride (4.331 g, 24.33 mmol, 1.05 eq.) was added in 7 portions over 1 hr. After adding, the water bath was removed and the reaction was stirred for another hour. 60 mL of 5% NH₄Cl was added to quench the reaction. The DCM layer was further washed with brine (60 mL) and dried over Na₂SO₄. The product was purified by column (hexanes:ethyl acetate, 1:1.3). 6.977 g of syrup was obtained. The yield was 93.4% and the purity was 98%.

(2R,2'R)-(+)-Methylphenidate hydrochloride 2 (d-threo isomer):

2 was made by resolution of d-threo-Methylphenidate hydrochloride 2 with O, O'-dibenzoyl-D-(+)-tartaric acid according to the method developed by Mahavir Prashad (Tetrahedron: Asymmetry 1999, 10, 3111). The yield was 40-42%.

(R)-Chloromethyl 2-((R)-2-methoxy-2-oxo-1-phenylethyl)piperidine-1-carboxylate 3:

d-(+)-threo Methylphenidate hydrochloride (MPH.HCl) 2 (8.093 g, 30 mmol) in toluene (150 mL) was added DIPEA (12.4 mL, 75 mmol) under ice-water bath (–5° C.). Then chloromethyl chloroformate (5.029 g, 39 mmol) in toluene (50 mL) was added over 20 min at about 5° C. After adding, the reaction was stirred at about 5-10° C. for 40 min. 5% NH₄Cl (50 mL) was added to quench the reaction. The toluene layer was separated, washed with brine (50 mL) and dried over Na₂SO₄. Solvent was evaporated to give crude 3, which was purified by silica gel chromatography column (hexanes:ethyl acetate, 3:1) to give 9.833 g of syrup (solidified when stored in freezer) and the yield was quantitative.

4). 3-((S)-1-carboxy-2-hydroxyethylcarbamoyl)-1-(((R)-2-(2-(R)-methoxy-2-oxo-1-phenylethyl)piperidine-1-carbonyloxy)methyl)pyridium chloride d-threo-MPH-CO₂CH₂-nicotinoyl-L-Ser:

Nicotinoyl-Ser(tBu)OtBu 1 (0.322 g, 1 mmol) and carbamate 3 (0.355 g, 1.09 mmol, 1.09 eq.) were dissolved in acetone (10 mL). Then NaI (0.161 g, 1.08 mmol, 1.08 eq.) was added. The reaction was refluxed for 1.5 hr. Upon cooling to room temperature, the reaction mixture was kept at room temperature for 2 hr. The solid (NaCl) was filtered off. The filtrate was concentrated and dried over vacuum for 1 hr to give amorphous solid 0.778 g. The solid in 4 M HCl/dioxane (5 mL) was stirred at room temperature for 2 hr.

Solvent was evaporated and the remaining was co-evaporated with DCM (2 times 6 mL), and then dried over vacuum for 1 hr. to give amorphous solid 0.667 g. It was dissolved in 10 mL of ethanol and treated with resin twice (2 times 1 g, Dowex 1×8, 200-400, Cl form, prewashed with water and ethanol, wet). The filtrate after resin treatment was concentrated and dried over vacuum to give amorphous solid 0.617 g. The solid was dissolved in 10 mL of IPA with heating and then 5 mL of IPAc was added. Crystals formed gradually. After 3 hr., solid was collected and washed with IPA/IPAc (2:1, 3 times 1 mL), dried over vacuum. 437 mg of white solid (d-MPH-CO₂CH₂-nicotinoyl-L-Ser chloride) was obtained. The yield was 81.5% and the purity was 97.6%.

Preparation of cationic species of d-MPH-CO₂CH₂-nicotinoyl-L-Ser:

The chloride salt of d-MPH-CO₂CH₂-nicotinoyl-L-Ser is dissolved in water. The resulting solution contains free d-MPH-CO₂CH₂-nicotinoyl-L-Ser in cationic form.

A synthetic scheme for preparing d-MPH-CO₂CH₂-nicotinoyl-L-Thr is as follows:

Scheme 1: Synthesis of nicotinoyl-Thr(tBu)OtBu 5

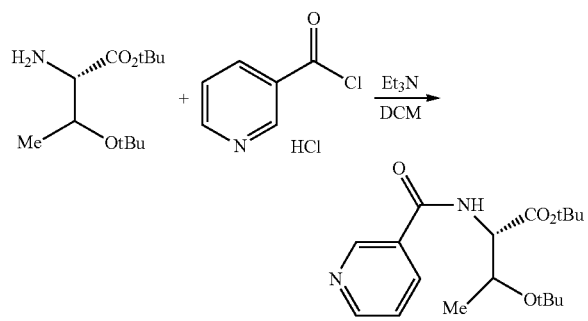

Scheme 2: Synthesis of threonine analogue of d-MPH-CO₂CH₂-nicotinoyl-L-Thr.

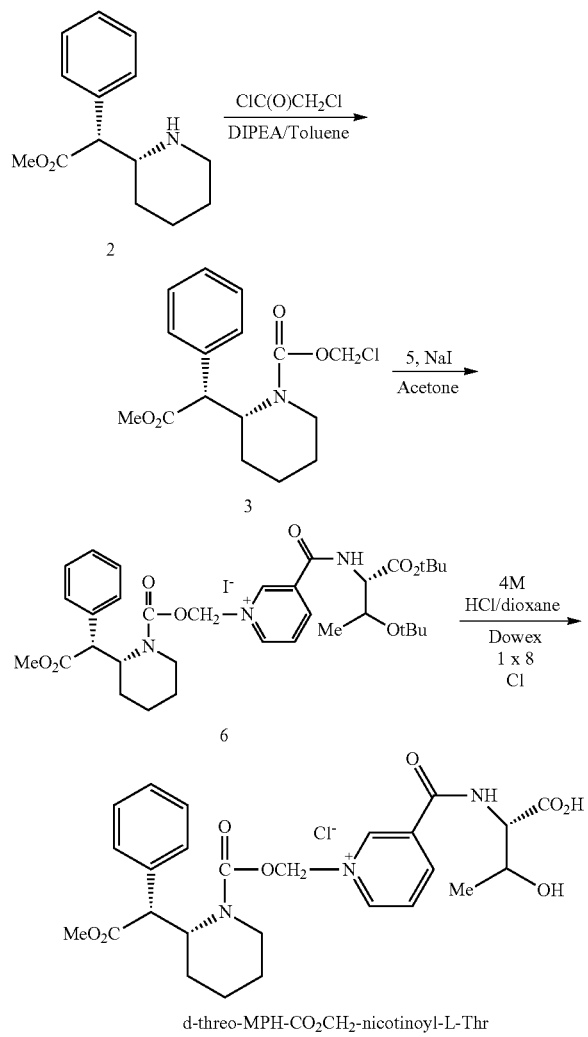

Nicotinoyl-Thr(tBu)OtBu 5:

Nicotinoyl-Thr(tBu)OtBu was prepared with the same procedure as nicotinoyl-Ser(tBu)OtBu. The yield was 90.4%.

3-(((1S,2R)-1-carboxy-2-hydroxypropyl)carbamoyl)-1-(((R)-2-(2-(R)-methoxy-2-oxo-1-phenylethyl)piperidine-1-carbonyloxy)methyl)pyridium chloride:

Nicotinoyl-Thr(tBu)OtBu 5 (0.336 g, 1 mmol) and carbamate 3 (0.355 g, 1.09 mmol, 1.09 eq.) were dissolved in acetone (8 mL). Then NaI (0.161 g, 1.08 mmol, 1.08 eq.) was added. The reaction was refluxed for 1.5 hr. Upon cooling to room temperature, the reaction mixture was kept at room temperature for 1 hr. The solid (NaCl) was filtered off. The filtrate was concentrated and dried over vacuum for 1 hr to give amorphous solid 0.796 g. The solid in 4 M HCl/dioxane (5 mL) was stirred at room temperature for 2 hr.

Solvent was evaporated and the remaining was coevaporated with DCM (two times 6 mL), and then dried over vacuum for 1 hr. to give amorphous solid 0.70 g. It was dissolved 10 ml of ethanol and treated with resin twice (two times 1 g, Dowex 1×8, 200-400, Cl form, prewashed with water and ethanol, wet). The filtrate after resin treatment was concentrated and dried over vacuum to give amorphous solid 0.638 g. The solid was dissolved in 4 ml of EtOH and then 6 mL of TBME was added. Crystal formed slowly. After 2 days, solid was collected and washed with EtOH/TBME (1:1, three times 2 mL), dried over vacuum. 390 mg of white solid (d-MPH-CO₂CH₂-nicotinoyl-L-Thr chloride) was obtained. The yield was 70.9% and the purity was 99%.

When conjugating d-methylphenidate via carbamate bond to a methylene oxide linker which in turn is connected to the nitrogen of the pyridine ring of a nicotinoyl-amino acid moiety unexpected differences in solubility and pharmacokinetics were observed between conjugates of racemic threo-methylphenidate (i.e., d and l isomers in a 1:1 ratio) and conjugates of isomerically pure d-threo-methylphenidate and l-threo-methylphenidate. Moreover, these differences were not limited to varying the chirality of methylphenidate with the same terminal amino acid. Differences were also observed when the conjugate comprised the same form of d-methylphenidate but different amino acids. The conjugates d-MPH-CO₂CH₂-nicotinoyl-L-Ser, l-MPH-CO₂CH₂-nicotinoyl-L-Ser, and d-MPH-CO₂CH₂-nicotinoyl-L-Thr each have three chiral centers.

In one embodiment, the conjugate d/l-MPH-CO₂CH₂-nicotinoyl-L-Ser was recrystallized from a mixture (1:1) of isopropylalcohol (IPA) and isopropylacetate (IPAc) yielding approximately 45.2% of product (purity of about 98% by HPLC). A similar amount of d-MPH-CO₂CH₂-nicotinoyl-L-Ser recrystallized from IPA and IPAc (2:1) yielded approximately 81.5% of product (purity of about 97.6% by HPLC). This result is nonobvious since the yield of the isomerically pure conjugate was significantly higher even though more IPA was used which would be expected to improve the solubility of the conjugate. The results indicated that l-MPH-CO₂CH₂-nicotinoyl-L-Ser has significantly higher solubility in IPA/IPAc when compared to d-MPH-CO₂CH₂-nicotinoyl-L-Ser (Formula I).

In another embodiment, the following compounds were dosed orally in rats at equimolar doses: d-MPH.HCl, l-MPH.HCl, d-MPH-CO₂CH₂-nicotinoyl-L-Ser, l-MPH-CO₂CH₂-nicotinoyl-L-Ser, d-MPH-CO₂CH₂-nicotinoyl-L-Thr, and l-MPH-CO₂CH₂-nicotinoyl-L-Thr. As shown in FIG. 1 and Table 3, when comparing d-MPH.HCl and l-MPH.HCl, the bioavailability of the d-isomer was significantly higher vs the l-isomer. The d:l-isomer ratios of mean $C_{max}$ and AUC were about 192% and 124%, respectively, as shown in Table 3). In addition, the $T_{max}$ of l-MPH was longer (0.7 hours) compared to d-MPH (0.4 hours)(Table2).

TABLE 2

PK parameters for d-methylphenidate and l-methylphenidate after oral administration of d-MPH•HCl and l-MPH•HCl in rats.

| | d-MPH•HCl | l-MPH•HCl |
|---|---|---|
| Analyte | d-MPH | l-MPH |
| $C_{max}$ (ng/mL) | 98.9 | 51.5 |
| AUC (hours*ng/mL) | 119.2 | 96.4 |
| $T_{max}$ (hours) | 0.4 | 0.7 |

TABLE 3 d:l-isomer ratios for unconjugated d-methylphenidate after oral administration in rats.

| d:l Ratio | unconjugated MPH |
|---|---|
| $C_{max}$ | 192% |
| AUC | 124% |
| $T_{max}$ | 62% |

Figure 2:
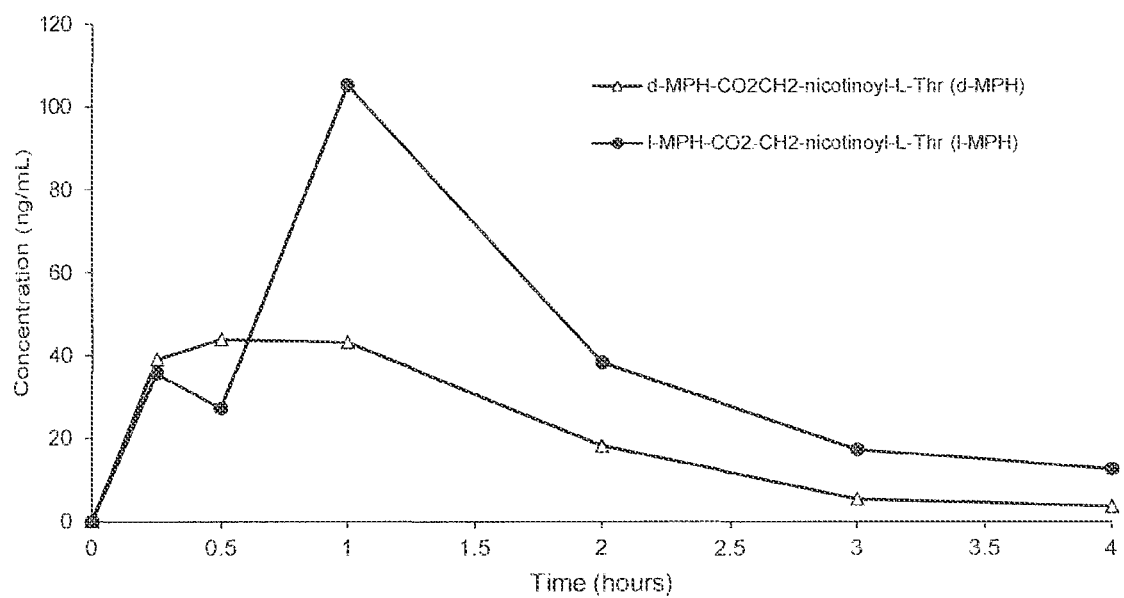
FIG. 2. Oral PK curves comparing the d-MPH-$CO_2CH_2$-nicotinoyl-L-Thr conjugate with l-MPH-$CO_2CH_2$-nicotinoyl-L-Thr in rats.

As shown in FIG. 2, relative exposure to d-MPH and l-MPH released from d-MPH-CO$_2$CH$_2$-nicotinoyl-L-Thr and l-MPH-CO$_2$CH$_2$-nicotinoyl-L-Thr, respectively, were reversed (d:l conjugate ratios of mean $C_{max}$ and AUC were about 58% and 53%, respectively as shown in Table 4) when compared to unconjugated d-MPH and l-MPH. The relationship between $T_{max}$ for d-MPH-CO$_2$CH$_2$-nicotinoyl-L-Thr and l-MPH-CO$_2$CH$_2$-nicotinoyl-L-Thr (0.6 hours vs 1.1 hours, respectively as shown in Table 4) was similar compared to unconjugated d-MPH and l-MPH.

TABLE 4

PK parameters for d-methylphenidate and l-methylphenidate after oral administration of d-MPH-CO$_2$CH$_2$-nicotinoyl-L-Thr and l-MPH-CO$_2$CH$_2$-nicotinoyl-L-Thr in rats.

| | d-MPH-CO$_2$CH$_2$-nicotinoyl-L-Thr | l-MPH-CO$_2$CH$_2$-nicotinoyl-L-Thr |
|---|---|---|
| Analyte | d-MPH | l-MPH |
| $C_{max}$ (ng/mL) | 62.5 | 107.6 |
| AUC (hours*ng/mL) | 84.2 | 160.0 |
| $T_{max}$ (hours) | 0.6 | 1.1 |

TABLE 5 d:l-isomer ratios for MPH-CO$_2$CH$_2$-nicotinoyl-L-Thr after oral administration in rats.

| d:l Ratio | MPH-CO$_2$CH$_2$-nicotinoyl-L-Thr |
|---|---|
| $C_{max}$ | 58% |
| AUC | 53% |
| $T_{max}$ | 57% |

Figure 3:
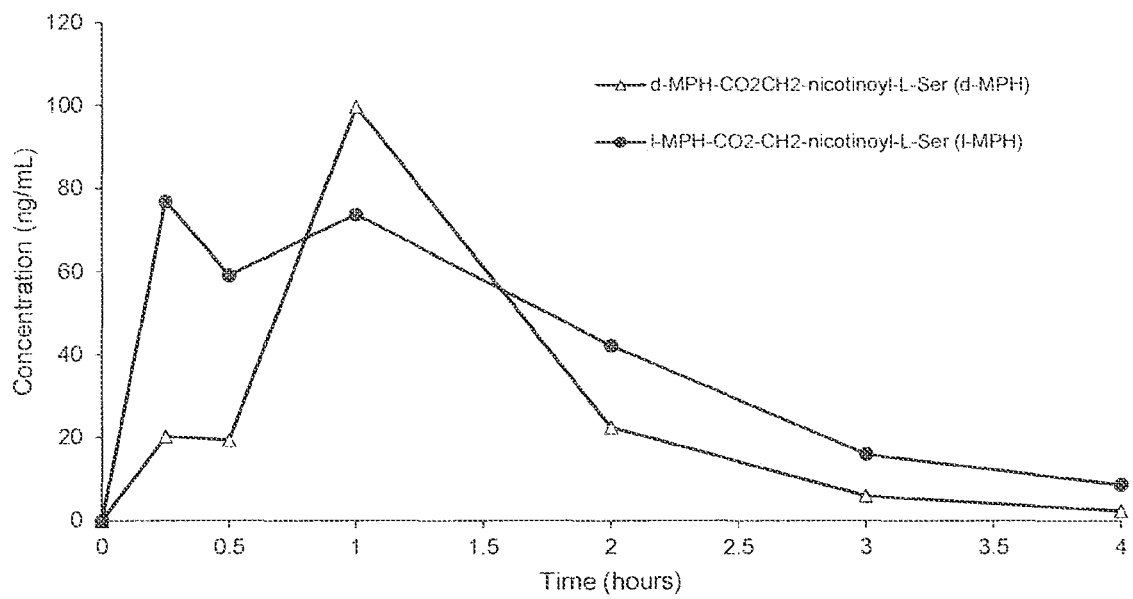
FIG. 3. Oral PK curves comparing the d-MPH-$CO_2CH_2$-nicotinoyl-L-Ser conjugate with l-MPH-$CO_2CH_2$-nicotinoyl-L-Ser in rats.

As shown in FIG. 3, the conjugates comprising L-serine produced were again different from the L-threonine conjugates and from unconjugated methylphenidate. While peak exposure ($C_{max}$) to d-MPH and l-MPH released from d-MPH-CO$_2$CH$_2$-nicotinoyl-L-Ser and l-MPH-CO$_2$CH$_2$-nicotinoyl-L-Ser, respectively, were similar, overall exposure (AUC) was lower and $T_{max}$ significantly shorter for l-MPH-CO$_2$CH$_2$-nicotinoyl-L-Ser (d:l conjugate ratios of mean $C_{max}$ and AUC were about 94% and 73%, respectively as shown Table 7; $T_{max}$ was 1.0 and 0.6 hours for d-MPH-CO$_2$CH$_2$-nicotinoyl-L-Ser and l-MPH-CO$_2$CH$_2$-nicotinoyl-L-Ser, respectively, as shown in Table 6).

TABLE 6

PK parameters for d-methylphenidate and l-methylphenidate after oral administration of d-MPH-CO$_2$CH$_2$-nicotinoyl-L-Ser and l-MPH-CO$_2$CH$_2$-nicotinoyl-L-Ser in rats.

| | d-MPH-CO$_2$CH$_2$-nicotinoyl-L-Ser | l-MPH-CO$_2$CH$_2$-nicotinoyl-L-Ser |
|---|---|---|
| Analyte | | |
| $C_{max}$ (ng/mL) | 99.7 | 106.4 |
| AUC (hours*ng/mL) | 116.9 | 159.5 |
| $T_{max}$ (hours) | 1.0 | 0.6 |

TABLE 7 d:l-isomer ratios for MPH-CO$_2$CH$_2$-nicotinoyl-L-Ser after oral administration in rats.

| d:l Ratio | MPH-CO$_2$CH$_2$-nicotinoyl-L-Ser |
|---|---|
| $C_{max}$ | 94% |
| AUC | 73% |
| $T_{max}$ | 182% |

In summary, the serine conjugates produced extended release of d-MPH and the threonine conjugates produced a more effective and extended release of l-MPH. Thus, by changing the stereochemistry of methylphenidate, the respective prodrugs exhibited selective absorption and/or clearance of d-MPH vs l-MPH. Results of the human PK study confirmed that at least for d-MPH-CO$_2$CH$_2$-nicotinoyl-L-Ser, d-MPH was effectively released in an extended-release fashion and absorbed into the systemic circulation following oral administration.

Treatment of Sleep Disorders

In some embodiments, the present technology provides methods of the treatment of sleep disorders. Exemplary, non-limiting sleep disorders include excessive daytime sleepiness associated with central hypersomnolence disorders, obstructive sleep apnea, or shift work disorder, Central hypersomnolence disorders such as narcolepsy type 1 (with cataplexy), narcolepsy type 2, idiopathic hypersomnia, Kleine-Levin syndrome, hypersomnia due to a medical condition, hypersomnia due to a medication or substance, hypersomnia associated with a psychiatric condition, and insufficient sleep syndrome.

Definitions

The primary forms of central hypersomnolence disorders are narcolepsy type 1, narcolepsy type 2, idiopathic hypersomnia, and Kleine-Levin syndrome causing excessive daytime sleepiness (EDS) during the day even after a normal night of sleep or a prolonged night of sleep. These four disorders have overlapping symptoms. Patients with narcolepsy type 1 and type 2 may additionally experience sleep paralysis and hypnogogic hallucinations. Narcolepsy type 1 patients also suffer from cataplexy whereas patients with narcolepsy type 2, idiopathic hypersomnia, and Kleine-Levin syndrome do not. Cataplexy is a sudden episode of weakness triggered by a strong emotion such as humor or anger.

Some patients with idiopathic hypersomnia are classic "long-sleepers" who have a stable sleep state and sleep extremely long hours, but are still excessively tired during the day. Other patients with idiopathic hypersomnia have an unstable sleep state and do not sleep for very long periods.

Symptoms of narcolepsy type 2 are similar to idiopathic hypersomnia but individuals with narcolepsy type 2 typically experience more REM sleep compared to individuals with idiopathic hypersomnia.

In contrast to the other three types of central hypersomnolence disorders that are characterized by chronic excessive daytime sleepiness, individuals with Kleine-Levin syndrome experience episodic sleepiness that may last for days to weeks. These episodes can be separated by months without excessive sleepiness. Patients typically sleep very long durations during symptomatic periods and may experience changes in thinking, behaviors, and/or personality.

Treatment

The goal for the treatment of these sleep disorders is to reduce daytime sleepiness. There is evidence that CNS stimulants like methylphenidate can reduce excessive daytime sleepiness. Stimulants improve alertness and drowsiness during the day, and may thereby help with nocturnal sleep as well. Some desirable attributes of a stimulant for the treatment of sleep disorders such as central hypersomnolence disorders may include long duration of action, slow elimination of drug plasma concentrations to avoid "crashing" at the end of the day and other potential drug offset related side effects, and low abuse potential.

There may be additional benefits to combine CNS stimulants with other therapies including, for example, antidepressants. These combinations may not only alleviate sleepiness but also REM-related symptoms such as cataplexy.

Pharmaceutical Kits

In some embodiments, the present technology provides pharmaceutical kits comprising a composition of the present technology that has increased water solubility than compared to the unconjugated d-methylphenidate. In some embodiments, the pharmaceutical kit comprises a specific amount of individual doses in a package, each dose comprising a pharmaceutically and/or therapeutically effective amount of the composition comprising the prodrug or conjugate of the present technology and unconjugated methylphenidate. The pharmaceutical kit may further include instructions for use. In some other embodiments, the kit comprises oral thin films or strips comprising the composition comprising the prodrugs or conjugates of the present technology and unconjugated methylphenidate. In some other embodiments, the kit comprises one or more blister packs containing the composition comprising the prodrug or conjugate of the present technology and unconjugated methylphenidate. It will be appreciated by one skilled in the art that, in some embodiments, the kit may include individual doses that have different dosage amounts.

The present technology provides pharmaceutical kits for the treatment or prevention of any of the indications mentioned above, including ADHD, eating disorder, binge eating disorder, obesity, central hypersomnolence disorders, narcolepsy, chronic fatigue, sleep disorder, EDS, cocaine addiction, or drug withdrawal symptoms in a subject. The subject may be a human or animal subject. As used herein the term animal is used in the veterinary sense and does not include humans. Suitable human subjects include neonatal subjects, pediatric subjects, adolescent subjects, adult subjects, geriatric subjects, elderly subjects and normative subjects. The kit comprises a specific amount of the individual doses in a package, each dose containing a pharmaceutically and/or therapeutically effective amount of at least one conjugate of d-methylphenidate of the present technology and unconjugated methylphenidate. The kit can further include instructions for use of the kit, wherein the instructions for use of the kit may further comprise methods for treating or preventing any of the indications selected from the group consisting of ADHD, eating disorder, binge eating disorder, obesity, central hypersomnolence disorders, narcolepsy, chronic fatigue, sleep disorder, EDS, cocaine addiction, or drug withdrawal symptoms in a subject. The specified amount of individual doses may be from about 1 to about 100 individual dosages, alternatively from about 1 to about 60 individual dosages, alternatively from about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, about 1, about 2, about 5, about 10 and multiplied factors thereof, (e.g., about ×1, about ×2, about ×2.5, about ×5, about ×10, about ×100, etc). One of skill in the art will appreciate that some embodiments of the kit of the present technology may include graduated individual doses (i.e. dose amounts that increase or decrease over a period of time), and/or a graduated dosing regimen, and instructions for use.

In certain embodiments, compositions of the present technology comprising unconjugated methylphenidate and at least one conjugate of d-methylphenidate can be used in neonatal, pediatric, adolescent, adult and/or geriatric subjects with sleep disorders. For example, in some embodiments, the present compositions can be used for a once-daily dosing with a potentially improved onset and a long duration of action attributes that may benefit neonatal, pediatric and/or adolescent subjects with sleep disorders.

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1: d-threo-MPH-CO$_2$CH$_2$-nicotinoyl-L-Ser and Unconjugated Methylphenidate The plasma concentrations of d-methylphenidate were measured by LC-MS/MS over time. The oral plasma concentrations of d-methylphenidate released from d-threo-MPH-CO$_2$CH$_2$-nicotinoyl-L-Ser were compared with unconjugated d-methylphenidate after oral administration in rats.

Figure 4:
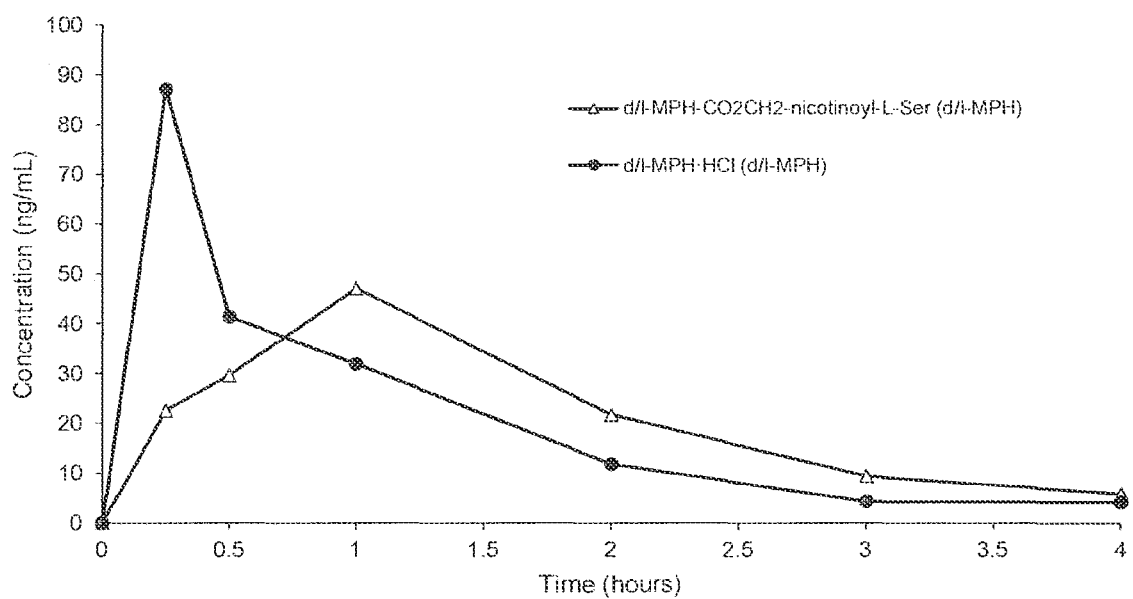
FIG. 4. Oral PK curves comparing the d-MPH-$CO_2CH_2$-nicotinoyl-L-Ser with unconjugated d-methylphenidate in rats.

FIG. 4 demonstrates the PK curve achieved by the d-threo-MPH-CO$_2$CH$_2$-nicotinoyl-L-Ser as compared with unconjugated forms and all of the specific pharmacokinetic parameter data is presented in Tables 8-9. As shown in Table 8, 4.75 mg of conjugate (d-threo-MPH-CO$_2$CH$_2$-nicotinoyl-L-Ser) was used as compared to 2.39 mg unconjugated d-methylphenidate hydrochloride used, however, both had the same amount of the d-MPH (mg/kg), which was 2.06 mg/kg. The human equivalent dose for the conjugate was 0.8 mg/kg as compared to 0.4 mg/kg for unconjugated d-methylphenidate.

TABLE 8

Comparison of prodrugs of d-methylphenidate with unconjugated methylphenidate dosed orally in rats.

| Dose References | Dose | |
|---|---|---|
| | d-MPH-CO$_2$CH$_2$-nicotinoyl-L-Ser | d-MPH•HCl |
| Test Article (mg/kg) | 4.75 | 2.39 |
| d-MPH Content (mg/kg) | 2.06 | 2.06 |
| Human Equivalent Dose (HED) | 0.8 | 0.4 |

As shown in Table 9, the conjugate of d-threo-MPH-CO$_2$CH$_2$-nicotinoyl-L-Ser has a mean AUC$_{0-4h}$ of d-methylphenidate of about 86.1 h×ng/mL±10.0 h×ng/mL when administered orally to a rat when compared to unconjugated d-methylphenidate of about 79.5 h×ng/mL±10.0 h×ng/mL. The conjugate has a mean C$_{max}$ of d-methylphenidate of about 51.3 ng/mL±10 ng/mL when administered orally to a rat compared to unconjugated d-methylphenidate of about 96.6 ng/mL±10 ng/mL. The conjugate has a T$_{max}$ of d-methylphenidate of about 1.2 hours±10 hours when compared to unconjugated d-methylphenidate of about 0.4 hours±10 hours when administered orally to a rat.

TABLE 9

PK comparison of prodrugs of d-methylphenidate with unconjugated d-methylphenidate dosed orally in rats.

| PK Parameter | d-MPH-CO$_2$CH$_2$-nicotinoyl-L-Ser (N) | d-MPH•HCl (N) |
|---|---|---|
| AUC$_{0-4\,h}$ (h × ng/mL) | 86.1 (10) | 79.5 (10) |
| C$_{max}$ (ng/mL) | 51.3 (10) | 96.6 (10) |
| T$_{max}$ (h) | 1.2 (10) | 0.4 (10) |

As shown in FIG. 4, after 4.75 mg conjugate was fed orally to rats, plasma concentrations of d-methylphenidate released from the conjugate are increased from 0 to about 1.2 hours following oral administration in a rat when compared to unconjugated d-methylphenidate (2.39 mg) of about 0.4 hour. Plasma concentrations of d-methylphenidate released from the conjugate are slowly increased from about 1.2 to about 4 hour following oral administration in a rat.

Figure 5:
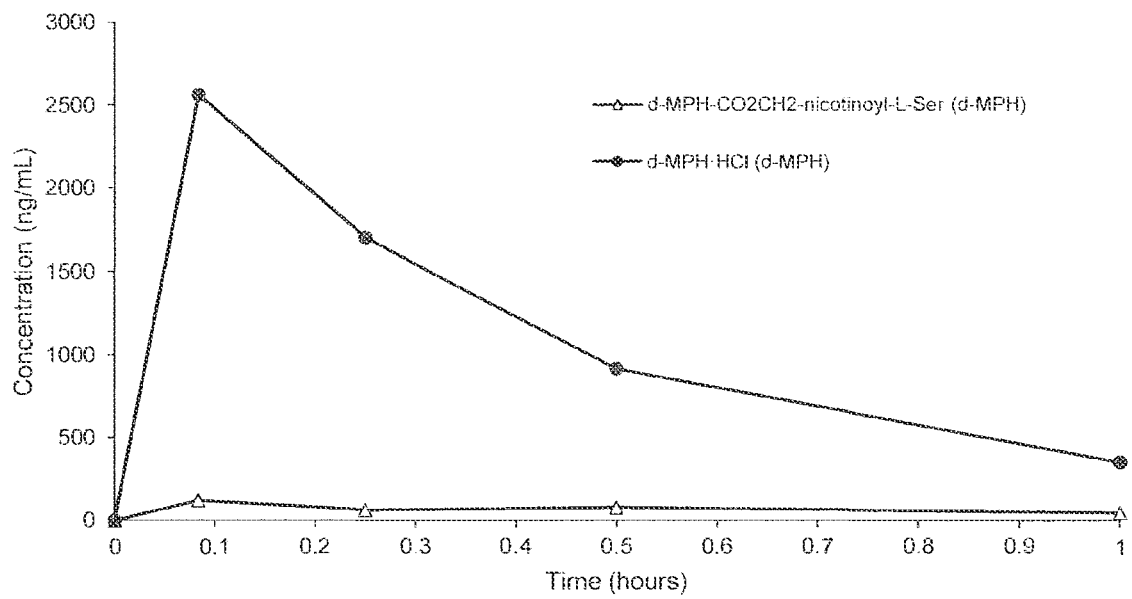
FIG. 5. Intranasal PK curves comparing the d-MPH-$CO_2CH_2$-nicotinoyl-L-Ser with unconjugated d-methylphenidate in rats.

As shown in FIG. 5 and Table 10, after 4.75 mg conjugate was intranasally administered to rats, plasma concentrations of d-methylphenidate released from the conjugate are substantially flat from about 0 to about 1 hour following intranasal administration in a rat. However, after 2.39 mg unconjugated d-methylphenidate was intranasally administered to rats, plasma concentrations of d-methylphenidate released from the conjugate are dramatically increased from about 0 to about 0.1 hour following intranasal administration in a rat. Conjugated d-methylphenidate was about 6% AUC and 5% C$_{max}$ of unconjugated d-methylphenidate.

Figure 6:
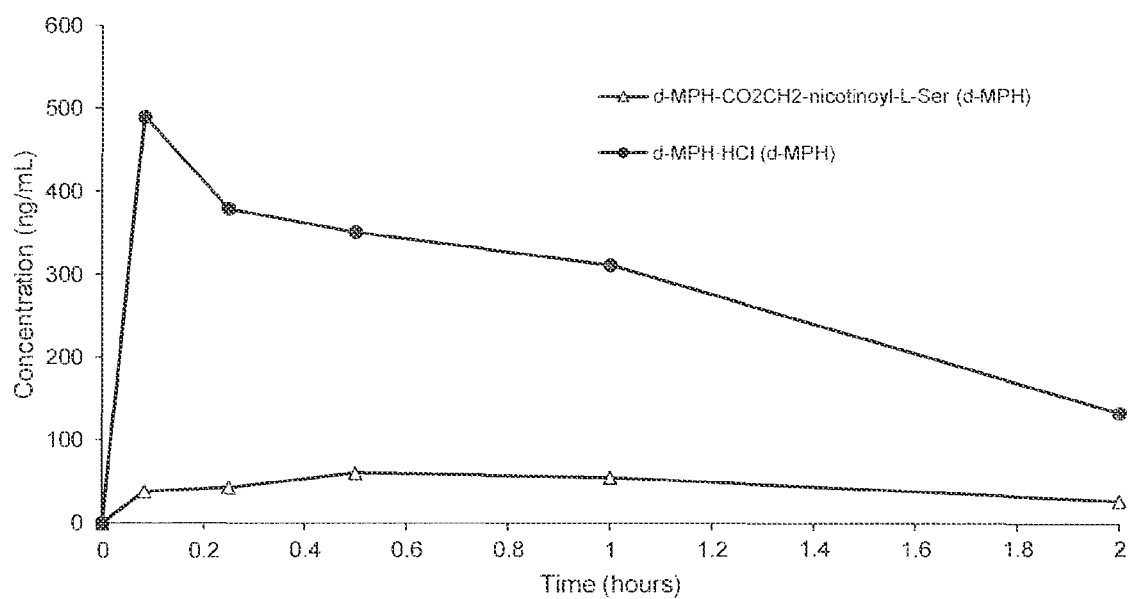
FIG. 6. Intravenous PK curves comparing the d-MPH-$CO_2CH_2$-nicotinoyl-L-Ser with unconjugated d-methylphenidate in rats.

Similar to FIG. 5, FIG. 6 and Table 10 show that after 4.75 mg conjugate was injected intravenously to rats, plasma concentrations of d-methylphenidate released from the conjugate are substantially flat from about 0 to about 2 hours following intravenous administration in a rat. However, after 2.39 mg unconjugated d-methylphenidate was injected intravenously to rats, plasma concentrations of d-methylphenidate released from the conjugate are dramatically increased from about 0 to about 0.1 hour following intravenous administration in a rat. Conjugated d-methylphenidate was about 17% AUC and 12% C$_{max}$ of unconjugated d-methylphenidate.

TABLE 10

PK comparison of prodrugs of d-methylphenidate with unconjugated d-methylphenidate dosed intranasally and intravenously in rats.

| | Intranasal (N) | | Intravenous (N) | |
|---|---|---|---|---|
| PK Parameter | d-MPH-CO$_2$CH$_2$-nicotinoyl-L-Ser | d-MPH | d-MPH-CO$_2$CH$_2$-nicotinoyl-L-Ser | d-MPH |
| AUC$_{0-1\,h}$ (h × ng/mL) | 67.4 (8) | 1110.8 (9) | 51.0 (8) | 312.6 (9) |
| AUC$_{0-2\,h}$ (h × ng/mL) | n/a | n/a | 93.5 (8) | 534.9 (9) |
| C$_{max}$ (ng/mL) | 118.9 (10) | 2561.6 (10) | 62.8 (10) | 541.8 (10) |
| T$_{max}$ (h) | 0.1 (10) | 0.1 (10) | 0.9 (10) | 0.4 (10) |

A study was conducted in humans to assess the pharmacokinetics (PK) of 32 mg of d-MPH-CO$_2$CH$_2$-nicotinoyl-L-Ser (liquid, dissolved in water) compared with 36 mg of Concerta® (tablet) after oral administration under fasted conditions (the dose of 32 mg of d-MPH-CO$_2$CH$_2$-nicotinoyl-L-Ser contains about 13.9 mg of d-methylphenidate, which was about 10.9% lower compared to the about 15.6 mg of d-methylphenidate in 36 mg of Concerta®). Twenty-four (24) healthy volunteers were enrolled in this open-label, single-dose, two-treatment, two-period PK trial.

Figure 7:
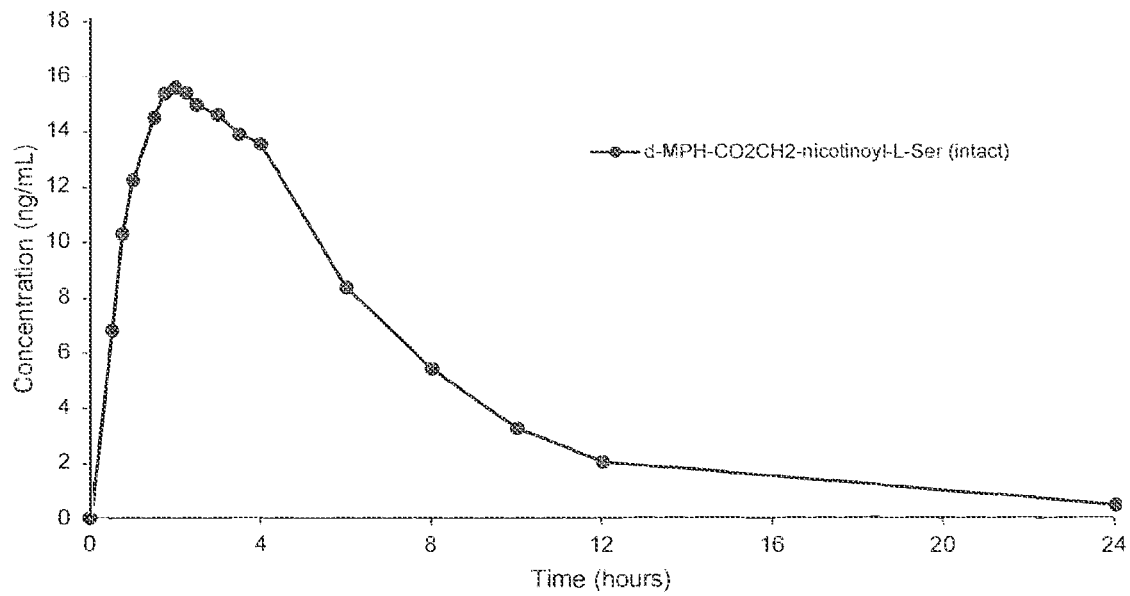
FIG. 7. Oral PK curve of the mean (N=24) plasma concentration-time profiles of intact d-threo-methylphenidate-$CO_2CH_2$-nicotinoyl-L-Ser after a single oral dose of 32 mg of the composition comprising d-threo-methylphenidate-$CO_2CH_2$-nicotinoyl-L-Ser.

FIG. 7 shows mean (N=24) plasma concentration-time profiles of intact d-MPH-CO$_2$CH$_2$-nicotinoyl-L-Ser after a single dose of 32 mg was administered as an oral liquid. Plasma concentrations of intact prodrug were increased from about 0 to about 2 hours following oral administration in a human subject and slowly decreased to about 0 at 24 hours post dose.

A study was conducted in humans to assess the pharmacokinetics (PK) of three different doses of d-methylphenidate HCl/d-MPH-CO$_2$CH$_2$-nicotinoyl-L-Ser Chloride (liquid, dissolved in water) at 8/64 mg, 12/56 mg, and 16/48 mg, as compared with 54 mg of Concerta® (tablet) after oral administration under fasted conditions. Forty-eight (48) healthy volunteers (12 per treatment arm) were enrolled in this open-label, single- and multiple-dose, four-treatment, one-period parallel PK trial. Table 11 provides a comparison of the four treatments used in this study.

TABLE 11

| Treatment | Dose of Unconjugated d-MPH HCl[1] (mg) | Dose of Formula II (d-MPH HCl)[2] (mg) | Total Dose of d-MPH HCl[3] (mg) | Ratio of Percent Doses[4] |
|---|---|---|---|---|
| A | 8 | 64 (32) | 40 | 20/80 |
| B | 12 | 56 (28) | 40 | 30/70 |
| C | 16 | 48 (24) | 40 | 40/60 |
| D[5] | 27 | — | 27 | — |

[1]d-MPH HCl = d-methylphenidate hydrochloride
[2]Formula II = d-MPH-CO$_2$CH$_2$-nicotinoyl-L-Ser-Cl; the amount in parentheses represents the molar equivalent dose of d-MPH HCl to the dose of Formula II.
[3]The Total Dose represents the combined dose of unconjugated and conjugated d-methylphenidate (Formula II) calculated by adding the dose in Col. 2 and the dose in Col. 3 (expressed in mg of d-MPH HCl).
[4]Percent Dose = ratio of API dose (Col. 2 or Col. 3) and Total Dose (Col. 4); the Ratio of Percent Doses is shown as Percent Dose of unconjugated d-methylphenidate (Col. 2)/Percent Dose of Formula II (Col. 3); all doses are expressed in molar equivalent doses of d-MPH HCl
[5]In addition to 27 mg of d-MPH HCl, a 54 mg Concerta ® tablet also includes 27 mg of l-MPH.

Eligible subjects included healthy male and female volunteers between the age of 18 and 55 years with a body mass index (BMI) between 18 and 32 kg/m$^2$ and a body weight between 60 and 100 kg at screening. The primary objective of the study was to assess the single and multiple dose pharmacokinetics of d-MPH-CO$_2$CH$_2$-nicotinoyl-L-Ser and d-methylphenidate following multiple doses of different combinations of d-methylphenidate HCl/d-MPH-CO$_2$CH$_2$-nicotinoyl-L-Ser Chloride administered orally once per day for 7 days in healthy volunteers under fasted conditions, compared to the same dosing regimen with a Concerta® tablet. After the 1st dose of study drug (Day 1), blood samples for PK were collected at pre-dose (0 hour; within 1 hour prior to dosing), and at 0.5, 1, 1.5, 2, 2.5, 3, 4.5, 6, 7, 7.5, 8, 8.5, 9, 10, 12, 13, and 24 hours±5 minutes post-dose. The 24-hr post-dose blood sample was taken before administration of the 2nd dose of study drug. After the 2nd, 3rd, 4th, 5th and 6th dose of study drug (Days 2-6), blood samples were collected at pre-dose (within 10 minutes prior to dosing), and at 1.5 and 8 hours±5 minutes post-dose. The pre-dose sample on Day 2 was the same as the 24-hour post-dose sample after the 1st dose. After the last dose (7th dose) of study drug (Day 7), blood samples for PK were collected at pre-dose (within 10 minutes prior to dosing), and at 0.5, 1, 1.5, 2, 2.5, 3, 4.5, 6, 7, 7.5, 8, 8.5, 9, 10, 12, 13, 24, 36, 48, 60 and 72 hours±5 minutes post-dose.

FIGS. 8-13 provide d-methylphenidate plasma concentration-time profiles for the three dose mixtures: 8/64 mg, 12/56 mg, and 16/48 mg of d-methylphenidate HCl/d-MPH-CO$_2$CH$_2$-nicotinoyl-L-Ser chloride, in adult human subjects. FIGS. 14-25 provide d-MPH-CO$_2$CH$_2$-nicotinoyl-L-Ser chloride plasma concentration time profiles for the three dose mixtures. FIGS. 26-35 provide d-methylphenidate plasma concentration-time profiles for each of the three dose mixtures: 8/64 mg, 12/56 mg, and 16/48 mg of d-methylphenidate HCl/d-MPH-CO$_2$CH$_2$-nicotinoyl-L-Ser chloride compared with Concerta® 54 mg. PK data are provided for each of the dose mixtures and Concerta® in Tables 12-15, respectively.

Figure 8:
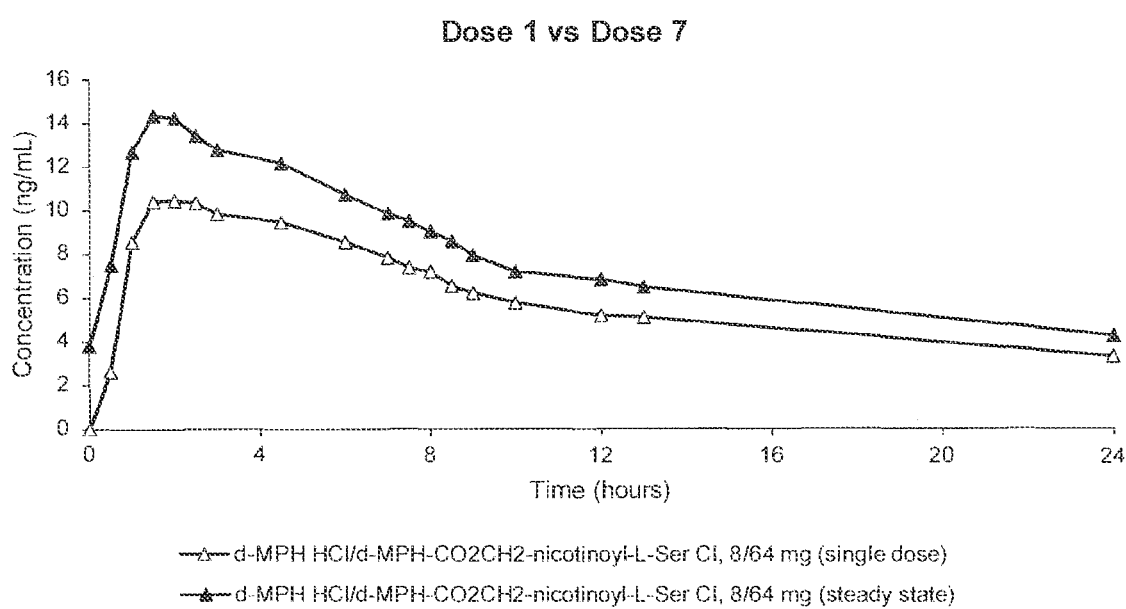
FIG. 8. Oral PK curves of the mean (N=12) d-methylphenidate plasma concentration-time profile following a single oral dose of d-methylphenidate HCl/d-MPH-$CO_2CH_2$-nicotinoyl-L-Ser chloride, 8/64 mg, and following the $7^{th}$ dose after multiple oral doses of d-methylphenidate HCl/d-MPH-$CO_2CH_2$-nicotinoyl-L-Ser chloride, 8/64 mg (steady state) administered in adult human subjects once every 24 hours.

FIG. 8 shows the mean (N=12) d-methylphenidate plasma concentration-time profiles following a single oral dose of d-methylphenidate HCl/d-MPH-CO$_2$CH$_2$-nicotinoyl-L-Ser chloride, 8/64 mg, and following the 7$^{th}$ oral dose after multiple oral doses of d-methylphenidate HCl/d-MPH-CO$_2$CH$_2$-nicotinoyl-L-Ser chloride administered to adult human subjects once every 24 hours (steady state).

Figure 9:
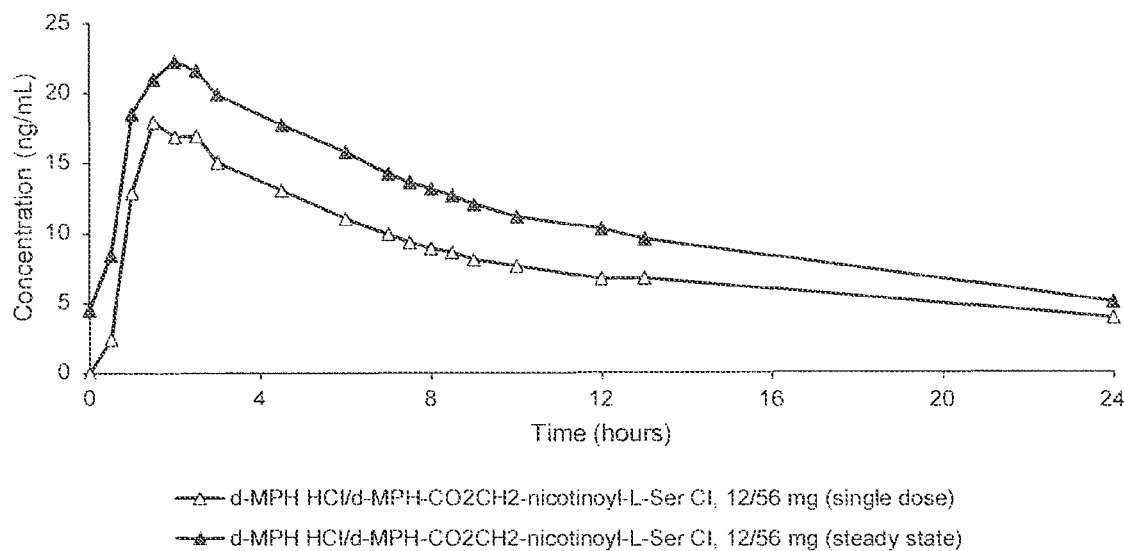
FIG. 9. Oral PK curves of the mean (N=12) d-methylphenidate plasma concentration-time profile following a single oral dose of d-methylphenidate HCl/d-MPH-$CO_2CH_2$-nicotinoyl-L-Ser chloride, 12/56 mg, and following the $7^{th}$ dose after multiple oral doses of d-methylphenidate HCl/d-MPH-$CO_2CH_2$-nicotinoyl-L-Ser chloride, 12/56 mg (steady state) administered in adult human subjects once every 24 hours.

FIG. 9 shows the mean (N=12) d-methylphenidate plasma concentration-time profiles following a single oral dose of d-methylphenidate HCl/d-MPH-CO$_2$CH$_2$-nicotinoyl-L-Ser chloride, 12/56 mg, and following the 7th oral dose after multiple oral doses of d-methylphenidate HCl/d-MPH-CO$_2$CH$_2$-nicotinoyl-L-Ser chloride administered to adult human subjects once every 24 hours (steady state). In this 12/56 mg treatment arm, two of the subjects had higher plasma concentrations of d-methylphenidate compared to the other 10 subjects. As a result, the mean (N=12) plasma concentration-time profiles shown in FIG. 9 are higher than the mean (N=10) d-methylphenidate plasma concentration-time profiles calculated without these two outlier subjects.

Figure 10:
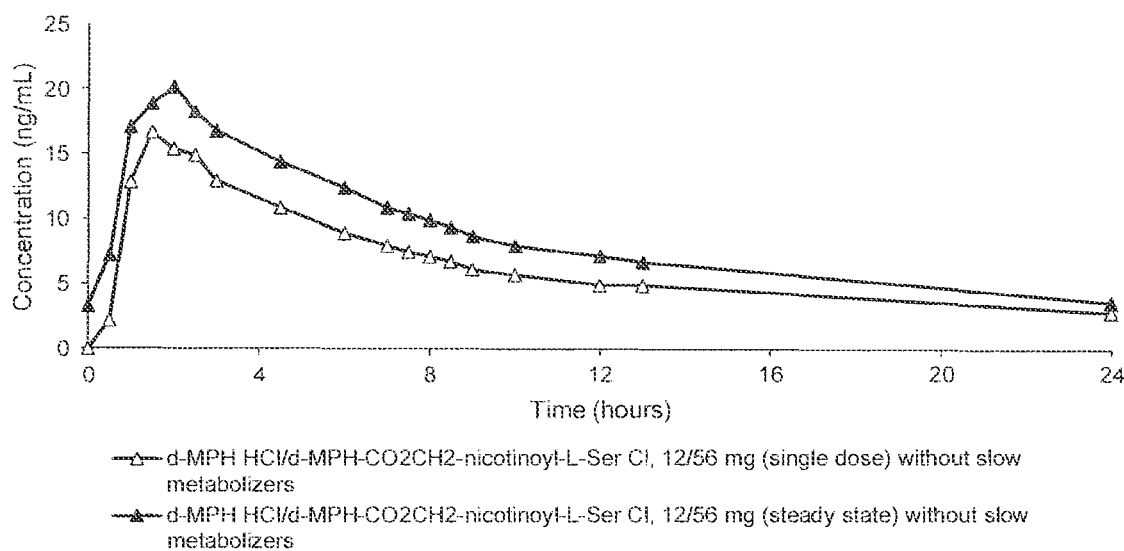
FIG. 10. Oral PK curves of the mean (N=10) d-methylphenidate plasma concentration-time profile following a single oral dose of d-methylphenidate HCl/d-MPH-$CO_2CH_2$-nicotinoyl-L-Ser chloride, 12/56 mg, and following the $7^{th}$ dose after multiple oral doses of d-methylphenidate HCl/d-MPH-$CO_2CH_2$-nicotinoyl-L-Ser chloride, 12/56 mg (steady state) administered in adult human subjects once every 24 hours, calculated without the outlier subjects (N=2).
Figure 11:
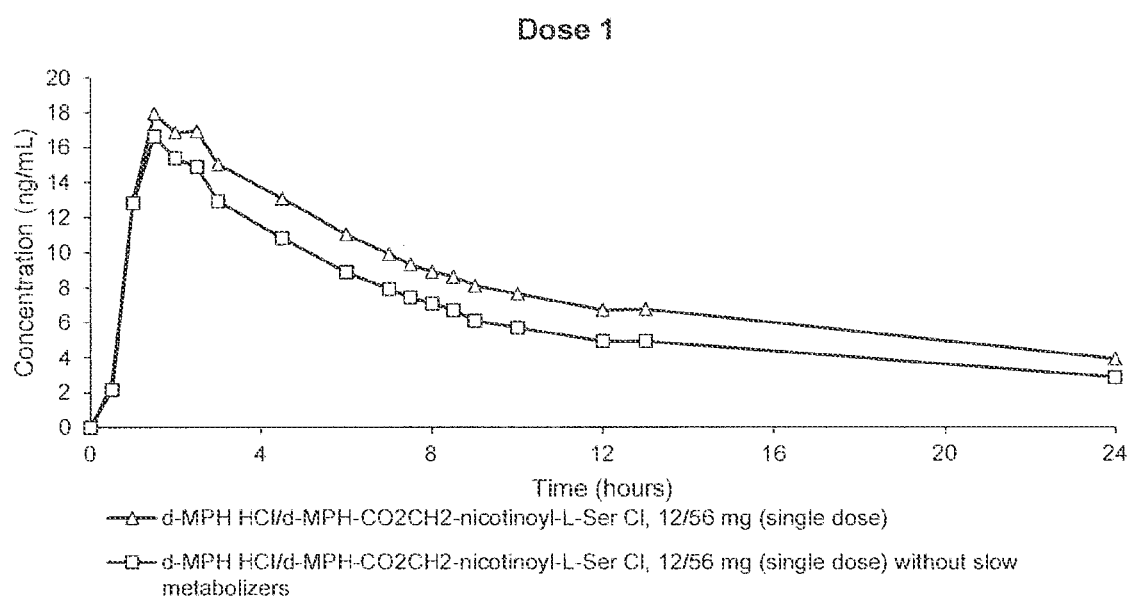
FIG. 11. Oral PK curves showing the mean d-methylphenidate plasma concentration-time profile following a single oral dose of d-methylphenidate HCl/d-MPH-CO$_2$CH$_2$-nicotinoyl-L-Ser chloride, 12/56 mg in adult human subjects, calculated with and without the outlier subjects.
Figure 12:
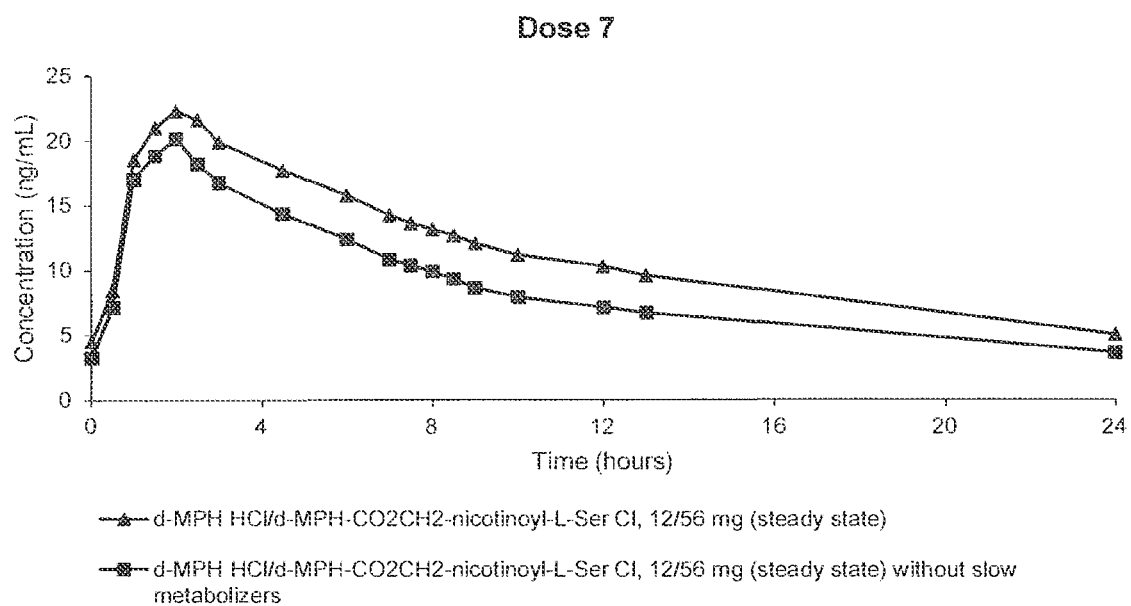
FIG. 12. Oral PK curves showing mean d-methylphenidate plasma concentration-time profile following the 7$^{th}$ dose after multiple oral doses of d-methylphenidate HCl/d-MPH-CO$_2$CH$_2$-nicotinoyl-L-Ser chloride, 12/56 mg administered in adult human subjects once every 24 hours, calculated with and without the outlier subjects.

The d-methylphenidate plasma concentration-time profiles calculated without the two outlier subjects are shown in FIG. 10. FIGS. 11 and 12, respectively, show the mean d-methylphenidate plasma concentration-time profiles with and without the outlier subjects following a single oral dose of d-methylphenidate HCl/d-MPH-CO$_2$CH$_2$-nicotinoyl-L-Ser chloride, and following the 7th dose after multiple oral doses of d-methylphenidate HCl/d-MPH-CO$_2$CH$_2$-nicotinoyl-L-Ser chloride. It is understood that depending on race, up to about 4-5% of the general population metabolizes or breaks down methylphenidate more slowly than the rest of the population ("slow metabolizers"). Due to their slower metabolism, the "slow metabolizers" take longer to break down methylphenidate and, as a result, have higher plasma concentrations of methylphenidate. Not wishing to be bound by any theory, it is suspected that the outlier subjects may have been "slow metabolizers."

Figure 13:
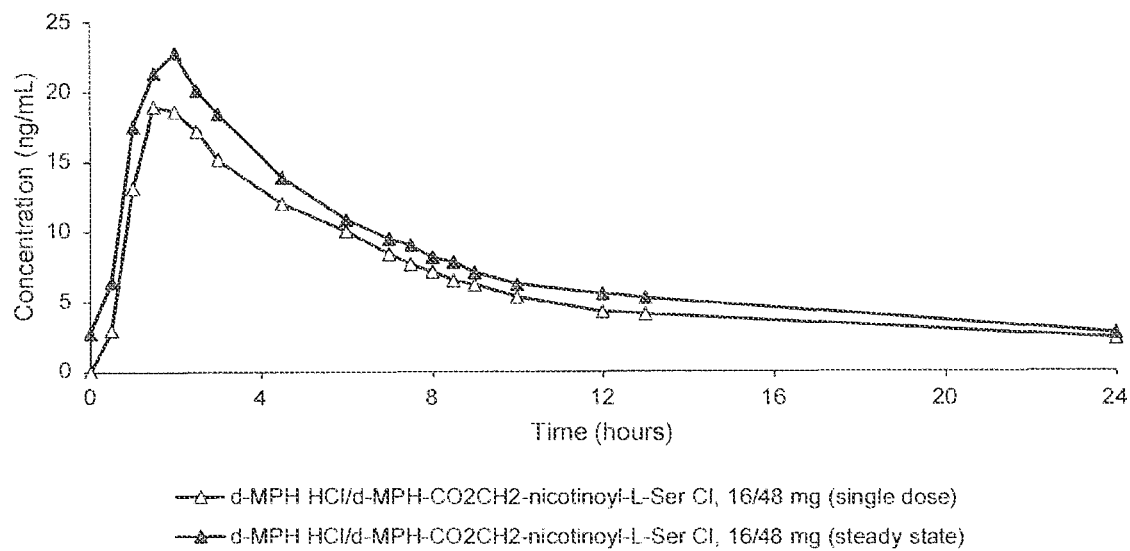
FIG. 13. Oral PK curves of the mean (N=12) d-methylphenidate plasma concentration-time profile following a single oral dose of d-methylphenidate HCl/d-MPH-CO$_2$CH$_2$-nicotinoyl-L-Ser chloride, 16/48 mg, and following the 7$^{th}$ dose after multiple oral doses of d-methylphenidate HCl/d-MPH-CO$_2$CH$_2$-nicotinoyl-L-Ser chloride, 16/48 mg (steady state) administered in adult human subjects once every 24 hours.

FIG. 13 shows the mean (N=12) d-methylphenidate plasma concentration-time profiles following a single oral dose of d-methylphenidate HCl/d-MPH-CO$_2$CH$_2$-nicotinoyl-L-Ser chloride, 16/48 mg, and following the 7th oral dose after multiple oral doses of d-methylphenidate HCl/d-MPH-CO$_2$CH$_2$-nicotinoyl-L-Ser chloride administered to adult human subjects once every 24 hours (steady state).

As shown in FIGS. 8-13, oral administration of each of the three treatment dose mixtures resulted in early absorption (immediate release) of d-methylphenidate followed by a slower extended release of d-methylphenidate. The figures also show that an appreciable concentration of d-methylphenidate remains in the bloodstream 24 hours after administration. Comparing dose 1 vs. dose 7 plasma concentrations at 24 hours, it can be seen that there is a modest accumulation of d-methylphenidate in the bloodstream after the 7$^{th}$ dose.

Figure 14:
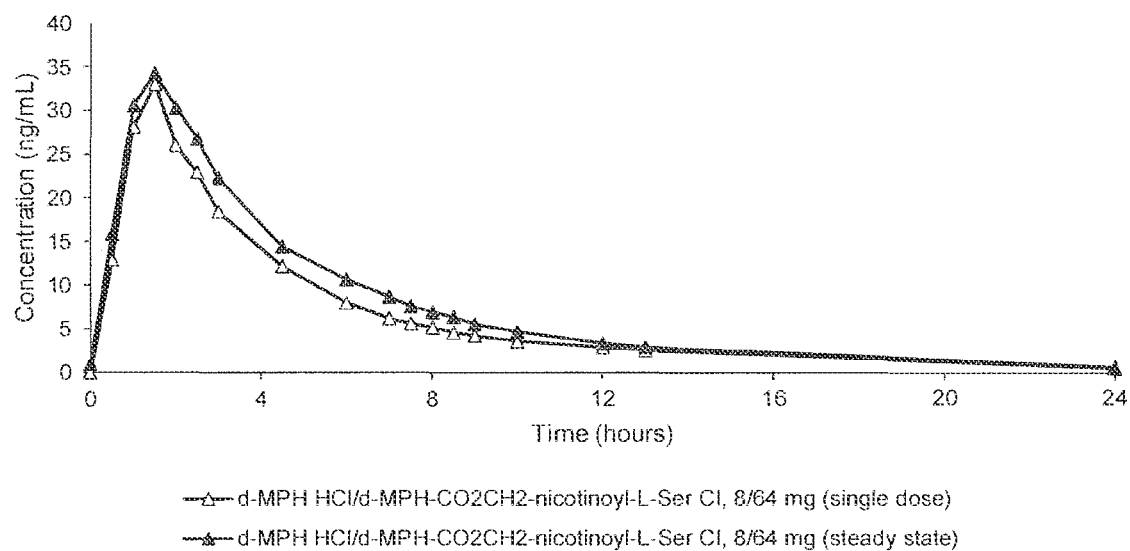
FIG. 14. Oral PK curves of the mean (N=12) d-MPH-CO$_2$CH$_2$-nicotinoyl-L-Ser plasma concentration-time profile following a single oral dose of d-methylphenidate HCl/d-MPH-CO$_2$CH$_2$-nicotinoyl-L-Ser chloride, 8/64 mg and following the 7$^{th}$ dose after multiple oral doses of d-methylphenidate HCl/d-MPH-CO$_2$CH$_2$-nicotinoyl-L-Ser chloride, 8/64 mg administered in adult human subjects once every 24 hours.
Figure 15:
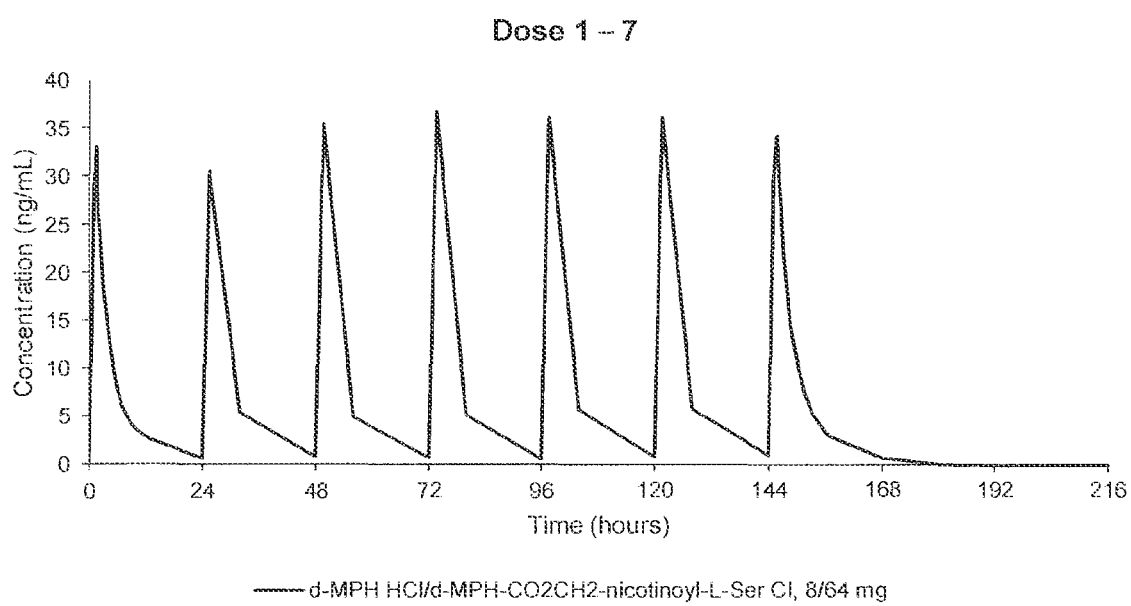
FIG. 15. Oral PK curves of the mean (N=12) d-MPH-CO$_2$CH$_2$-nicotinoyl-L-Ser plasma concentration-time profile following 7 oral doses of d-methylphenidate HCl/d-MPH-CO$_2$CH$_2$-nicotinoyl-L-Ser chloride, 8/64 mg administered in adult human subjects once every 24 hours.

FIG. 14 shows the mean (N=12) plasma concentration-time profile of intact d-MPH-CO$_2$CH$_2$-nicotinoyl-L-Ser chloride following a single oral dose of d-methylphenidate HCl/d-MPH-CO$_2$CH$_2$-nicotinoyl-L-Ser chloride 8/64 mg, and following the 7$^{th}$ dose after multiple doses of d-methylphenidate HCl/d-MPH-CO$_2$CH$_2$-nicotinoyl-L-Ser chloride administered to adult human subjects once every 24 hours. FIG. 15 shows the mean (N=12) plasma concentration-time profile of the intact d-MPH-CO$_2$CH$_2$-nicotinoyl-L-Ser chloride 8/64 mg following 7 oral doses of d-methylphenidate HCl/d-MPH-CO$_2$CH$_2$-nicotinoyl-L-Ser chloride administered to adult human subjects once every 24 hours.

Figure 16:
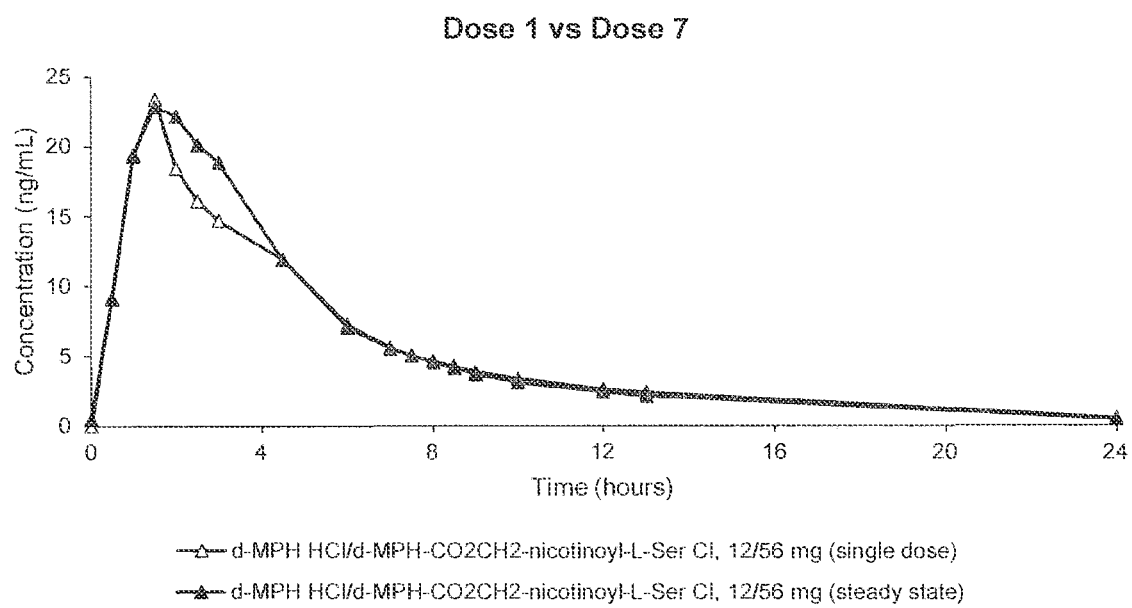
FIG. 16. Oral PK curves of the mean (N=12) d-MPH-CO$_2$CH$_2$-nicotinoyl-L-Ser plasma concentration-time profile following a single oral dose of d-methylphenidate HCl/d-MPH-CO$_2$CH$_2$-nicotinoyl-L-Ser chloride, 12/56 mg and following the 7$^{th}$ dose after multiple oral doses of d-methylphenidate HCl/d-MPH-CO$_2$CH$_2$-nicotinoyl-L-Ser chloride, 12/56 mg administered in adult human subjects once every 24 hours.
Figure 17:
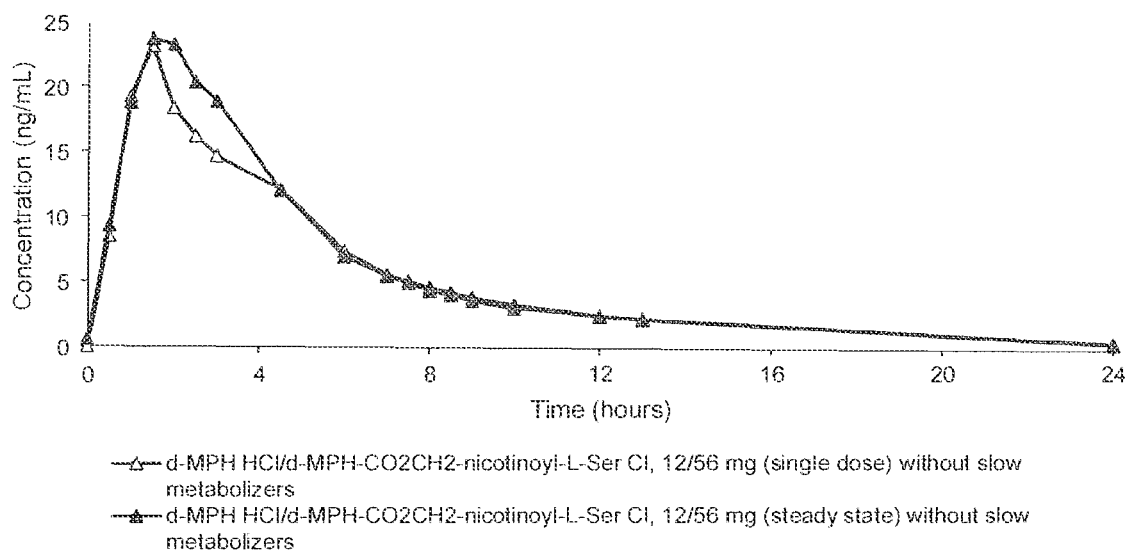
FIG. 17. Oral PK curves showing the mean d-MPH-CO$_2$CH$_2$-nicotinoyl-L-Ser plasma concentration-time profile following a single oral dose of d-methylphenidate HCl/d-MPH-CO$_2$CH$_2$-nicotinoyl-L-Ser chloride, 12/56 mg and following the 7$^{th}$ dose after multiple oral doses of d-methylphenidate HCl/d-MPH-CO$_2$CH$_2$-nicotinoyl-L-Ser chloride, 12/56 mg administered in adult human subjects once every 24 hours calculated without the outlier subjects.
Figure 18:
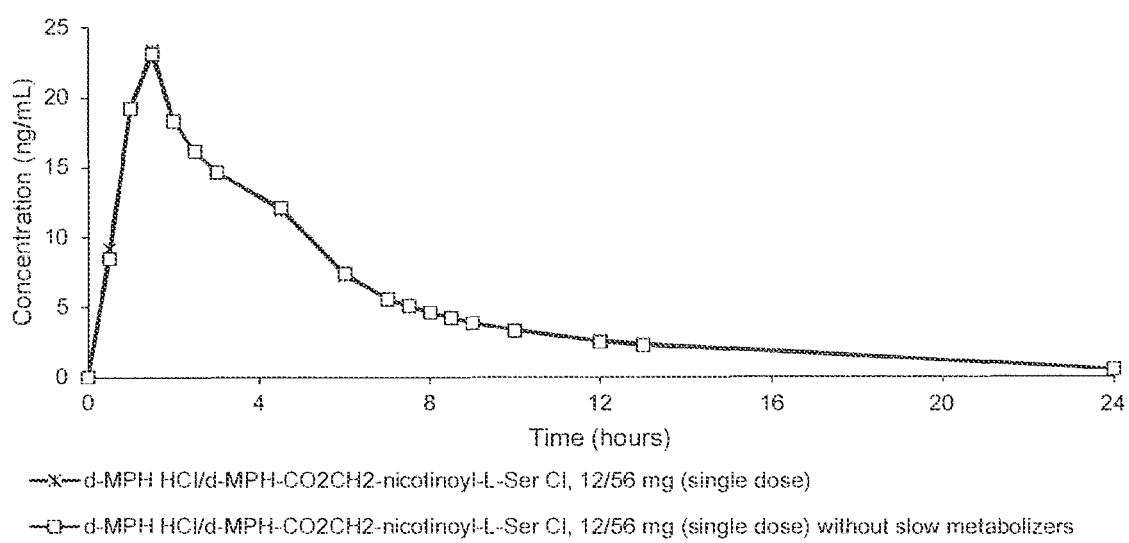
FIG. 18. Oral PK curves showing the mean d-MPH-CO$_2$CH$_2$-nicotinoyl-L-Ser plasma concentration-time profile following a single oral dose of d-methylphenidate HCl/d-MPH-CO$_2$CH$_2$-nicotinoyl-L-Ser chloride, 12/56 mg in adult human subjects calculated with and without the outlier subjects.
Figure 19:
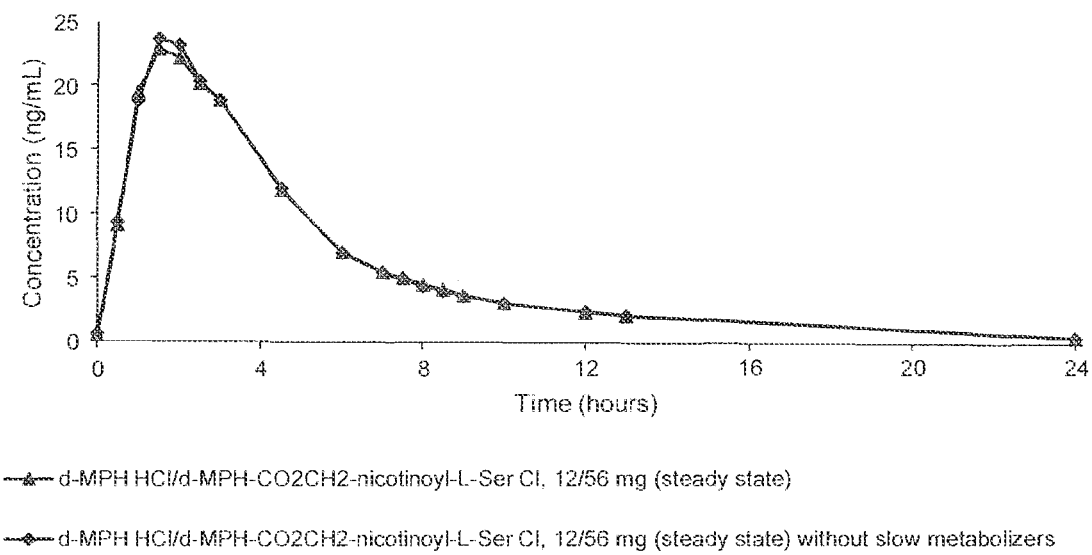
FIG. 19. Oral PK curves showing the mean d-MPH-CO$_2$CH$_2$-nicotinoyl-L-Ser plasma concentration-time profile following the 7$^{th}$ dose after multiple oral doses of d-methylphenidate HCl/d-MPH-CO$_2$CH$_2$-nicotinoyl-L-Ser chloride, 12/56 mg administered in adult human subjects once every 24 hours calculated with and without the outlier subjects.

FIG. 16 shows the mean (N=12) plasma concentration-time profile of intact d-MPH-CO$_2$CH$_2$-nicotinoyl-L-Ser chloride following a single oral dose of d-methylphenidate HCl/d-MPH-CO$_2$CH$_2$-nicotinoyl-L-Ser chloride 12/56 mg, and following the 7$^{th}$ dose after multiple doses of d-methylphenidate HCl/d-MPH-CO$_2$CH$_2$-nicotinoyl-L-Ser chloride 12/56 mg administered to adult human subjects once every 24 hours. FIG. 17 is similar to FIG. 16, but shows the mean (N=10) plasma concentration-time profiles calculated without the two outlier subjects. FIGS. 18 and 19, respectively, show the mean plasma concentration-time profiles of intact d-MPH-CO$_2$CH$_2$-nicotinoyl-L-Ser chloride with and without the two outlier subjects following a single oral dose of d-methylphenidate HCl/d-MPH-CO$_2$CH$_2$-nicotinoyl-L-Ser chloride 12/56 mg, and following the 7$^{th}$ dose after multiple doses of d-methylphenidate HCl/d-MPH-CO$_2$CH$_2$-nicotinoyl-L-Ser chloride 12/56 mg administered to adult human subjects once every 24 hours. As shown in FIGS. 18 and 19, the plasma concentration-time profiles for the intact d-MPH-CO$_2$CH$_2$-nicotinoyl-L-Ser chloride are substantially the same. This indicates that the two outlier subjects did not metabolize the intact d-MPH-CO$_2$CH$_2$-nicotinoyl-L-Ser chloride differently from the other subjects in this treatment arm, further supporting the belief that the two outlier subjects may have been "slow metabolizers" of d-methylphenidate.

Figure 20:
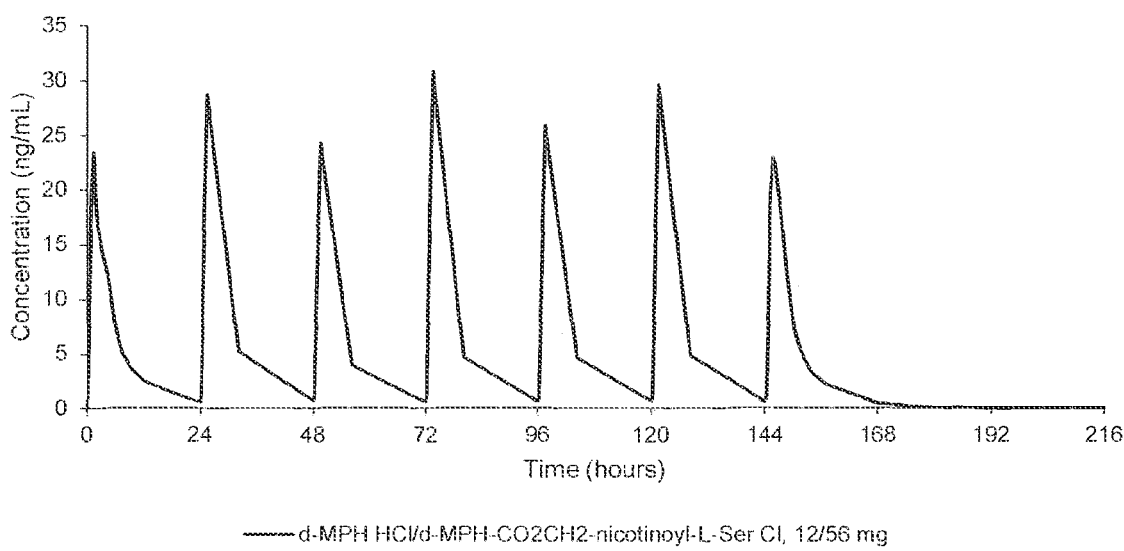
FIG. 20. Oral PK curves of the mean d-MPH-CO$_2$CH$_2$-nicotinoyl-L-Ser plasma concentration-time profile following 7 oral doses of d-methylphenidate HCl/d-MPH-CO$_2$CH$_2$-nicotinoyl-L-Ser chloride, 12/56 mg administered in adult human subjects once every 24 hours.
Figure 21:
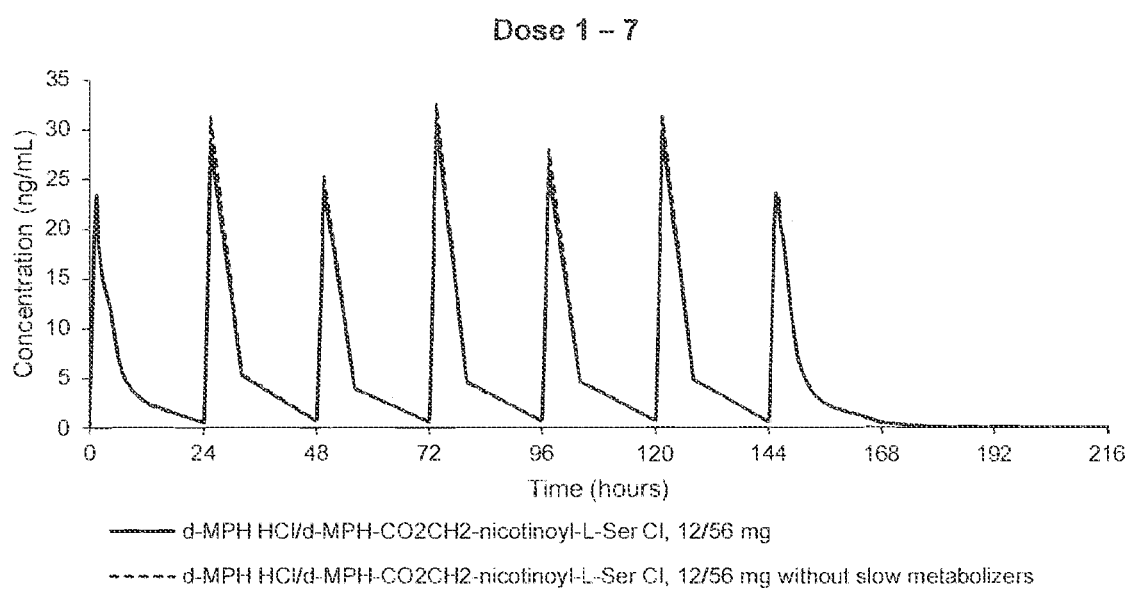
FIG. 21. Oral PK curves showing the mean d-MPH-CO$_2$CH$_2$-nicotinoyl-L-Ser plasma concentration-time profile following 7 oral doses of d-methylphenidate HCl/d-MPH-CO$_2$CH$_2$-nicotinoyl-L-Ser chloride, 12/56 mg administered in adult human subjects once every 24 hours calculated with and without outlier subjects.

FIG. 20 shows the mean (N=12) plasma concentration-time profile of the intact d-MPH-CO$_2$CH$_2$-nicotinoyl-L-Ser chloride following 7 oral doses of d-methylphenidate HCl/d-MPH-CO$_2$CH$_2$-nicotinoyl-L-Ser chloride 12/56 administered to adult human subjects once every 24 hours. FIG. 21 is similar to FIG. 20, but shows the mean (N=10) plasma concentration-time profile calculated without the two outlier subjects.

Figure 22:
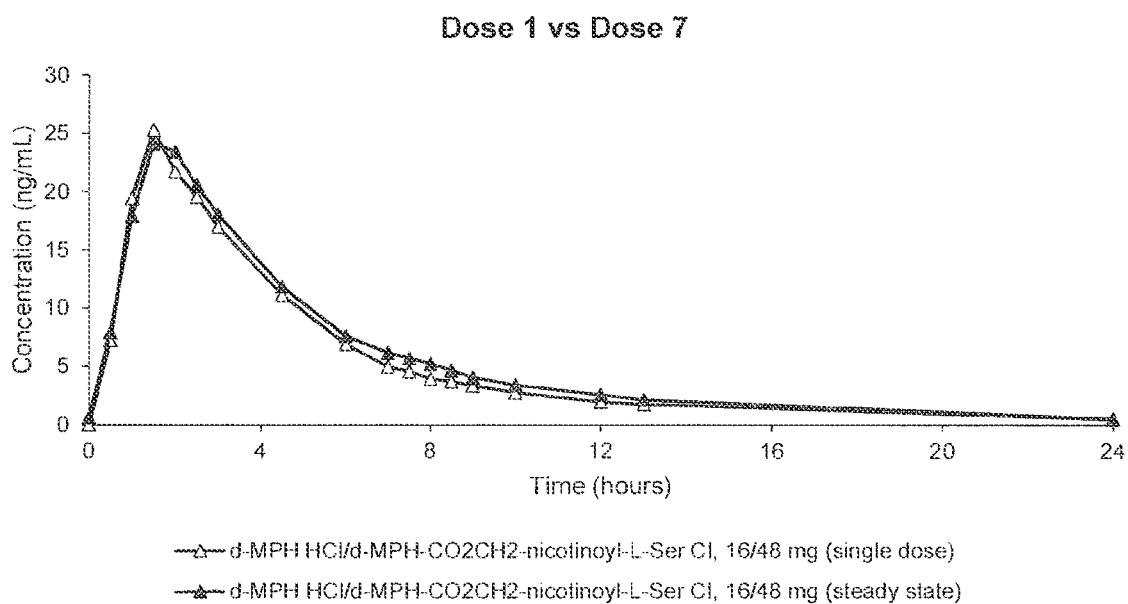
FIG. 22. Oral PK curves of the mean (N=12) d-MPH-CO$_2$CH$_2$-nicotinoyl-L-Ser plasma concentration-time profile following a single oral dose of d-methylphenidate HCl/d-MPH-CO$_2$CH$_2$-nicotinoyl-L-Ser chloride, 16/48 mg and following the 7$^{th}$ dose after multiple oral doses of d-methylphenidate HCl/d-MPH-CO$_2$CH$_2$-nicotinoyl-L-Ser chloride, 16/48 mg administered in adult human subjects once every 24 hours.
Figure 23:
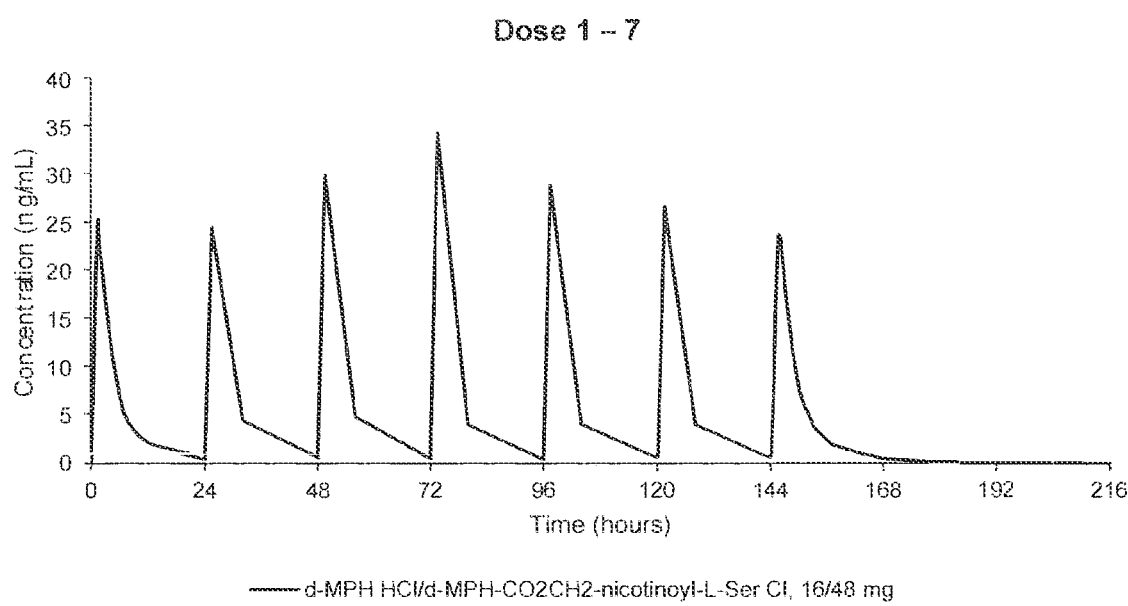
FIG. 23. Oral PK curves of the mean (N=12) d-MPH-CO$_2$CH$_2$-nicotinoyl-L-Ser plasma concentration-time profile following 7 oral doses of d-methylphenidate HCl/d-MPH-CO$_2$CH$_2$-nicotinoyl-L-Ser chloride, 16/48 mg administered in adult human subjects once every 24 hours.

FIG. 22 shows the mean (N=12) plasma concentration-time profile of intact d-MPH-CO$_2$CH$_2$-nicotinoyl-L-Ser chloride following a single oral dose of d-methylphenidate HCl/d-MPH-CO$_2$CH$_2$-nicotinoyl-L-Ser chloride 16/48 mg, and following the 7$^{th}$ dose after multiple doses of d-methylphenidate HCl/d-MPH-CO$_2$CH$_2$-nicotinoyl-L-Ser chloride 16/48 mg administered to adult human subjects once every 24 hours. FIG. 23 shows the mean (N=12) plasma concentration-time profile of the intact d-MPH-CO$_2$CH$_2$-nicotinoyl-L-Ser chloride following 7 oral doses of d-methylphenidate HCl/d-MPH-CO$_2$CH$_2$-nicotinoyl-L-Ser chloride 16/48 mg administered to adult human subjects once every 24 hours.

Figure 24:
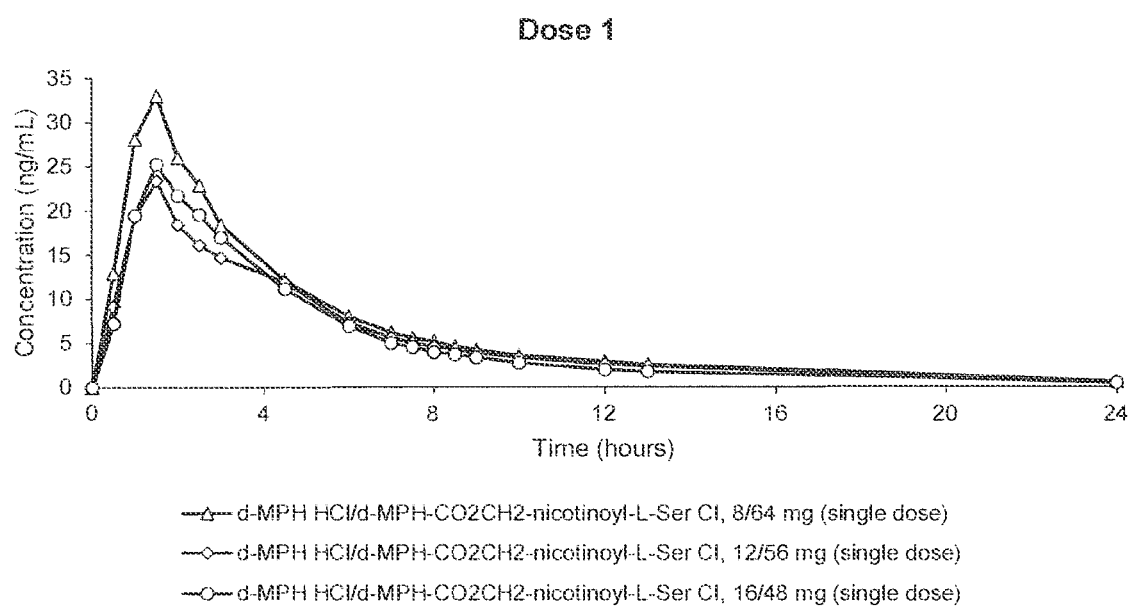
FIG. 24. Oral PK curves showing the mean d-MPH-CO$_2$CH$_2$-nicotinoyl-L-Ser plasma concentration-time profile following a single oral dose of d-methylphenidate HCl/d-MPH-CO$_2$CH$_2$-nicotinoyl-L-Ser chloride, 8/64 mg, d-methylphenidate HCl/d-MPH-CO$_2$CH$_2$-nicotinoyl-L-Ser chloride, 12/56 mg, and d-methylphenidate HCl/d-MPH-CO$_2$CH$_2$-nicotinoyl-L-Ser chloride, 16/48 mg, in adult human subjects.
Figure 25:
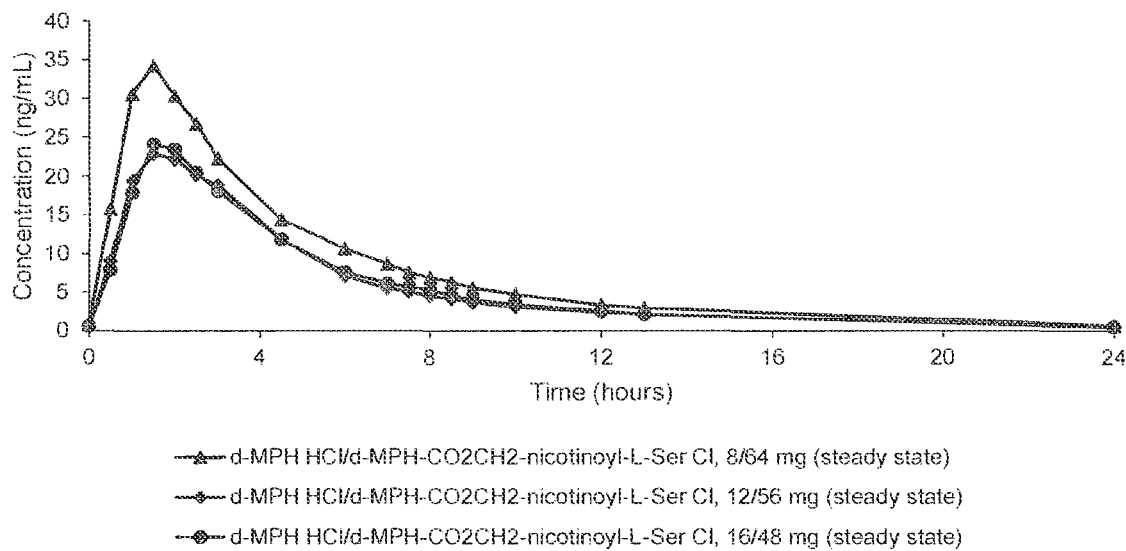
FIG. 25. Oral PK curves showing the mean (N=12) d-MPH-CO$_2$CH$_2$-nicotinoyl-L-Ser plasma concentration-time profile following the 7$^{th}$ dose after multiple oral doses of d-methylphenidate HCl/d-MPH-CO$_2$CH$_2$-nicotinoyl-L-Ser chloride, 8/64 mg, d-methylphenidate HCl/d-MPH-CO$_2$CH$_2$-nicotinoyl-L-Ser chloride, 12/56 mg, and d-methylphenidate HCl/d-MPH-CO$_2$CH$_2$-nicotinoyl-L-Ser chloride, 16/48 mg, administered in adult human subjects once every 24 hours.

FIGS. 24 and 25, respectively, show the mean (N=12) plasma concentration-time profile of intact d-MPH-CO$_2$CH$_2$-nicotinoyl-L-Ser chloride for each of the three dose mixtures following a single oral dose of d-methylphenidate HCl/d-MPH-CO$_2$CH$_2$-nicotinoyl-L-Ser chloride, and following the 7$^{th}$ dose after multiple doses of d-methylphenidate HCl/d-MPH-CO$_2$CH$_2$-nicotinoyl-L-Ser chloride administered to adult human subjects once every 24 hours.

As shown in each of the FIGS. 14-25, plasma concentrations of intact d-MPH-CO$_2$CH$_2$-nicotinoyl-L-Ser chloride were increased from about 0 to about 2 hours following oral administration, and slowly decreased to <1 ng/mL, showing negligible accumulation of the intact d-MPH-CO$_2$CH$_2$-nicotinoyl-L-Ser chloride at 24 hours post dose. Comparing dose 1 vs. dose 7 plasma concentrations at 24 hours, it can be seen that there is a negligible accumulation of the intact d-MPH-CO$_2$CH$_2$-nicotinoyl-L-Ser chloride in the bloodstream after the 7$^{th}$ dose. Significant plasma concentrations of the intact d-MPH-CO$_2$CH$_2$-nicotinoyl-L-Ser chloride that gradually decrease suggest that circulating prodrug levels contribute to the extended release profile by continuously releasing d-methylphenidate over time.

Figure 26:
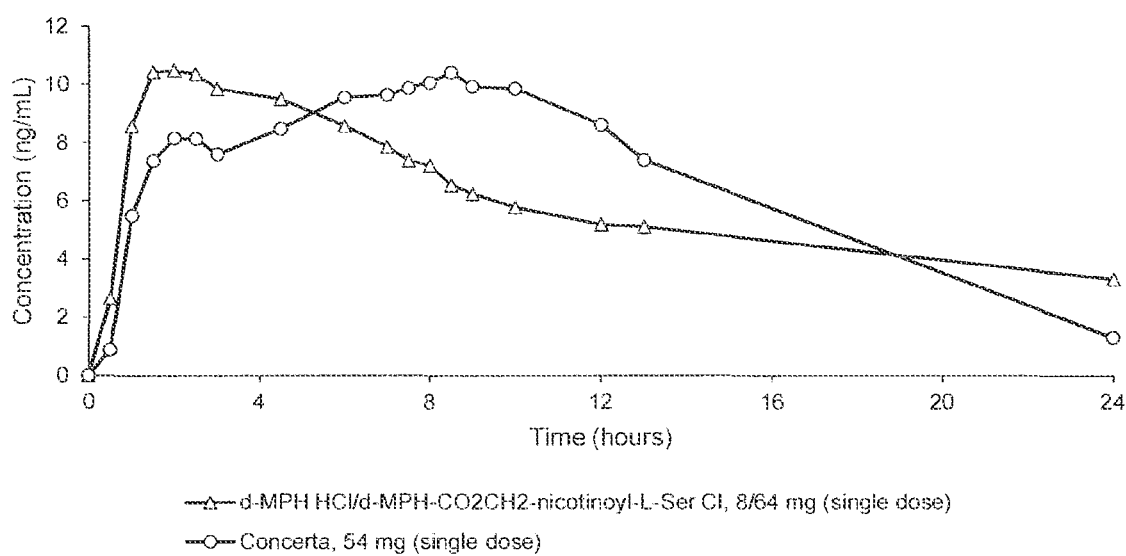
FIG. 26. Oral PK curves showing d-methylphenidate plasma concentration-time profiles following a single oral dose of d-methylphenidate HCl/d-MPH-CO$_2$CH$_2$-nicotinoyl-L-Ser chloride, 8/64 mg, and Concerta®, 54 mg, in adult human subjects.
Figure 27:
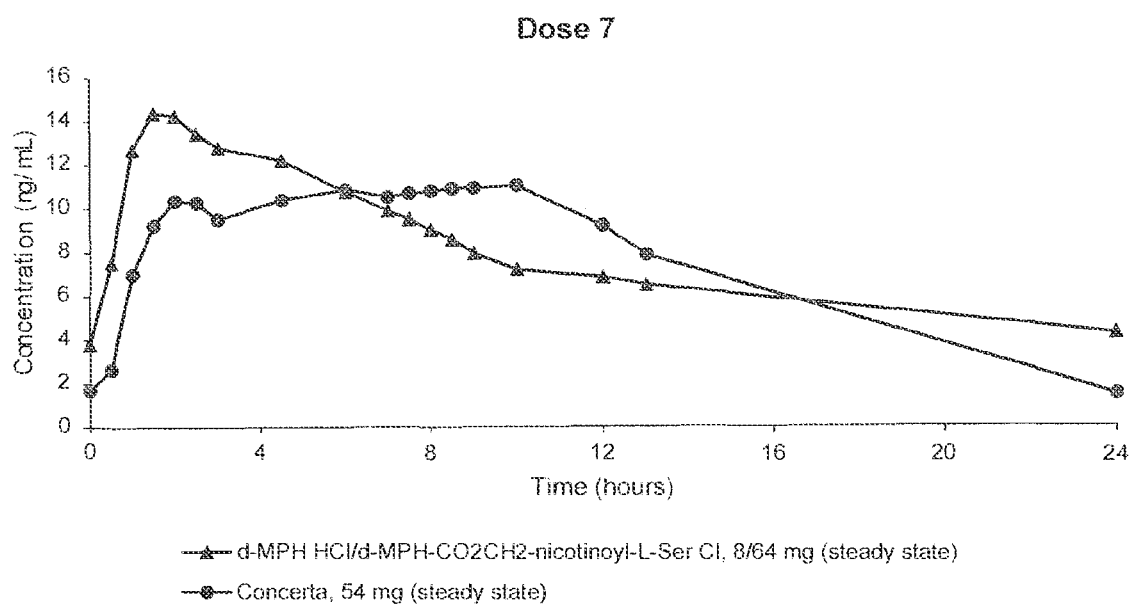
FIG. 27. Oral PK curves showing d-methylphenidate plasma concentration-time profiles following the 7th dose after multiple oral doses of d-methylphenidate HCl/d-MPH-CO$_2$CH$_2$-nicotinoyl-L-Ser chloride, 8/64 mg, and Concerta®, 54 mg, administered in adult human subjects once every 24 hours.
Figure 28:
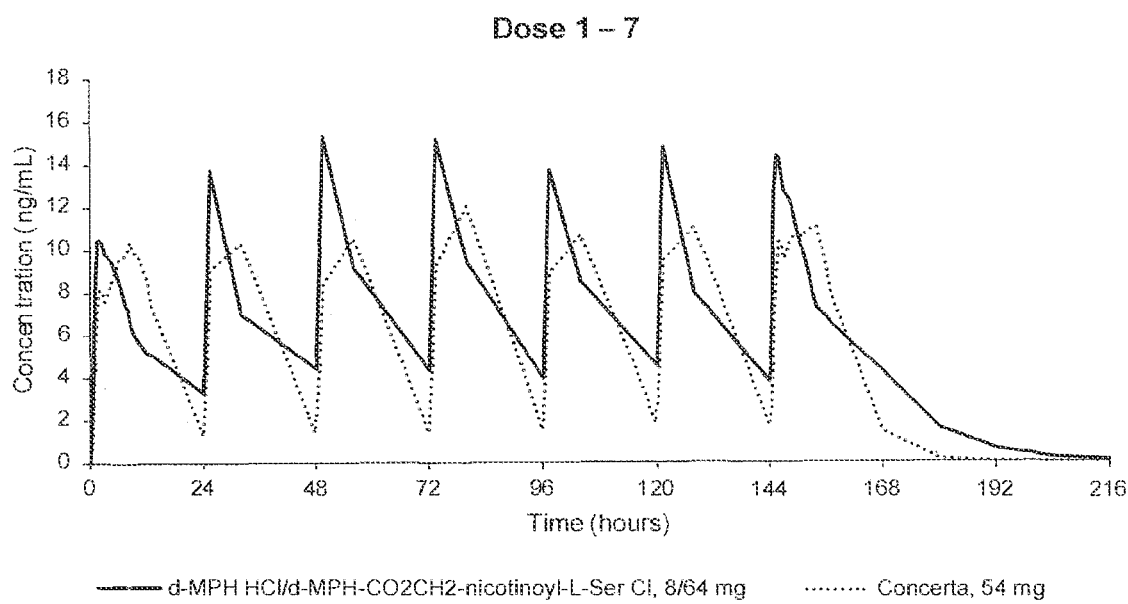
FIG. 28. Oral PK curves showing d-methylphenidate plasma concentration-time profiles following 7 oral doses of d-methylphenidate HCl/d-MPH-CO$_2$CH$_2$-nicotinoyl-L-Ser chloride, 8/64 mg, and Concerta®, 54 mg, taken once every 24 hours for 7 days in adult human subjects.

FIGS. 26-35 show the plasma concentration-time profiles for each of the dose mixtures 8/64 mg, 12/56 mg, and 16/48 mg, compared to Concert®® 54 mg. FIGS. 26-28, respectively, show the plasma concentration-time profiles for the 8/64 mg dose and Concerta®, 54 mg following a single oral dose, following the 7$^{th}$ oral dose after multiple oral doses, and for 7 oral doses, each administered once every 24 hours.

Figure 29:
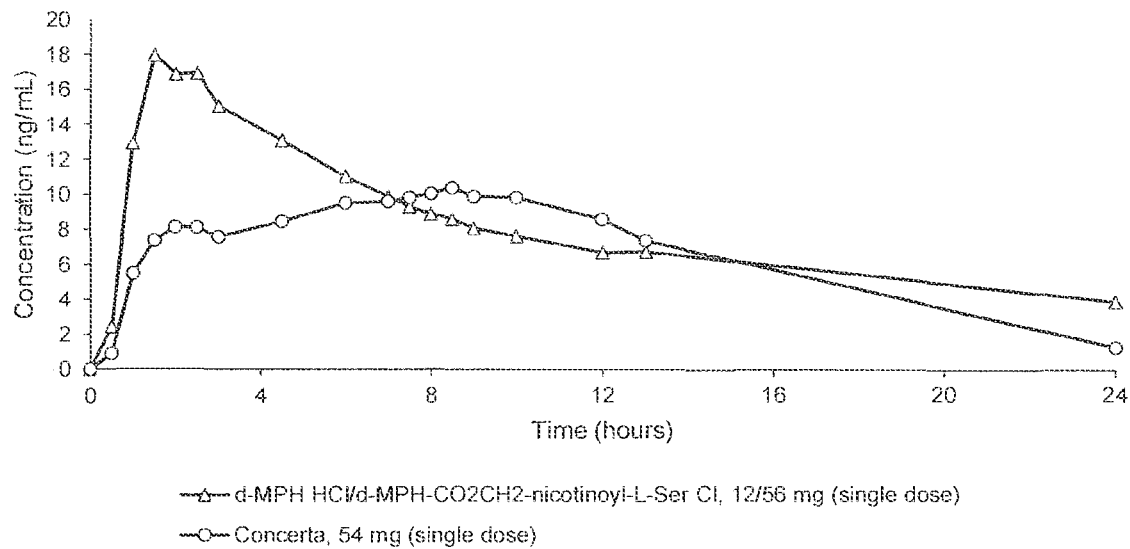
FIG. 29. Oral PK curves showing d-methylphenidate plasma concentration-time profiles following a single oral dose of d-methylphenidate HCl/d-MPH-CO$_2$CH$_2$-nicotinoyl-L-Ser chloride, 12/56 mg, and Concerta®, 54 mg, in adult human subjects.
Figure 30:
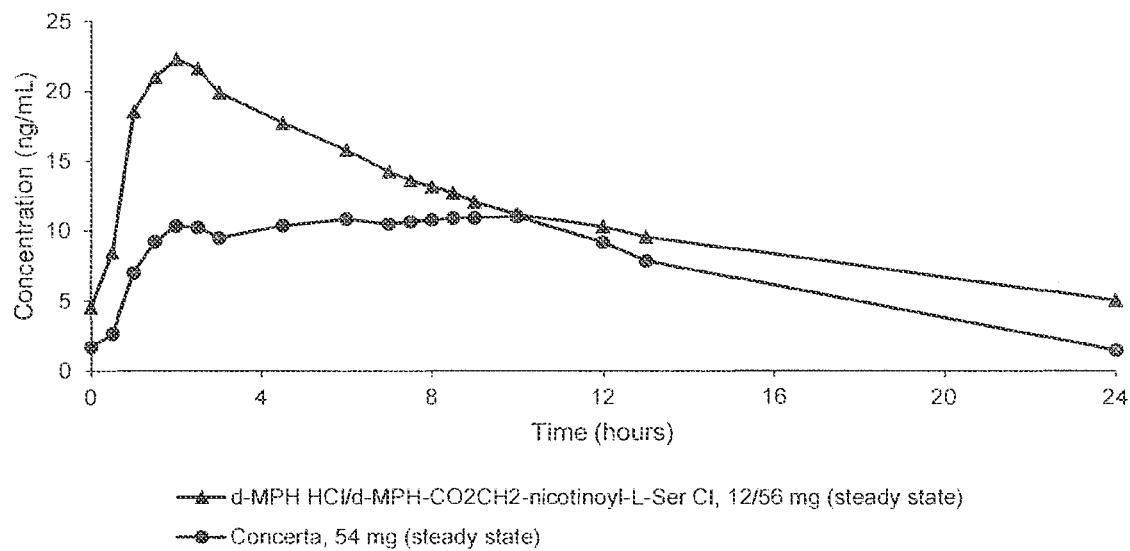
FIG. 30. Oral PK curves showing d-methylphenidate plasma concentration-time profiles following the 7th dose after multiple oral doses of d-methylphenidate HCl/d-MPH-CO$_2$CH$_2$-nicotinoyl-L-Ser chloride, 12/56 mg, and Concerta®, 54 mg, administered in adult human subjects once every 24 hours.
Figure 31:
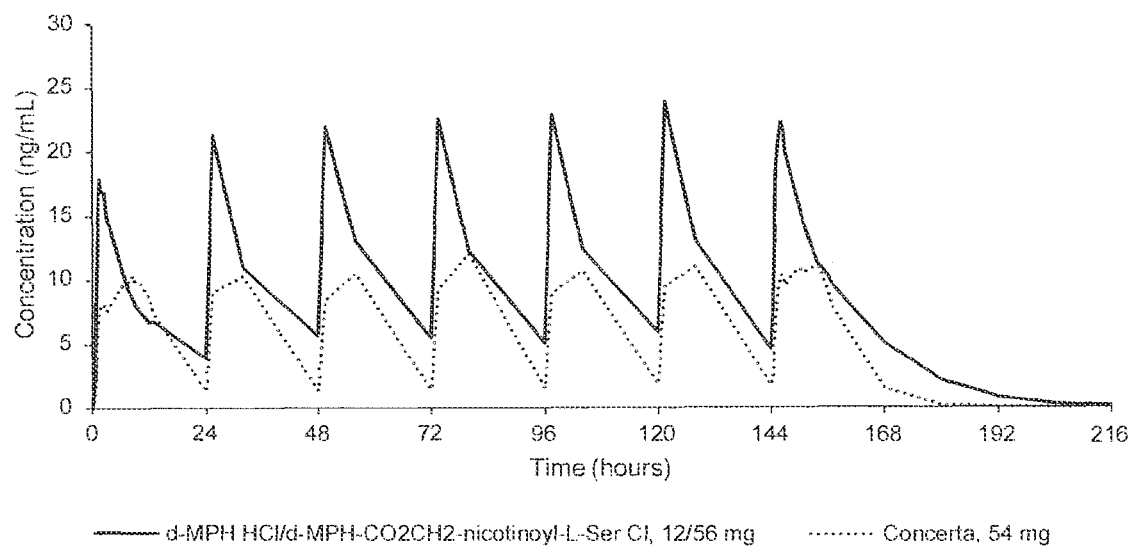
FIG. 31. Oral PK curves showing d-methylphenidate plasma concentration-time profiles following 7 oral doses of d-methylphenidate HCl/d-MPH-CO$_2$CH$_2$-nicotinoyl-L-Ser chloride, 12/56 mg, and Concerta®, 54 mg, taken once every 24 hours for 7 days in adult human subjects.
Figure 32:
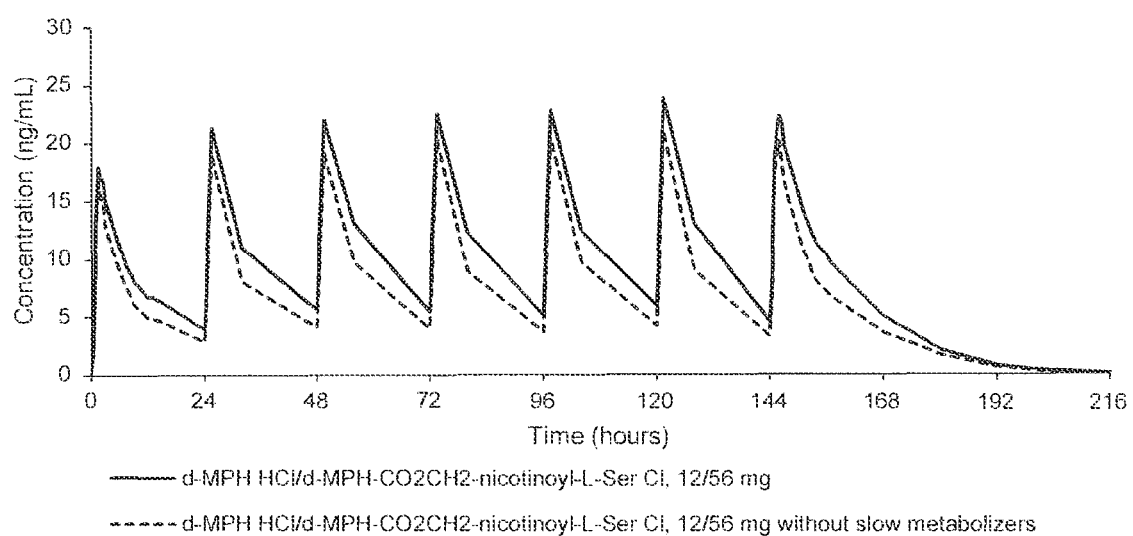
FIG. 32. Oral PK curves showing the mean d-methylphenidate plasma concentration-time profile following 7 oral doses of d-methylphenidate HCl/d-MPH-CO$_2$CH$_2$-nicotinoyl-L-Ser chloride, 12/56 mg, administered in adult human subjects once every 24 hours calculated with and without outlier subjects.

FIGS. 29-31, respectively, show the plasma concentration-time profiles for the 12/56 mg dose and Concerta®, 54 mg following a single oral dose, following the 7$^{th}$ oral dose after multiple oral doses, and for 7 oral doses, each administered once every 24 hours. FIG. 32 shows the concentration-time profile following 7 oral doses of d-methylphenidate HCl/d-MPH-CO$_2$CH$_2$-nicotinoyl-L-Ser chloride 12/56 mg administered to adult human subjects once every 24 hours, with and without the two outlier subjects.

Figure 33:
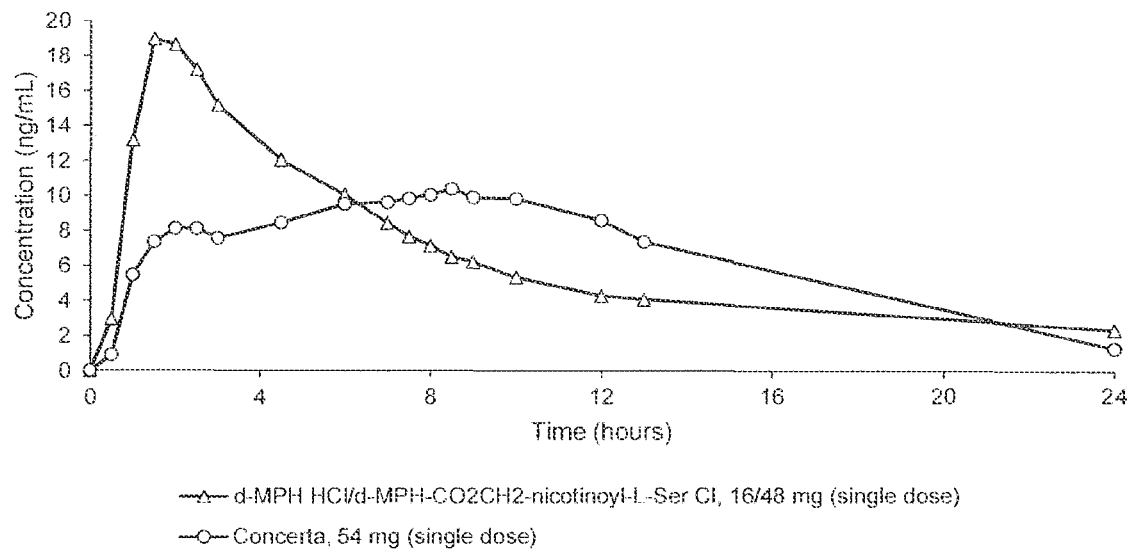
FIG. 33. Oral PK curves showing d-methylphenidate plasma concentration-time profiles following a single oral dose of d-methylphenidate HCl/d-MPH-CO$_2$CH$_2$-nicotinoyl-L-Ser chloride, 16/48 mg, and Concerta®, 54 mg, in adult human subjects.
Figure 34:
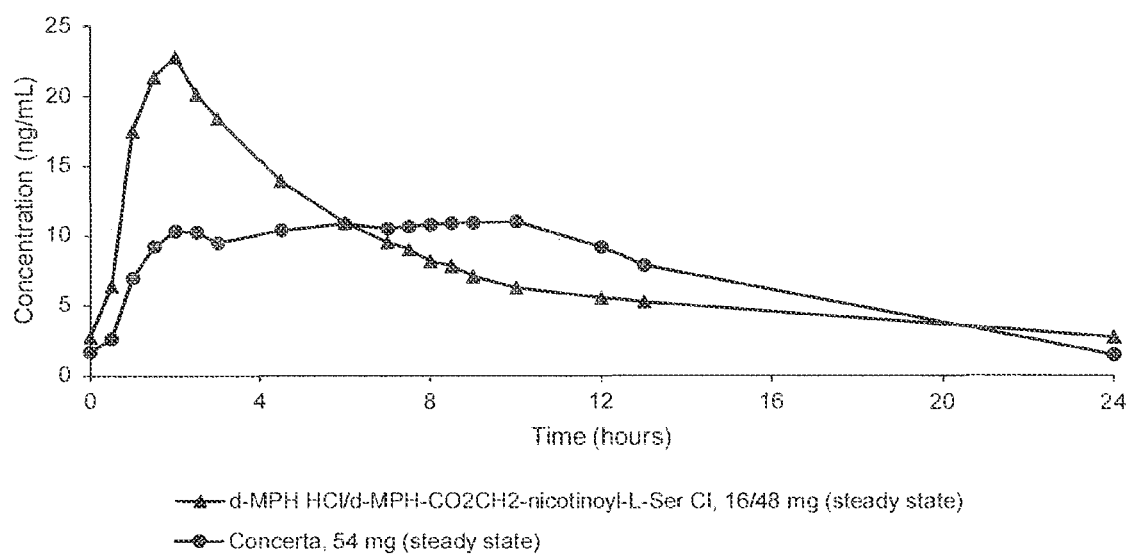
FIG. 34. Oral PK curves showing d-methylphenidate plasma concentration-time profiles following the 7th oral dose after multiple oral doses of d-methylphenidate HCl/d-MPH-CO$_2$CH$_2$-nicotinoyl-L-Ser chloride, 16/48 mg, and Concerta®, 54 mg, administered in adult human subjects once every 24 hours.
Figure 35:
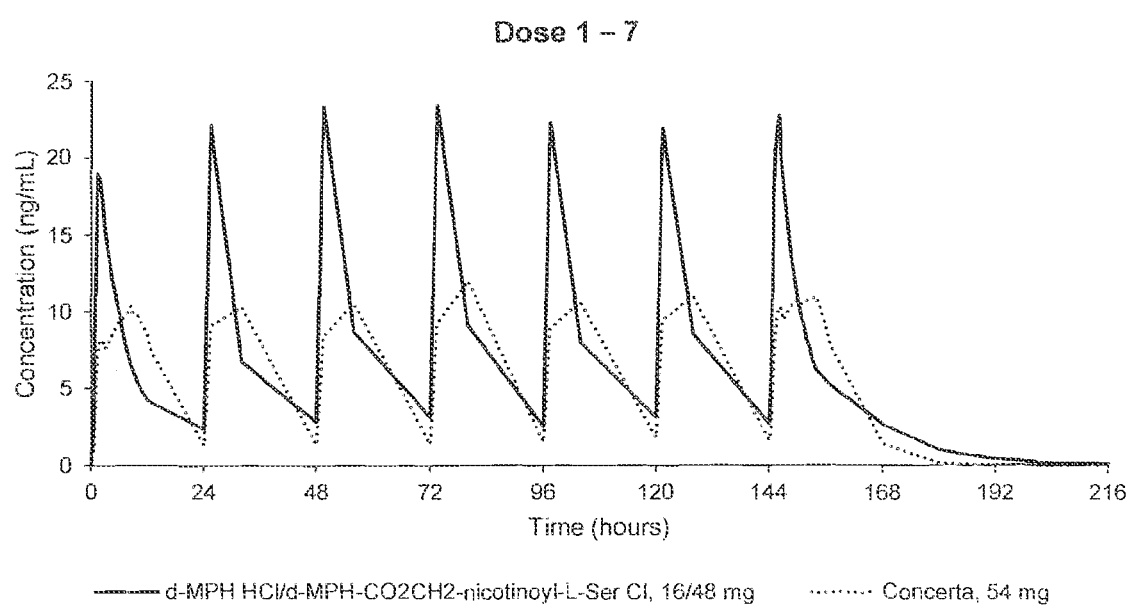
FIG. 35. Oral PK curves showing d-methylphenidate plasma concentration-time profiles following 7 oral doses of d-methylphenidate HCl/d-MPH-CO$_2$CH$_2$-nicotinoyl-L-Ser chloride, 16/48 mg, and Concerta®, 54 mg, taken once every 24 hours for 7 days in adult human subjects.

FIGS. 33-35, respectively, show the plasma concentration-time profiles for the 16/48 mg dose and Concerta®, 54 mg following a single oral dose, following the 7$^{th}$ oral dose after multiple oral doses, and for 7 oral doses, each administered once every 24 hours. As shown in FIGS. 26-28, 29-31, and 33-35, the plasma concentration of d-methylphenidate is increased from about 0 to about 4 hours following administration for each of the dose mixtures, 8/64 mg, 12/56 mg, and 16/48 mg, when compared to Concerta®, 54 mg. These Figures also show a more gradual decrease in the plasma concentration of d-methylphenidate for the three dose mixtures when compared to Concerta®, 54 mg. It can also be seen from these Figures that the plasma concentration of d-methylphenidate is increased at 24 hours for the three dose mixtures compared to Concerta® 54 mg. Steady state exposure to d-methylphenidate is reached. by day 7 (or earlier).

TABLE 12

PK parameters following oral administration of d-methylphenidate HCl/d-MPH-CO$_2$CH$_2$-nicotinoyl-L-Ser chloride 8/64 mg.

| | Analyte | |
| --- | --- | --- |
| Mean Parameter | d-MPH | d-MPH-CO$_2$CH$_2$-nicotinoyl-L-Ser chloride |
| Dose 1 | | |
| C$_{max}$ (ng/mL) | 11.7 | 32.5 |
| AUC$_{0-24}$ (h*ng/mL) | 142.5 | 152.1 |
| T$_{max}$ (hours)[median] | 2.2 [2] | 1.5 [1.5] |
| Dose 7 | | |
| C$_{max}$ (ng/mL) | 15.5 | 36.1 |
| AUC$_{0-24}$ (h*ng/mL) | 187.0 | 181.0 |
| T$_{max}$ (hours)[median] | 1.6 [1.5] | 1.6 [1.5] |
| Accumulation | | |
| C$_{max}$ (%) | 33.5 | 11.2 |
| AUC$_{0-24}$ (%) | 31.3 | 22.6 |

TABLE 13

PK parameters following oral administration of d-methylphenidate HCl/d-MPH-CO$_2$CH$_2$-nicotinoyl-L-Ser chloride 12/56 mg.

| | Analyte | | | |
| --- | --- | --- | --- | --- |
| | d-MPH | | d-MPH-CO$_2$CH$_2$-nicotinoyl-L-Ser chloride | |
| Mean Parameter | All subjects | Without Outliers | All subjects | Without Outliers |
| Dose 1 | | | | |
| C$_{max}$ (ng/mL) | 19.3 | 17.5 | 24.2 | 24.1 |
| AUC$_{0-24}$ (h*ng/mL) | 192.6 | 153.6 | 125.1 | 124.1 |
| T$_{max}$ (hours)[median] | 1.7 [1.5] | 1.6 [1.5] | 1.6 [1.5] | 1.6 [1.5] |

TABLE 13-continued

PK parameters following oral administration of d-methylphenidate HCl/d-MPH-CO$_2$CH$_2$-nicotinoyl-L-Ser chloride 12/56 mg.

| | Analyte | | | |
|---|---|---|---|---|
| | d-MPH | | d-MPH-CO$_2$CH$_2$-nicotinoyl-L-Ser chloride | |
| Mean Parameter | All subjects | Without Outliers | All subjects | Without Outliers |
| Dose 7 | | | | |
| C$_{max}$ (ng/mL) | 23.8 | 20.9 | 25.6 | 25.9 |
| AUC$_{0-24}$ (h*ng/mL) | 270.2 | 207.6 | 129.6 | 130.7 |
| T$_{max}$ (hours)[median] | 1.9 [1.75] | 1.75 [1.5] | 2 [1.75] | 2 [1.75] |
| Accumulation | | | | |
| C$_{max}$ (%) | 22.6 | 19.6 | 19.3 | 24.1 |
| AUC$_{0-24}$ (%) | 36.9 | 34.3 | 8.0 | 10.9 |

TABLE 14

PK parameters following oral administration of d-methylphenidate HCl/d-MPH-CO$_2$CH$_2$-nicotinoyl-L-Ser chloride 8/64 mg.

| | Analyte | |
|---|---|---|
| Mean Parameter | d-MPH | d-MPH-CO$_2$CH$_2$-nicotinoyl-L-Ser chloride |
| Dose 1 | | |
| C$_{max}$ (ng/mL) | 20.2 | 25.6 |
| AUC$_{0-24}$ (h*ng/mL) | 153.9 | 121.3 |
| T$_{max}$ (hours)[median] | 1.7 [1.5] | 1.6 [1.5] |
| Dose 7 | | |
| C$_{max}$ (ng/mL) | 23.8 | 25.9 |
| AUC$_{0-24}$ (h*ng/mL) | 187.1 | 132.6 |
| T$_{max}$ (hours)[median] | 1.7 [1.75] | 1.7 [1.5] |
| Accumulation | | |
| C$_{max}$ (%) | 19.5 | 16.7 |
| AUC$_{0-24}$ (%) | 24.8 | 20.6 |

TABLE 15

PK parameters following oral administration of Concerta ® 54 mg.

| | Analyte |
|---|---|
| Mean Parameter | d-MPH |
| Dose 1 | |
| C$_{max}$ (ng/mL) | 11.2 |
| AUC$_{0-24}$ (h*ng/mL) | 165.3 |
| T$_{max}$ (hours)[median] | 7.8 [8.25] |
| Dose 7 | |
| C$_{max}$ (ng/mL) | 12.6 |
| AUC$_{0-24}$ (h*ng/mL) | 176.6 |
| T$_{max}$ (hours)[median] | 5.0 [3.5] |
| Accumulation | |
| C$_{max}$ (%) | 13.4 |
| AUC$_{0-24}$ (%) | 13.2 |

Example 2: d-threo-MPH-CO$_2$CH$_2$-nicotinoyl-L-Ser and Sleep Disorders

A human study was conducted to evaluate the pharmacokinetics of d-MPH-CO$_2$CH$_2$-nicotinoyl-L-Ser and d-methylphenidate after oral administration of 60 mg d-MPH-CO$_2$CH$_2$-nicotinoyl-L-Ser chloride gelatin capsules in healthy volunteers under fasted and fed conditions. Fourteen (14) subjects were enrolled in this phase 1, open-label, single dose, two-period, randomized, crossover study. Eligible subjects included healthy male and female volunteers between the age of 18 and 55 years with a body mass index (BMI) between 18 and 32 kg/m$^2$ and a body weight between 50 and 100 kg at screening.

Two single-dose treatments were administered with a minimum 96-hour washout period between doses. Blood samples for pharmacokinetics were collected pre-dose and at 0.5, 0.75, 1, 1.5, 2, 2.5, 3, 3.5, 4.5, 6, 8, 10, 12, 16, 24, and 36 hours±5 minutes post-dose, in each treatment period.

Figure 36:
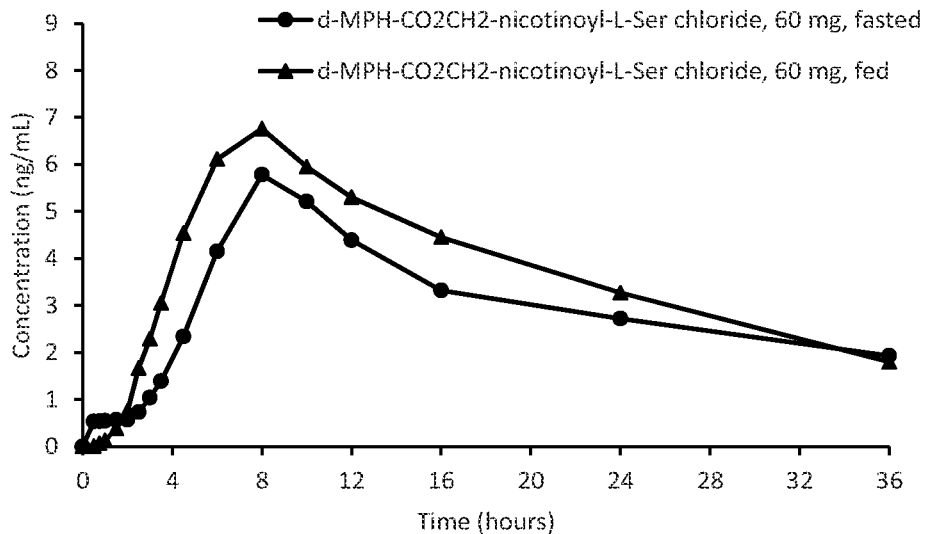
FIG. 36 depicts Plasma Concentration-Time Curves of d-MPH Following a Single Oral Dose of 60 mg d-MPH-CO$_2$CH$_2$-nicotinoyl-L-Ser Chloride in Human Adults in the Fasted and Fed State.
Figure 37:
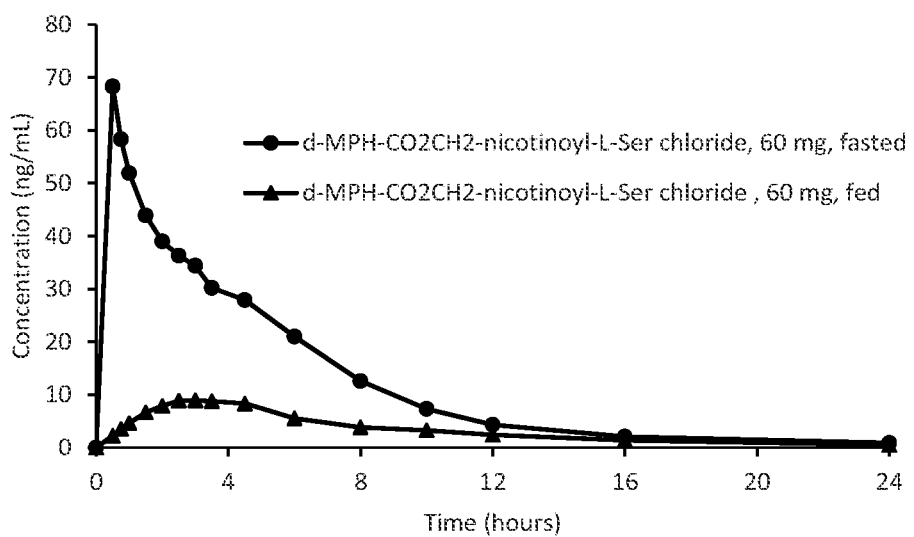
FIG. 37 depicts Plasma Concentration-Time Curves of d-MPH-CO$_2$CH$_2$-nicotinoyl-L-Ser Following a Single Oral Dose of 60 mg d-MPH-CO$_2$CH$_2$-nicotinoyl-L-Ser Chloride in Human Adults in the Fasted and Fed State.

FIGS. 36 and 37 show the mean (N=14) plasma concentration-time profile of d-MPH and d-MPH-CO$_2$CH$_2$-nicotinoyl-L-Ser, respectively, following oral administration of single doses of 60 mg d-MPH-CO$_2$CH$_2$-nicotinoyl-L-Ser chloride in the fasted and fed state.

In both, the fasted and fed state, plasma concentrations of d-MPH rise slowly and reach peak mean concentrations at 8 hours post-dose. Thereafter, exposure to d-MPH decreases very gradually with a long half-life of up to approximately 21.8 hours. While maximum d-MPH plasma concentrations were achieved at the same time point after each treatment, peak d-MPH exposure was slightly higher in the fed state.

TABLE 16

PK Parameters of d-MPH-CO$_2$CH$_2$-nicotinoyl-L-Ser and d-MPH Following a Single Oral Dose of 60 mg d-MPH-CO$_2$CH$_2$-nicotinoyl-L-Ser Chloride in Human Adults in the Fasted and Fed State.

| | Analyte | | | |
|---|---|---|---|---|
| | d-MPH-CO$_2$CH$_2$-nicotinoyl-L-Ser | | d-MPH | |
| PK Parameter[a] | Fasted | Fed | Fasted | Fed |
| C$_{max}$ (ng/mL) | 75.6 | 10.2 | 5.97 | 7.09 |
| AUC$_{0-last}$ (h*ng/mL) | 305.7 | 81.10 | 107.0 | 132.8 |
| AUC$_{0-inf}$ (h*ng/mL) | 309.0 | 84.16 | 167.5 | 170.1 |
| AUC$_{0-24\,hr}$ (h*ng/mL) | 299.5 | 77.89 | 79.14 | 102.3 |
| T$_{max}$ (h) | 0.50 (0.50-6.00) | 3.00 (1.00-4.50) | 8.00 (8.00-36.00) | 8.00 (4.50-24.00) |
| T$_{1/2}$ (h) | 5.84 | 6.10 | 21.78 | 14.66 |

[a]Mean value shown except for T$_{max}$ for which median (range) are presented)

In the present specification, use of the singular includes the plural except where specifically indicated.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

What is claimed:

1. A method of treating excessive daytime sleepiness associated with central hypersomnolence disorders, obstructive sleep apnea, or a shift work disorder, in a human or animal subject comprising administering to the human or animal subject a composition comprising a compound, wherein the compound is a conjugate of d-methylphenidate having the following chemical formula:

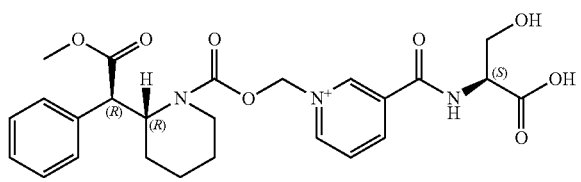

at least one salt thereof, or mixture thereof.

2. The method of claim 1, wherein the central hypersomnolence disorder is selected from the group consisting of narcolepsy type 1 (with cataplexy), narcolepsy type 2, idiopathic hypersomnia, Kleine-Levin syndrome, hypersomnia due to a medical condition, hypersomnia due to a medication or substance, hypersomnia associated with a psychiatric condition, and insufficient sleep syndrome.

3. The method of claim 1, wherein the at least one salt of the compound is at least one pharmaceutically or therapeutically acceptable salt form or salt mixture thereof.

4. The method of claim 3, wherein the at least one pharmaceutically or therapeutically acceptable salt form of the compound is selected from the group consisting of acetate, l-aspartate, besylate, bicarbonate, carbonate, d-camsylate, l-camsylate, citrate, edisylate, formate, fumarate, gluconate, hydrobromide, bromide, hydrochloride, chloride, d-lactate, l-lactate, d,l-lactate, d,l-malate, l-malate, mesylate, pamoate, phosphate, succinate, sulfate, bisulfate, d-tartrate, martrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, hydroxide, hydrogen sulfite (bisulfite), benzene sulfonate, hypophosphite, bromate, iodate, chlorate, fluoride, nitrite, and combinations thereof.

5. The method of claim 4, wherein the pharmaceutically or therapeutically acceptable salt form of the compound has the following structure:

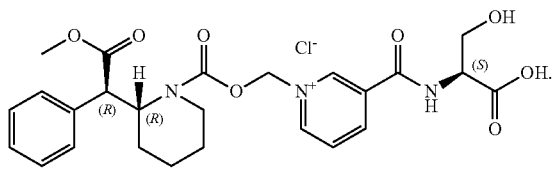

6. The method of claim 1, wherein the composition is in a dosage form selected from the group consisting of a sublingual, a gummy, a chewable tablet, a rapidly dissolving tablet, a tablet, a capsule, a caplet, a troche, a lozenge, an oral powder, a solution, a thin strip, an oral thin film (OTF), an oral strip, a rectal film, a syrup, a suspension, and a suppository.

7. The method of claim 1, wherein the composition is formulated for oral administration.

8. The method of claim 1, wherein the composition provides a dose amount that is the molar equivalent to a dose from about 0.1 mg to about 500 mg d-methylphenidate hydrochloride per dose.

9. The method of claim 1, wherein the composition is provided in a unit dose form, blister pack, roll, or bulk bottle.

10. The method of claim 9, wherein the unit dose form provides an amount of d-methylphenidate that is molar equivalent to about 0.5 mg to about 500 mg d-methylphenidate hydrochloride.

11. The method of claim 1, wherein the composition further comprises one or more excipients or one or more additional pharmaceutically active ingredients.

12. The method of claim 11, wherein the excipients are selected from the group consisting of antiadherents, binders, coatings, disintegrants, gel forming agents, fillers, flavors and colors, glidants, lubricants, preservatives, sorbents, and sweeteners.

* * * * *